US012788256B2

(12) United States Patent
Ting et al.

(10) Patent No.: US 12,788,256 B2
(45) **Date of Patent: *Nov. 10, 2026**

(54) DEVICES, SYSTEMS AND METHODS FOR TISSUE ANALYSIS, LOCATION DETERMINATION AND THERAPY THEREOF USING OPTICAL RADIATION

(71) Applicant: Blossom Innovations LLC, Waltham, MA (US)

(72) Inventors: Joseph Ting, Acton, MA (US); Vincent Zuo, Boston, MA (US); Ben Apollonio, Lunenburg, MA (US); Tania To, Braintree, MA (US); James Wright, Roxbury, MA (US); Charles Holland Dresser, Wayland, MA (US)

(73) Assignee: Blossom Innovations LLC, Waltham, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 18/418,665

(22) Filed: Jan. 22, 2024

(65) Prior Publication Data

US 2024/0156352 A1 May 16, 2024

Related U.S. Application Data

(63) Continuation of application No. 17/577,929, filed on Jan. 18, 2022, now abandoned, which is a
(Continued)

(51) Int. Cl.
*A61B 5/00* (2006.01)
*A61B 5/0538* (2021.01)
(Continued)

(52) U.S. Cl.
CPC .......... *A61B 5/0084* (2013.01); *A61B 5/0031* (2013.01); *A61B 5/4839* (2013.01);
(Continued)

(58) Field of Classification Search
None
See application file for complete search history.

(56) References Cited

U.S. PATENT DOCUMENTS 3,313,293 A 4/1967 Chesebrough et al.
3,682,162 A 8/1972 Colyer
(Continued)

FOREIGN PATENT DOCUMENTS

CN 101073497 A 11/2007
CN 101917901 A 12/2010
(Continued)

OTHER PUBLICATIONS

Extended European Search Report issued in European Patent application No. 20770696.1, mailed on Feb. 24, 2023.
(Continued)

*Primary Examiner* — Christopher Koharski
*Assistant Examiner* — Renee C Langhals
(74) *Attorney, Agent, or Firm* — Mintz Levin Cohn Ferris Glovsky and Popeo, P.C.

(57) ABSTRACT

A method of delivering a substance to a target location of a subject using an insertion apparatus having a base structure with at least one lumen extending along a length thereof, a cladding layer circumferentially surrounding the base structure and an optically-transmissive coating circumferentially surrounding an exterior of the base layer or an exterior of the cladding layer. The method includes inserting the insertion apparatus into the subject to access the target location, transmitting to tissue adjacent the insertion apparatus, a first optical radiation using the optically-transmissive coating or the cladding layer, receiving, from the tissue, at a processor, data characterizing a second optical radiation via the other of the optically-transmissive coating or the cladding layer based on the first optical radiation and determining whether
(Continued)

a tip of the base structure is at the target location, and, if so, releasing a substance into or near the target location.

16 Claims, 46 Drawing Sheets

Related U.S. Application Data continuation of application No. 17/438,816, filed as application No. PCT/US2020/022614 on Mar. 13, 2020, now abandoned.

(60) Provisional application No. 62/941,213, filed on Nov. 27, 2019, provisional application No. 62/941,202, filed on Nov. 27, 2019, provisional application No. 62/817,914, filed on Mar. 13, 2019.

(51) Int. Cl.
*A61B 10/02* (2006.01)
*A61B 10/04* (2006.01)
*A61B 18/00* (2006.01)
*A61B 18/20* (2006.01)
*A61B 34/20* (2016.01)
*A61M 5/46* (2006.01)

(52) U.S. Cl.
CPC .......... *A61B 5/4887* (2013.01); *A61B 5/6848* (2013.01); *A61B 5/7405* (2013.01); *A61B 5/742* (2013.01); *A61B 10/0233* (2013.01); *A61B 10/04* (2013.01); *A61B 18/20* (2013.01); *A61B 34/20* (2016.02); *A61M 5/46* (2013.01); *A61B 5/0538* (2013.01); *A61B 5/4872* (2013.01); *A61B 5/489* (2013.01); *A61B 2018/00577* (2013.01); *A61B 2034/2055* (2016.02)

(56) References Cited

U.S. PATENT DOCUMENTS 4,312,364 A 1/1982 Convert et al.
4,469,109 A 9/1984 Mehl
4,566,183 A 1/1986 Bloom et al.
5,279,306 A 1/1994 Mehl et al.
5,294,325 A 3/1994 Liu
5,341,807 A 8/1994 Nardella
5,634,924 A 6/1997 Turkel et al.
5,651,783 A * 7/1997 Reynard ................ A61B 90/36 606/4
5,658,279 A 8/1997 Nardella et al.
5,904,709 A 5/1999 Arndt et al.
5,947,964 A 9/1999 Eggers et al.
5,997,568 A 12/1999 Liu
6,117,133 A 9/2000 Zappala
6,182,666 B1 2/2001 Dobak
6,230,060 B1 5/2001 Mawhinney
6,315,777 B1 11/2001 Comben
6,356,783 B1 3/2002 Hubbard, Jr.
6,371,943 B1 4/2002 Racz et al.
6,509,521 B1 1/2003 Geitz
6,673,068 B1 1/2004 Berube
7,160,292 B2 1/2007 Moorman et al.
7,488,295 B2 2/2009 Burbank et al.
7,862,563 B1 1/2011 Cosman et al.
8,133,033 B2 3/2012 Abraham
8,396,532 B2 3/2013 Jenkins et al.
8,953,911 B1 * 2/2015 Xu .......................... G02B 6/26 385/12
10,687,730 B2 6/2020 Kronström et al.
10,779,804 B2 9/2020 Kronstrom et al.
11,191,446 B2 12/2021 Ting et al.
11,432,733 B2 9/2022 Ting et al.
2002/0042594 A1 4/2002 Lum et al.
2002/0072686 A1 6/2002 Hoey et al.
2002/0165448 A1 11/2002 Ben-haim et al.
2003/0078572 A1 4/2003 Pearson et al.
2003/0109871 A1 6/2003 Johnson et al.
2003/0187366 A1 10/2003 Hashimshony
2003/0195500 A1 10/2003 Moorman et al.
2004/0143218 A1 7/2004 Das
2005/0090820 A1 4/2005 Cornelius et al.
2005/0203505 A1 9/2005 Megerman et al.
2005/0277829 A1 12/2005 Tsonton et al.
2005/0279354 A1 12/2005 Deutsch et al.
2005/0288566 A1 12/2005 Levendusky et al.
2006/0190006 A1 8/2006 Oka et al.
2006/0285350 A1 12/2006 Wang
2007/0179491 A1 8/2007 Kratoska et al.
2007/0179508 A1 8/2007 Arndt
2007/0260156 A1 11/2007 Hashimshony
2008/0015570 A1 1/2008 Ormsby et al.
2008/0033424 A1 2/2008 Van et al.
2009/0088711 A1 4/2009 Shelley et al.
2009/0112201 A1 4/2009 Young
2009/0171304 A1 7/2009 Cao et al.
2009/0227952 A1 * 9/2009 Blakstvedt ........... A61B 5/0084 604/117
2009/0295674 A1 12/2009 Bonn
2009/0306522 A1 12/2009 Gono et al.
2010/0004650 A1 1/2010 Ormsby et al.
2010/0204560 A1 8/2010 Salahieh et al.
2010/0268219 A1 10/2010 Ormsby et al.
2010/0286507 A1 11/2010 Paassilta et al.
2010/0298822 A1 11/2010 Behnke
2011/0060229 A1 * 3/2011 Hulvershorn ........ A61B 5/0006 600/561
2011/0077635 A1 3/2011 Bonn
2011/0098695 A1 4/2011 Brannan
2011/0212411 A1 9/2011 Sinofsky
2012/0310315 A1 12/2012 Savage et al.
2013/0116679 A1 5/2013 Van et al.
2014/0088371 A1 3/2014 Vayser et al.
2014/0133814 A1 5/2014 Stevens et al.
2014/0212083 A1 7/2014 Pare et al.
2014/0228838 A1 8/2014 Kirschenman
2014/0303494 A1 10/2014 Janicki et al.
2014/0316254 A1 10/2014 Eversull et al.
2015/0119674 A1 4/2015 Fischell et al.
2015/0209105 A1 7/2015 Balbs et al.
2015/0216442 A1 8/2015 Lavy et al.
2015/0272451 A1 10/2015 Razavi et al.
2015/0282451 A1 10/2015 Kuennen
2015/0351670 A1 12/2015 Vanslyke et al.
2015/0374915 A1 12/2015 Hyde et al.
2016/0029920 A1 2/2016 Kronström et al.
2016/0066894 A1 3/2016 Barton-sweeney
2016/0081585 A1 3/2016 Halter
2016/0331290 A1 11/2016 Oh et al.
2017/0042408 A1 * 2/2017 Washburn .............. A61B 1/317
2017/0049378 A1 2/2017 Schipper et al.
2017/0086801 A1 3/2017 Furlong et al.
2017/0143201 A1 5/2017 Claude et al.
2017/0172618 A1 6/2017 Erkamp et al.
2017/0254636 A1 9/2017 Foster et al.
2017/0311807 A1 11/2017 Fu et al.
2017/0354379 A1 12/2017 Goyal et al.
2018/0140278 A1 5/2018 Bromberg et al.
2018/0250217 A1 9/2018 Davidson et al.
2018/0296146 A1 10/2018 Harttig
2018/0296197 A1 10/2018 Kronström et al.
2018/0317896 A1 11/2018 Kadamus et al.
2018/0325499 A1 * 11/2018 Landey .................. A61B 5/061
2018/0360342 A1 12/2018 Fuimaono et al.
2019/0029751 A1 1/2019 Hancock et al.
2019/0038348 A1 2/2019 Koblish et al.
2019/0125447 A1 5/2019 Ben Oren et al.
2019/0200930 A1 7/2019 Lowery
2019/0328295 A1 10/2019 Liu et al.
2020/0015684 A1 * 1/2020 Stone ................... A61B 5/0084
2020/0037924 A1 2/2020 Govari et al.
2020/0289021 A1 9/2020 Ting et al.

(56) References Cited

U.S. PATENT DOCUMENTS

| | | | |
|---|---|---|---|
| 2020/0367757 A1 | 11/2020 | Ting et al. |
| 2021/0085212 A1 | 3/2021 | Czaplewski-campbell et al. |
| 2021/0259573 A1 | 8/2021 | Ting et al. |
| 2021/0270705 A1 | 9/2021 | Van et al. |
| 2022/0095925 A1 | 3/2022 | Ting et al. |
| 2022/0133152 A1 | 5/2022 | Ting et al. |
| 2023/0148867 A1 | 5/2023 | Ting et al. |

FOREIGN PATENT DOCUMENTS

| | | | |
|---|---|---|---|
| CN | 204033333 | U | 12/2014 |
| CN | 104739503 | A | 7/2015 |
| CN | 103717249 | B | 3/2017 |
| CN | 108601582 | A | 9/2018 |
| CN | 108670174 | A | 10/2018 |
| CN | 208447588 | U | 2/2019 |
| CN | 106061420 | B | 12/2021 |
| DE | 102017004548 | A1 | 6/2018 |
| JP | 2011507648 | A | 3/2011 |
| JP | 2011521672 | A | 7/2011 |
| JP | 2015512711 | A | 4/2015 |
| JP | 2016504090 | A | 2/2016 |
| WO | 2007075091 | A2 | 7/2007 |
| WO | 2014162242 | A1 | 10/2014 |
| WO | 2015155671 | A1 | 10/2015 |
| WO | 2017058620 | A1 | 4/2017 |
| WO | 2018015782 | A1 | 1/2018 |
| WO | 2018175348 | A1 | 9/2018 |
| WO | 2018200865 | A1 | 11/2018 |
| WO | 2020186153 | A1 | 9/2020 |
| WO | 2020186164 | A1 | 9/2020 |
| WO | 2021054974 | A1 | 3/2021 |
| WO | 2021108704 | A1 | 6/2021 |

OTHER PUBLICATIONS (2022) "Integral", www.dictionary.com/browse/integral, 7 pages.

International Search Report and Written Opinion received for PCT Application No. PCT/US2020/022614, mailed on Jul. 1, 2020, 13 pages.

International Search Report and Written Opinion received for PCT Application No. PCT/US2020/022641, mailed on Jun. 15, 2020, 11 pages.

Principles of Electrosurgery, Covidien, Boulder CO, 2008, 1-28.

Abduljabbar et al. (2016) "Complications of Hyaluronic Acid Fillers and Their Managements", Journal of Dermatology & Dermatologic Surgery, 20:100-106.

Bouma et al. (2017) "Intravascular Optical Coherence Tomography [Invited]", Biomedical Optics Express, 8 (5):2660-2686.

Burgher et al. (2002) "PhotoPoint Photodynamic Therapy with Local Drug Delivery Eliminates Vessel Wall Cells in Arteriovenous Graft Models", Cardiovascular radiation medicine, 3(3-4):163-168.

Cano, Antony Ivorra (Feb. 2005) "Contributions to the Measurement of Electrical Impedance for Living Tissue Ischemia Injury Monitoring", Doctoral Thesis, Universitat Politecnica de Catalunya, 1-20.

Dukkipati et al. (Sep. 22, 2015) "Pulmonary Vein Isolation Using the Visually Guided Laser Balloon: A Prospective, Multicenter, and Randomized Comparison to Standard Radiofrequency Ablation", Journal of the American College of Cardiology, 66(12):1350-1360.

Goldman et al. (May 2015) "Phase 2a, Randomized, Double-Blind, Placebo-Controlled Dose-Ranging Study of Repeat Doses of Collagenase Clostridium Histolyticum for the Treatment of Edematous Fibrosclerotic Panniculopathy (Cellulite)", Journal of the American Academy of Dermatology, 72(5):1 page.

(2021) "Integral", Merriam-Webster.com, https://www.merriam-webster.com/dictionary/integral, printed Aug. 23, 2021, 12 pages.

Liberman, Laura (May 2000) "Percutaneous Imaging-Guided Core Breast Biopsy: State of the Art at the Millennium", AJR, 174(5):1191-1199.

Pelras et al. (2017) "Transparent Low Molecular Weight Poly{Ethylene Glycol) Diacrylate-Based Hydrogels as Film Media for Photoswitchable Drugs", Polymers, 9(12):639 (14 pages).

Ribatti et al. (2010) "Angiogenesis and Melanoma", Cancers, 2(1):114-132.

Rocha et al. (Jul. 2013) "Step-by-Step of Ultrasound-Guided Core-Needle Biopsy of the Breast: Review and Technique", Radiol Bras., 46(4):234-241.

Schar et al. (May 2014) "Anti-Infective Therapy of Peri-Implantitis with Adjunctive Local Drug Delivery or Photodynamic Therapy: Six-month Outcomes of a Prospective Randomized Clinical Trial", Clinical Oral Implants Research, 24(1):104-110.

Selfridge et al. (Nov. 2000) "Wideband Spherically Focused PVDF Acoustic Sources for Calibration of Ultrasound Hydrophone Probes," IEEE Transactions on Ultrasonics, Ferroelectrics, and Frequency Control, 47 (6):1372-1376.

Sepulveda et al. (May 2014) "Vascular Tumors", Seminars in Plastic Surgery, 28(2):49-57.

Utzinger et al. (Jan. 2003) "Fiber Optic Probes for Biomedical Optical Spectroscopy", Journal of Biomedical Optics, 8(1):121-147.

Yun et al. (Nov. 2017) "Fabrication of Fine Electrodes on the Tip of Hypodermic Needle Using Photoresist Spray Coating and Flexible Photomask for Biomedical", Journal of Visualized Experiments, 129:56622 (8 pages).

Yun et al. (2016) "Micro electrical impedance spectroscopy on a needle for ex vivo discrimination between human normal and cancer renal tissues", Biomicrofluidics, 10(3):034109 (9 pages).

* cited by examiner

Measured Response Showed a Distinct Difference Between Fat and Other Tissues and Blood Needle 3 (uninsulated)

Needle 5 (insulated)

Comparative Needle Response

Analzer

AD5933

2191

2192

2193

2194

DEVICES, SYSTEMS AND METHODS FOR TISSUE ANALYSIS, LOCATION DETERMINATION AND THERAPY THEREOF USING OPTICAL RADIATION

CROSS-REFERENCE TO RELATED APPLICATION(S)

This application is a continuation of U.S. patent application Ser. No. 17/577,929 filed on Jan. 18, 2022, and U.S. patent application Ser. No. 17/438,816 filed on Sep. 13, 2021, and relates to, and claims the benefit and priority from International Patent Application No. PCT/US2020/022614 filed on Mar. 13, 2020 that published as International Patent Application No. WO 2020/186153 on Sep. 17, 2020, which claims the benefit and priority from U.S. Provisional priority from U.S. Patent Application Ser. No. 62/817,914, filed on Mar. 13, 2019, and U.S. Patent Application Ser. No. 62/941,213 filed on Nov. 27, 2019, and U.S. Provisional Patent Application Ser. No. 62/941,202, filed on Nov. 27, 2019, the entire disclosures of which are incorporated herein by reference.

FIELD OF THE DISCLOSURE

The present disclosure relates generally to a detection or sensing of an animal or human tissue type, and more specifically, to exemplary embodiments of exemplary apparatus, devices and systems, which can be integrated into one or more insertion devices (e.g., including but not limited to a needle, cannula, etc.), for determining a tissue or fluid type prior to (i) an injection of any substance or material (e.g., drugs, biologics, filler, therapeutics, cellular materials, cells, genetic materials, stem cells, immunotherapy agents, etc.) and/or (i) an aspiration of fluids or collection of materials or tissue (e.g., core biopsy) from a body via such insertion apparatus, and to exemplary methods for manufacturing such insertion apparatus and/or sensing or determining the tissue type upon the insertion thereof. The present disclosure is also directed to exemplary embodiments of exemplary apparatus, devices and systems, which can be integrated into one or more insertion devices (e.g., including but not limited to an endoscope(s), catheter(s), laparoscope(s), etc.) via optical radiation transmitter(s) analysis, imaging, positioning and/or therapy of tissue using optical (e.g., including but not limited to light) radiation.

BACKGROUND INFORMATION

When performing surgery or procedure on a animal or human subject, or injecting any substance(s) and/or or material(s), including but not limited a pharmacological agents (e.g., a drug), filler substances, biological and non biological fillers, therapeutics, tissue or cellular material, stem cells, genetic materials, immunotherapy agents, etc. into an animal or human subject, it can be beneficial to inject the material into a particular tissue of the subject (e.g., certain blood vessels, fat, muscle, etc.) in some applications. It can also be important or beneficial to not inject the materials into certain tissue or lumen in the subject (e.g., certain blood vessels, etc.), in some applications, while being beneficial to inject such materials in such tissue or lumens in other applications. There are a number of commercially available non-invasive visualization systems (including ultrasound and optical visualization devices, etc.) to help identify and access specific structures such as veins or arteries (phlebotomy, IV, etc.). One example is the AccuVein which incorporates an infrared light source and detector which provide visualization of shallow veins. There are, however, no known technologies which are integrated with such access devices capable of specifically sensing or tissue changes or detecting blood vessels for the purpose of vessel targeting or avoidance.

Various non-insertion technologies exist for related applications, for example: (i) detecting blood vessels for the purpose of injection or blood collection, and (ii) detecting when a needle has penetrated a specific type of tissue (e.g., spinal space or other). However, there are no known insertion devices/arrangements that integrate sensing electrodes that facilitate rapid or real-time sensing/detection of different tissue types, while also facilitating an injection of substances or materials into a body and/or an aspiration of fluids or collection of material, cells or tissues from the body, such as, e.g., pharmacological agents, fillers, biologics, therapeutics, cellular materials, stem cells, genetic materials, immunotherapy agents, substances, etc., for example, with no manipulation of the insertion devices/arrangements.

One company, Injeq, created an IQ-Needle, which is a needle that uses electrical impedance spectroscopy to detect various tissue types, for example, to detect when the needle has penetrated spinal fluid. The needle incorporates two electrodes; one electrode is incorporated into a needle, and the other is incorporated into a stylet located inside the needle. After the target location has been detected, the stylet needs to be removed and then a syringe or other device must be connected to the needle before the procedure (e.g., injection or fluid collection) can begin. The IQ-Needle is shown and described in U.S. Patent Publication No. 2016/0029920, the entire disclosure of which is incorporated herein by reference in its entirety. Injeq has also developed a biopsy needle that uses the same approach. (See, e.g., U.S. Patent Publication No. 2018/0296197, the entire disclosure of which is incorporated herein by reference in its entirety).

Another prior system includes a sensing needle incorporating interdigitated, co-planar, electrodes on the surface for identifying different tissues using electrical impedance spectroscopy. The electrodes are deposited directly on the needle using conventional printed circuit board fabrication techniques. In such system, however, the needle is closed. Thus, the needle can only be used for sensing, and not for injecting an agent into a subject. Additionally, the needle is tethered to an analyzer used to determine the tissue type. Finally, since the electrodes are on the outer circumferential surface of the needle, the electrodes are not co-located with the tip. Therefore, the measurements from the electrodes do not reflect the conditions at the tip.

Additionally, many minimally invasive procedures involve devices, such as needles or catheters, which use external imaging to guide devices within the body. Imaging techniques include ultrasound, X-rays, magnetic resonance imaging (MRI), etc. Ultrasound imaging has been shown to be an effective guidance technology, although it provides only a two-dimensional (2D) image with limited information and somewhat poor needle visualization (See, e.g., Rocha et al., "Step-by-step of ultrasound-guided core-needle biopsy of the breast: review and technique," Radiol Bras. 2013 July/Ago; Vol. 46(4), pages 234-241). Further, X-ray or computerized tomography (CT) scans expose both the clinician and the subject to unwanted radiation. Thus, X-ray, CT, and MRI equipment is typically centralized with scheduling limitations. It is indeed difficult to provide a three-dimensional (3D) location of the tissue using the existing technology, and also limiting the negative effects of the devices that are needed to obtain the location.

Additionally, MRI, x-rays, ultrasound, and optics have all found important roles in imaging applications. In many applications optical radiation to effectuate imaging, analysis, therapy and other applications can offers certain advantages over other approaches because it is non-ionizing, non-contact, and can achieve high resolution. There are a variety of types of optical techniques, which utilize optical (e.g., light) radiation delivery, that are currently available include, e.g., optical coherence tomography (OCT) and other interferometric imaging techniques.

Optical (e.g., light) radiation delivery inside the body can be performed using discrete fibers which can be integrated into a medical insertion device, such as a catheter. These exemplary applications can include intravascular OCT (as described in, e.g., Bouma et al., "Intravascular optical coherence tomography," Biomedical Optics Express 2660, Vol. 8, No. 5, May 1, 2017), optical spectroscopy (as described in, e.g., Utzinger et al., "Fiber Optic Probes For Biomedical Optical Spectroscopy," J. of Biomedical Optics, 8(1), (2003)), and cardiac ablation (as described in, e.g., Dukkipati et al., "Pulmonary Vein Isolation Using The Visually Guided Laser Balloon: A Prospective, Multicenter, And Randomized Comparison To Standard Radiofrequency Ablation," JACC, 66(12):1350-60 (2015)). Other exemplary techniques include, e.g., and other spectroscopic imaging techniques, Raman imaging, diffuse-wave optical imaging, and two-photon imaging techniques. OCT is an interferometric imaging technology and thus has the properties of very high sensitivity and large dynamic range. OCT achieves depth resolution via a combination of the focal properties of the imaging optics used and the coherence properties of the optical source used.

Additionally, many minimally invasive procedures involve devices, such as needles or catheters, which use external imaging to guide devices within the body. Imaging techniques include ultrasound, X-rays, magnetic resonance imaging (MRI), etc. Ultrasound imaging has been shown to be an effective guidance technology, although it provides only a two-dimensional (2D) image with limited information and somewhat poor needle visualization (See, e.g., Rocha et al., Rafael Dahmer, Pinto, Renata Reis, Tavares, Diogo Paes Barreto Aquino, Gonsalves, Claudia Sofia Aires, "Step-by-step of ultrasound-guided core-needle biopsy of the breast: review and technique," Radiol Bras. 2013 July/Ago; 46(4): 234-241). Further, X-ray or computerized tomography (CT) scans expose both the clinician and the patient to unwanted radiation. Thus, X-ray, CT, and MRI equipment is typically centralized with scheduling limitations. It is indeed difficult to provide a three-dimensional (3D) location of the tissue using the existing technology, and also limiting the negative effects of the devices that are needed to obtain the location.

Further, the configurations and components of the catheters which utilize such optical modalities, including OCT, CT, MRI, fluorescence imaging Raman, optical imaging, etc. can be complex and costly. Various medical procedures which utilize catheters require multiple exchanges of devices for and in the catheter, in which a guide wire or guide sheath are introduced into the catheter first, and then ancillary tools, for example, a transseptal needle, can be inserted over or within the wire/sheath. These tools are then generally removed and exchanged for analysis and/or treatment tools, and/or entirely by sensing/treatment catheters.

Such exchange of components and/or tools can be length, and may affect the medical procedure when the timing of the use of the catheter and/or tools thereof can be important, and sometimes even crucial.

Thus, it may be beneficial to provide exemplary apparatus, devices and systems, which can be integrated into a one or more insertion devices (e.g., including but not limited to one or more needles, cannulas, catheters, etc.) for:

- determining a tissue type prior to and/or during (i) an injection of any substance or material (e.g., such as, e.g., pharmacological agents, biologics, fillers, therapeutics, cellular materials, stem cells, genetic materials, immunotherapy agents, substances, etc.) and/or (ii) an aspiration of fluids, substances, materials, cells, or tissues from a body via such insertion apparatus, and to exemplary methods for manufacturing such insertion apparatus and/or determining the tissue type upon the insertion thereof,
- determining and/or inferring a position of a tip of an insertion apparatus/device in three-dimensional space, e.g., using some of the same components which can be used for the used for the tissue type determination,
- providing optical radiation to the tissue, e.g., so as to determine the tissue type and/or the position of the tip, and/or
- ablating or otherwise effecting the tissue using components of the insertion device(s), which can be based on the determination of the tissue type and/or the position of the tip.

which can overcome at least some of the deficiencies described herein above.

SUMMARY

To that end, such exemplary apparatus, devices and systems can be provided according to exemplary embodiments of the present disclosure which can include and/or utilize an insertion device/apparatus. Further, additional exemplary apparatus, devices and systems can be provided according to exemplary embodiments of the present disclosure which can include and/or utilize optical transmitter(s), including but not limited optical waveguide(s).

To that end, an exemplary insertion apparatus/device according to an exemplary embodiment of the present disclosure can include, for example, a first electrically conductive layer at least partially (e.g. circumferentially) surrounding a lumen, an insulating layer at least partially (e.g. circumferentially) surrounding the first electrically conductive layer, and a second electrically conductive layer at least partially (e.g. circumferentially) surrounding the insulating layer, where the insulating layer can electrically isolate the first electrically conductive layer from the second electrically conductive layer. A further insulating layer can be included which can at least partially (e.g. circumferentially) surrounding the second electrically conductive layer. The first electrically conductive layer, the insulating layer, and the second electrically conductive layer can form a structure which has a first side and a second side disposed opposite to the first side with respect to the lumen, where the first side can be longer than the second side thereby forming a sharp pointed end via the first side at a distal-most portion of the insertion apparatus/device. The first electrically conductive layer, the insulating layer, and the second electrically conductive layer can form a structure that can be beveled to form a sharp pointed end at a distal-most portion of the insertion apparatus/device.

In some exemplary embodiments of the present disclosure, the first electrically conductive layer, the insulating layer, and the second electrically conductive layer can form a shaft of the insertion apparatus/device. The first electrically conductive layer, the insulating layer, and the second electrically conductive layer can form a structure that can extend distally from a hub. A barrel can be connected to the hub and a plunger can be configured to be inserted into the barrel. The first electrically conductive layer can be configured to transmit and/or receive an electrical signal (e.g., a first electrical signal), and the second electrically conductive layer can be configured to transmit and/or receive the same or different electrical signal (e.g., the first and/or the second electrical signal), and a communication device(s) can be configured to transmit information related to the electrical signal(s). The communication device(s) can be embedded in one of (i) a hub of the insertion apparatus/device, or (ii) a barrel of the insertion apparatus/device.

In certain exemplary embodiments of the present disclosure, the first electrically conductive layer can be configured to transmit and/or receive the electrical signal (e.g., a first electrical signal), and the second electrically conductive layer can be configured to transmit and/or receive the same or different electrical signal (e.g., the first or the second electrical signal), and a hardware processing arrangement can be configured to receive information related to the electrical signal(s), determine an impedance based on the information, and determine a tissue or fluid type based on the impedance. An audible arrangement can be configured to emit a sound based on the determined tissue or fluid type. The audible arrangement may be augmented or replaced by a visual arrangement to display a light or alphanumeric output based on the determined tissue or fluid type. The processing arrangement can be embedded in (i) a hub of the insertion apparatus/device, and/or (ii) a barrel of the insertion apparatus/device. Alternatively, the processing arrangement may be removably detachable from the hub or barrel. The lumen can be configured to (i) have a pharmacological agent injected therethrough, or (ii) have a biopsy sample obtained therethrough.

In another exemplary aspect of the present disclosure, the insertion apparatus/device can include a needle device, a cannula and/or other insertion configuration which has the first electrically conductive layer, the lumen, the insulating layer and the second electrically conductive layer.

According to still another exemplary embodiment of the present disclosure, an exemplary insertion apparatus/device can be provided which includes, for example, a hub and a shaft extending from the hub and surrounding a lumen, where the shaft can include an outer surface having an electrode(s) formed thereon or therein. A barrel can be connected to the hub and a plunger can be configured to be inserted into the barrel. A communication device(s) can be embedded in at least one of (i) the hub, (ii) the barrel, or (iii) a separate package which is mechanically and electrically connected to the hub or barrel. The electrode(s) can be configured to obtain an electrical signal, and a hardware processing arrangement can be embedded in (i) the hub, (ii) the barrel, or (iii) a separate package which is mechanically and electrically connected to the hub or barrel, where the hardware processing arrangement can be configured to receive information related to the electrical signal, determine an impedance based on the information, and determine a tissue type based on the impedance. The shaft can includes an insulating layer at least partially (e.g., circumferentially) surrounded by the outer surface and an electrically conductive layer at least partially (e.g., circumferentially) surrounded by the insulating layer, where the electrically conductive layer can form a further electrode. The electrode(s) can be integrated into the shaft.

Further, an exemplary insertion apparatus/device can include, for example, a hub and a shaft surrounding a lumen, where the shaft can include at least two non-removable electrodes. A processing arrangement can be configured to receive information related to (i) a first electrical signal obtained using a first one of the at least two non-removable electrodes and (ii) a second electrical signal obtained using a second one of the at least two non-removable electrodes, determine an impedance based on the information, and determine a tissue type based on the impedance.

According to still another exemplary aspect of the present disclosure, the insertion apparatus/device can include a needle device, a cannula and/or other insertion configuration which include(s) the hub and the barrel.

An exemplary method of determining a type of a tissue(s) of a subject(s) using an insertion apparatus/device can be provided. For example, according to such exemplary method, it is possible to, for example, receive a first electrical signal using a first electrically conductive layer that at least partially (e.g. circumferentially) surrounds a lumen of the needle, receive a second electrical signal using a second electrically conductive layer that at least partially (e.g. circumferentially) surrounds the first electrically conductive layer, determine an impedance based on the first and second electrical signals, and determine the type based on the impedance, e.g., by comparing a magnitude of the impedance or a phase of the impedance with predetermined values at one or more frequencies. The first electrically conductive layer can be isolated from the second electrically conductive layer using an insulating layer(s). Substances or materials into a body and/or an aspiration of fluids from the body, such as, e.g., pharmacological agents, biologics, fillers, therapeutics, cellular materials, stem cells, genetic materials, immunotherapy agents, etc. can be administered to the subject(s) through the lumen or a biopsy sample and/or any other substance of fluid can be obtained or removed from the subject(s) through the lumen.

Additionally, an exemplary method for determining a type of a tissue(s) of a subject(s) using an insertion device/apparatus can be provided. With such exemplary method, it is possible to, for example, receive an electrical signal(s) using an electrode(s) formed on or in an outer surface of a shaft of the insertion device/apparatus, determine an impedance based on the at least one electrical signal, and determine the type based on the impedance by comparing a magnitude of the impedance or a phase of the impedance with predetermined values at one or more frequencies. Substances or materials, such as pharmacological agents, biologics, fillers, therapeutics, cellular materials, stem cells, genetic materials, immunotherapy agents, substances, etc. can be administered to the subject(s) through the lumen of the insertion device/apparatus when a particular type is determined as being reached by a particular portion of the insertion device/apparatus or a biopsy sample can be obtained from the subject(s) through the lumen based on the determination. Alternatively and/or in addition, it is possible to aspirate fluid or other material from the sample using the determination of the type of the tissue reached by a particular portion of the insertion device/apparatus.

Further, an exemplary method of determining a type of a tissue(s) of a subject(s) using an insertion device/apparatus can be provided. With such exemplary method, it is possible to, for example, receive at least two electrical signals using at least two non-removable electrodes integrated into the insertion device/apparatus, determine an impedance based on the at least two electrical signals, and determine the type based on the impedance by comparing a magnitude of the impedance or a phase of the impedance with predetermined values at one or more frequencies. Substances or materials, such as, e.g., pharmacological agents, fillers, biologics, therapeutics, cellular materials, stem cells, genetic materials, immunotherapy agents, etc. can be administered to the subject(s) through the lumen of the insertion device/apparatus when a particular type is determined as being reached by a particular portion of the insertion device/apparatus or a biopsy sample can be obtained from the subject(s) through the lumen based on such determination. Alternatively and/or in addition, it is possible to aspirate fluid or other material from the sample using the determination of the type of the tissue reached by a particular portion of the insertion device/apparatus.

An exemplary tissue and/or fluid detection apparatus can include, for example, an insertion device/apparatus (e.g., which can be a needle device, a cannula and/or other insertion configuration) that can be configured inject substances or materials, such as, e.g., pharmacological agents, biologics, fillers, therapeutics, cellular materials, stem cells, genetic materials, immunotherapy agents, substances, etc. into a subject and/or remove a biopsy sample and/or other fluid, tissue, cells or material from the subject. The needle can be used to receive one or more electrical signals, which can be used to determine an impedance. The exemplary insertion device/apparatus can include a first electrically conductive layer at least partially (e.g. circumferentially) surrounding a lumen, an insulating layer at least partially (e.g. circumferentially) surrounding the first electrically conductive layer, and a second electrically conductive layer at least partially (e.g. circumferentially) surrounding the insulating layer, where the insulating layer can electrically isolate the first electrically conductive layer from the second electrically conductive layer. A further insulating layer can be included which can at least partially (e.g. circumferentially) surrounding the second electrically conductive layer.

In some exemplary embodiments of the present disclosure, the exemplary insertion device/apparatus can include a hub and a shaft extending from the hub and surrounding a lumen, where the shaft can include an outer surface having an electrode(s) formed thereon or therein. In certain exemplary embodiments of the present disclosure, the exemplary needle can include a hub and a shaft surrounding a lumen, where the shaft can include at least two non-removable electrodes. A communication device can be used to transfer/transmit information (e.g., wired or wirelessly) related to the electrical signals to a computer processing device. The processing device, which can be a mobile apparatus (e.g., phone, tablet, etc.), can be used to determine the impedance based on the electrical signals, and can also sense changes in the tissues and/or determine a tissue or fluid type based on the impedance.

As described above, the exemplary tissue detection and/or position indication system/apparatus can include a single insertion device/apparatus (e.g., needle, cannula, etc.). However, the exemplary tissue detection and/or position indication system/apparatus can include a plurality of such devices/apparatuses (e.g., needles, cannula, etc., and/or any combination thereof). Each tissue detection system/apparatus in the array thereof s can have, the same or similar electrode design/structure (e.g., same or similar design of the various exemplary electrode designs/structures described herein). Alternatively or in addition, each tissue detection and/or position indication system/apparatus in the array can have a different design/structure, or a subset of the needles can have one design/structure while another subset can have a different design/structure. Each tissue detection and/or position indication system/apparatus in the exemplary array of needles can perform the exemplary tissue detection as described herein, and each tissue detection system/apparatus can also perform a further function of, e.g., the administering of substances or materials, such as, e.g., pharmacological agents, biologics, fillers, therapeutics, cellular materials, stem cells, genetic materials, immunotherapy agents, etc. to the subject and/or the removal of a biopsy sample and/or other materials or fluid from the subject (all at the specific tissue based on the determination of a particular tissue of the subject. Thus, one or more of such insertion devices in the exemplary array thereof can perform the tissue detection, while one or more other needles can perform the injection or aspiration functions.

The exemplary array of the insertion devices can also be used to increase the accuracy of the tissue detection and/or position indication by increasing the number of the electrodes that are used to determine the impedance. Additionally or alternatively, a comparison of the impedance between insertion devices in the array can also be used to determine the tissue type. According to another exemplary embodiment of the present disclosure, a method can be provided for determining a type of at least one tissue of at least one subject or if an orifice of the tissue has been reached using an insertion arrangement (e.g., a needle arrangement). For example, it is possible to (i) insert the insertion arrangement into at least one portion of the subject to reach the tissue; (ii) receive a first electrical signal using a first electrically conductive layer that at least partially surrounds (e.g., circumferentially) a lumen of the insertion arrangement; (iii) receive a second electrical signal using a second electrically conductive layer that at least partially surrounds (e.g., circumferentially) the first electrically conductive layer; (iv) determine an impedance based on the first and second electrical signals; and (v) determine whether the type or the orifice of the at least one tissue has been reached based on the impedance by comparing at least one of a magnitude of the impedance or a phase of the impedance with predetermined values at one or more frequencies. It is also possible to electrically isolate the first electrically conductive layer from the second electrically conductive layer using at least one insulating layer. Further, it is possible to (i) administer a pharmacological agent to the subject through the lumen, and/or (ii) obtain a biopsy sample from the at least one subject through the lumen.

According to another exemplary embodiment of the present disclosure a similar method can be provided for determining a type of at least one tissue of at least one subject or if an orifice of the tissue has been reached using an insertion arrangement. For example, it is possible to (i) insert the insertion arrangement into at least one portion of the at least one subject to reach the tissue; (ii) receive at least one electrical signal using at least one electrode formed on or in an outer surface of a shaft of the insertion arrangement; (iii) determine an impedance based on the at least one electrical signal; and (iv) determine whether the type or the orifice of the at least one tissue has been reached based on the impedance by comparing at least one of a magnitude of the impedance or a phase of the impedance with predetermined values at one or more frequencies. It is further possible to (i) administer a substance, material or pharmacological agent to the at least one subject through a lumen of the needle or cannula, and/or (ii) obtain a biopsy sample from the at least one subject through the lumen.

According to a still exemplary embodiment of the present disclosure, a method can be provided for determining a type of at least one tissue of at least one subject or if an orifice of the tissue has been reached using an insertion arrangement (e.g., a needle arrangement). With the exemplary method, it is possible to (i) insert the insertion arrangement into at least one portion of the subject to reach the tissue; (ii) receive at least one electrical signal (e.g., and possible at least two electrical signals) using at least two non-removable electrodes integrated into the insertion arrangement; (iii) determine an impedance based on the electrical signal(s); and (iv) determining whether the type or the orifice of the tissue has been reached based on the impedance by comparing at least one of a magnitude or a phase of the impedance with at least one predetermined value of at least one frequency. Similarly to the previously-described exemplary embodiments, it is further possible to (i) administer a pharmacological agent to the subject through a lumen of the insertion arrangement, and/or (ii) obtain a biopsy sample from the subject through the lumen.

All of the above-described exemplary embodiments can be utilized to, e.g., (i) deliver a composition into the tissue of the subject or an orifice of the tissue, and/or (ii) extract material or a fluid from at least one tissue of at least one subject or an orifice of the at least one tissue using an insertion device, e.g., at a particular location of the tissue corresponding a type of the tissue.

Further, an exemplary insertion apparatus/device according to an exemplary embodiment of the present disclosure can include, a base structure comprising at least one lumen (or a plurality of lumens) extending along a length thereof, and at least one optically-transmissive layer circumferentially surrounding the base structure and provided at least at a distal end of the base structure. For example, in operation, the optically-transmissive layer can be configured to transmit a particular optical radiation at the distal end thereof toward a target tissue.

Further, a cladding layer can be included which can at least partially (e.g. circumferentially) surrounding the second electrically conductive layer. The first electrically conductive layer, the insulating layer, and the second electrically conductive layer can form a structure which has a first side and a second side disposed opposite to the first side with respect to the lumen, where the first side can be longer than the second side thereby forming a sharp pointed end via the first side at a distal-most portion of the insertion apparatus/device. The first electrically conductive layer, the insulating layer, and the second electrically conductive layer can form a structure that can be beveled to form a sharp pointed end at a distal-most portion of the insertion apparatus/device provided between the optically-transmissive layer and the base structure. The cladding layer can have an optical index that is different from an optical index of the optically-transmissive layer. Further, the optically-transmissive layer can be configured to transmit the optical radiation in a first direction, and the cladding layer can be configured to transmit a further optical radiation in a second direction which is opposite to the first direction.

According to another exemplary embodiment of the present disclosure, the cladding layer can be configured to transmit a further optical radiation from the tissue, and the further optical radiation can be based on the particular optical radiation.

In another exemplary embodiment of the present disclosure, a further cladding layer can be provided that circumferentially surrounds the optically-transmissive layer. At least one further optically-transmissive layer can be include that circumferentially surrounds the further cladding layer. The optically-transmissive layer and the further optically-transmissive layer can be configured to transmit the particular optical radiation in a first direction, and the cladding layer and the further cladding layer can be configured to transmit a further optical radiation in a second direction which is opposite to the first direction. The cladding layer and the further cladding layer can be configured to transmit the further optical radiation from the tissue, and the further optical radiation can be based on the particular optical radiation.

According to a further exemplary embodiment of the present disclosure, the optically-transmissive layer can include a plurality of core sections which are optically separated from one another. For example, one of the core sections can be configured to transceive at least one first portion of the particular optical radiation, and another one of the core sections can be configured to transceive at least one second portion of the particular optical radiation. The first and second portions can be optically separated from one another. A cladding layer can be provided between the optically-transmissive layer and the base structure. For example, one of the core sections can be optically and physically separated from another one of the core sections by at least one cladding section of the cladding layer. At least one of the core sections can be configured to transceive at least one first portion of the particular optical radiation at least one first portion of the particular optical radiation, and the cladding section can be configured to transceive at least one second portion of the particular optical radiation. The first and second portions can be optically separated from one another.

In yet another exemplary embodiment of the present disclosure, an optical multiplexer can be provided that is configured to multiplex the particular optical radiation provided to the tissue and a return optical radiation provided from the tissue which is associated with the particular optical radiation. A hardware processing arrangement can be provided which can be configured to (i) receive information related to the return optical radiation, and (ii) determine data, based on the information. Such data can be, e.g., (i) at least one characteristic of the tissue, (ii) at least one location of a target area of the tissue, and/or (iii) a location of a tip of the base structure with respect to the tissue. At least one audible arrangement can be provided which is configured to emit a sound based on the data. Alternatively or in addition, it is possible to provide a visual indicator (e.g., LED, lamp, display, etc.) to generate an image or provide information based on the data.

According to a further exemplary embodiment of the present disclosure, the base structure can include at least one lumen extending there through that is configured to have a pharmacological agent injected there through. Examples include can photosentizers, such as, e.g., porfimer sodium which can be delivered locally through the lumen and then activated with light delivered through the optically transmissive layer. This can minimize exposure of tissues other than those targeted by the photodynamic therapy. Potential applications include oncology and improved implant patency. Alternatively or additionally, the at least one lumen can be used have a biopsy sample obtained there through. The optically-transmissive layer can includes at least one helical-patterned structure which define an outer patterned section of the insertion apparatus. A computer hardware arrangement can be provided which can be configured to determine a three-dimensional location of at least one portion of the insertion apparatus based on information received by the computer hardware arrangement from the optically-transmissive layer which is associated with a return optical radiation provided from the tissue which is based on a particular optical radiation. In another exemplary embodiment of the present disclosure, a method can be provided for determining information associated with at least one tissue of at least one patient or if an orifice of the at least one tissue has been reached using an insertion apparatus/arrangement. Using such exemplary method, it is possible to (i) insert the insertion apparatus/arrangement into at least one portion of the patient to reach the tissue, (ii) transmit a first optical radiation using (a) at least one optically-transmissive layer that circumferentially surrounds a base structure or a cladding layer, or (b) the cladding layer, (iii) receive a second optical radiation via at least another one of (a) the optically-transmissive layer, and/or (b) the cladding layer based on the first optical radiation, and determining data, based on the second optical radiation, which can be (a) at least one characteristic of the tissue, (b) at least one location of a target area of the tissue, and/or (iii) a location of a tip of the base structure with respect to the tissue.

For example, it is also possible, to (i) administer a pharmacological agent to the patient through a lumen of the base structure, and/or (ii) obtaining a biopsy sample from the patient through the lumen. It is further possible to, based on the data, ablate an area of the at least one tissue by applying a further optical radiation to the tissue, which can utilize, e.g., a Photodynamic Therapy (PDT). It is yet further possible to determine a three-dimensional location of at least one portion of the insertion apparatus at or in a body based on the data. It is additionally possible to generate an image on a display of at least one portion of the insertion apparatus at or in a body in a three-dimensional space based on the data.

In another exemplary embodiment, the structure such as, e.g., a catheter or needle can be used to reduce and/or stop blood flow or stabilize abnormal tissues such as, e.g., fibroids, tumors, and aneurisms through photopolymerization. The structure can, e.g., a) be guided through a blood vessel to the target area such as a uterine fibroid, b) deliver a monomer such as poly(ethylene glycol) diacrylate mixed with a photoinitator such as 1-[4-(2-hydroxyethoxy)-phenyl]-2-hydroxy-2-methyl-1-propane-1-one (α-HAP) through one or more lumens, and then c) cross-link the material in-situ by exposing the material to UV-A light delivered through the optically transmissive layer.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1A:
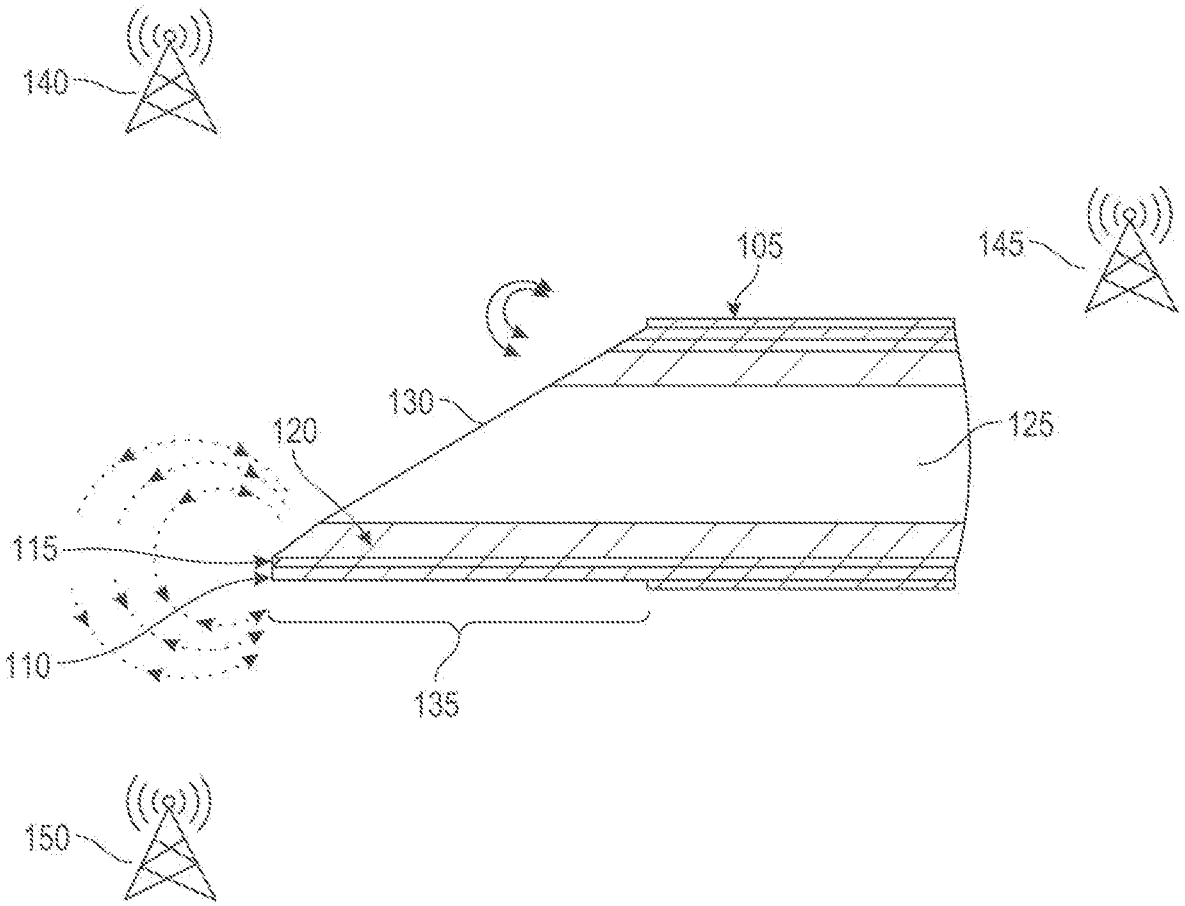
FIG. 1A is an exemplary diagram of a close-up cross-sectional view of a distal end of an exemplary insertion device/apparatus (e.g., a needle) which illustrates the ability of the device/apparatus to sense at the leading edge or tip according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION

The exemplary embodiments of the present disclosure may be further understood with reference to the following description and the related appended drawings. In particular, the exemplary embodiments of the present disclosure relate to at least one insertion device/apparatus (which can be an array thereof) for use in determining a tissue or fluid type. Such determination can be made prior to the injection of a drug. Tissue type can include, but is not limited to, dermis, fat, muscle, skin, bone, nerves, muscle, eye tissue, organ tissue, teeth, etc. Fluids include blood, synovial fluid, lymph fluid, etc. The exemplary embodiments are described with reference to an exemplary insertion device/apparatus, it should be abundantly clear the exemplary embodiments of the present disclosure may be implemented on other insertion and/or injection devices for use in injecting substances into the body of a subject and/or removing substances and/or materials therefrom, including but not limited cannulas, catheters, etc. As used herein, the exemplary insertion device/apparatus can be used on a person (e.g., a human). However, the exemplary insertion device/apparatus can also be used for other subjects including, but not limited to, animals, or other various species.

In still a further exemplary embodiment of the present disclosure, the exemplary insertion device/apparatus can be used to determine or infer a position of a tip thereof in three-dimensional space, e.g., using some of the same components used for the used for the tissue detection.

It should also be understood that any reference to a needle, needle apparatus, etc. according to various exemplary embodiments of the present disclosure described herein also includes, and equally applicable to, other insertion devices for providing and/or extracting substances and/or materials to and from a body, including but not limited to cannulas, endoscopes, laparoscopes, etc.

The exemplary apparatus can utilize, for example, electrical impedance to selectively determine when at least one insertion device (e.g., a needle) has been introduced into a specific type of tissue (such as a blood vessel—e.g., an artery or vein, or into a tissue such as, e.g., fat). The exemplary apparatus can operate utilizing an alternating voltage applied to two or more electrodes located on the apparatus, which can be used to measure the resulting current. Such impedance can be determined from, e.g., the ratio between the voltage and current, and can be, e.g., a complex number (e.g., includes real and imaginary components). The calculated electrical impedance can vary with the frequency and the tissue type. Various exemplary characteristics of the measured impedance (e.g., magnitude and angle as a function of frequency, etc.) can be used to determine tissue type. Such determination can be performed using the exemplary system, device and computer-accessible medium with the use of a processor executing a program that can utilize the information/data associated with the ratio of the voltage, current, etc. as well as other values and information.

In one exemplary embodiment of the present disclosure, the exemplary apparatus, devices and/or systems can be used to measure the impedance at the tip of an insertion device/apparatus (such as, e.g., needle, cannula, endoscope, laparoscope, a hypodermic needle, etc.), and can determine when the tip of the insertion device/apparatus is located within a specific type of tissue or orifice without any alteration to current clinical practice. In this exemplary manner, a medical professional can determine the location of the insertion device/apparatus (e.g., the tissue type) prior to injecting an agent into the subject. Once the correct tissue type for depositing the agent has been determined, the medical professional can introduce (e.g., inject) the agent into the subject. No stylet or other component is needed in order to determine the tissue type. Additionally, the exemplary apparatus can provide an audible, tactile and/or visual alert based on the tissue type.

The exemplary apparatus can include, or can be connected to, for example, a display screen which can intermittently or continuously provide the medical professional or any person inserting the exemplary insertion device/apparatus the information regarding the determined tissue or fluid type based on the determined electrical impedance. For example, when the medical professional first introduces the insertion device/apparatus into the subject, the display can indicate the first tissue or fluid type the insertion device/apparatus is inserted into. As the medical professional pushes the insertion device/apparatus further into the subject, the display device can change as the tissue or fluid type changes. Such change can include providing different colors, shapes, visual indicators, etc. Once the correct or specific tissue or fluid type has been determined as being reached (e.g., based on a visual indication to the medical professional), the medical professional can cease pushing the insertion device/apparatus, and inject any material or substance into the subject at the location of the tip of the insertion device/apparatus, and/or extract any material or substance therefrom. Alternatively, or in addition, the exemplary apparatus can be programmed based on a particular impedance value or tissue or fluid type (e.g., a tissue or fluid type selected by the medical professional to inject the agent into), and an audible alert can sound once the exemplary apparatus has determined the selected impedance value or tissue or fluid type. The audible or light indicator alert can also be programmed to provide a variable tone or light to represent passage through various tissues or fluids, for example, with a frequency that varies with impedance. Through the present disclosure, the terms materials and/or substance are understood to include a pharmacological agent (e.g., a drug), biologics, fillers, therapeutics, cellular materials, stem cells, genetic materials, immunotherapy agents, etc., but certainly not limited thereby.

For example, the exemplary apparatus, devices and systems can be used for immunotherapeutic applications including, but not limited to, the controlled subcutaneous delivery of allergens (e.g. food, mold, animal, dust mite and pollen allergens) to help reduce the allergic response of a subject to such allergens. Food allergies are an increasing global health concern and, in Europe alone, about 17 million people are affected; 3.5 million of which are under the age of 25. Food allergies can be life threatening resulting in over 300,000 ambulatory care visits of people under the age of 18 and 150 deaths due to anaphylactic shock per year. Current methods of allergen-related immunotherapy utilize the repetitive subcutaneous injection of small doses of allergen into a subject. A serious risk in current methods of allergen-related immunotherapy is accidental injection of the allergen dose into a blood vessel resulting in the systemic dispersal of the allergen. Such a systemic dispersal can cause a severe allergic reaction in the subject resulting in death from anaphylactic shock. By using the exemplary apparatus, devices and systems, blood vessels can be readily and easily detected and avoided, thereby decreasing or eliminating the risk of accidental injection of an allergen into a blood vessel.

The exemplary apparatus, devices and systems can include a fully open center lumen, which can facilitate the insertion device/apparatus to be used to deliver any material, substance and/or agent, as well as for, collection, or introduction of other devices (e.g., medical devices) through the lumen. Thus, the exemplary apparatus, devices and systems can be comparable to standard hypodermic needles which are generally characterized by their internal diameter. Further, the exemplary insertion device/apparatus can be fully integrated and tuned to sense specific tissues. For example, a particular insertion device/apparatus can be used for a particular tissue (e.g., the insertion device/apparatus can be tuned to specific frequencies to detect a single type of tissue by reviewing the magnitude and/or phase components of the impedance). The exemplary angle of the tip and/or the width of the insertion apparatus/device described for the exemplary embodiments can be provided and/or fabricated based on various different characteristics of the tissue into which the exemplary insertion device/apparatus is inserted. With respect to the tissue type determination, this can facilitate the electronics of the exemplary apparatus, devices and systems to determine the impedance to be simplified since the exemplary apparatus, devices and systems do not need to obtain a complete spectra, as the exemplary apparatus, devices and systems would only preferably obtain the spectra for the particular tissue type. The exemplary electrodes can be applied using a spray or deposition process, as discussed below. The resulting structure can then be used to produce the exemplary insertion device using conventional grinding and insertion device/apparatus fabrication processes. Additionally, the inner electrode can include the base body of the insertion device/apparatus itself. Two, three, or more electrodes can then be provided by applying additional layers to the insertion device/apparatus. As discussed herein, the exemplary angle of the tip and/or the width of the insertion apparatus/device described for the exemplary embodiments can be provided and/or fabricated based on various different characteristics of the tissue into which the exemplary insertion device/apparatus is inserted.

The exemplary apparatus can be used in the field of a filler injection, including but not limited to a facial filler injection, etc. For example, an injection of a filler into an artery can cause a partial or total vessel occlusion which can lead to tissue necrosis. (See e.g., Reference 6). To address this problem, an exemplary insertion and guidance device/apparatus according to an exemplary embodiment of the present disclosure can provide feedback to a clinician or a medical professional indicating that the tip or opening of such insertion device/apparatus is provided in a blood vessel. In this manner, the medical professional can avoid dispensing the filler into any blood vessel, including, e.g., artery, vein, capillary, etc. Then, occlusions created by certain materials and/or substance (e.g., fillers) injected into a blood vessel (e.g., an artery, a vein, etc.) can be cleared. Such materials and/or substances can include hyaluronic acid. Hyaluronidase is an enzyme that can be used to dissolves hyaluronic acid. Occlusions detected in a timely manner can be cleared by injecting hyaluronidase. An exemplary perfusion detection apparatus can provide an alert that there is an occlusion such that action can be taken before extensive cell death occurs.

For example, the exemplary fillers can include, but certainly not limited to, absorbable or temporary materials (e.g., Collagen, Hyaluronic acid, Calcium hydroxylapatite, Poly-L-lactic acid (PLLA)), non-absorbable or permanent materials (e.g., Polymethylmethacrylate beads (PMMA microspheres)), as well as other materials. Various FDA-approved fillers can be as follows: Restylane Lyft with Lidocaine, Revanesse Versa, Revanesse Versa+, Rha 2, Rha 3, Rha 4, Juvederm Vollure XC, Restylane, Refyne, Restylane Defyne, Juvederm Volbella XC\, Radiesse, Restylane Silk, etc.

In another exemplary embodiment of the present disclosure at least one insertion device/apparatus (which can be an array thereof) can be provided for use in delivering optical radiation to tissue and determining tissue characteristics and/or the effect of the optical radiation delivery on the impacted tissue and/or surrounding areas. The exemplary embodiments are described with reference to an exemplary insertion device/apparatus, and can include but not limited cannulas, catheters, laparoscopes, needles, etc. As used herein, the exemplary insertion device/apparatus can be used on a person (e.g., a human). However, the exemplary insertion device/apparatus can also be used for other subjects including, but not limited to, animals, or other various species.

According to a further exemplary embodiment of the present disclosure, the exemplary insertion device/apparatus can be used to apply an optical radiation (e.g., light, etc.) to the tissue that is of interest. Such application of optical radiation to specific tissues can be based on a tissue detection determination performed using same components of the exemplary insertion device/apparatus used for the radiation application.

In one exemplary embodiment of the present disclosure, the exemplary apparatus, devices and/or systems can be used to transmit optical radiation to the tissue at a tip of the insertion device/apparatus via an optical coating located thereon, and then receive a returning optical radiation from the tissue being impacted by such radiation to determine information regarding the tissue, e.g., at the tip of an insertion device/apparatus (such as, e.g., needle, cannula, endoscope, laparoscope, cannula, a hypodermic needle, etc.), and can determine when the tip of the insertion device/apparatus is located within a specific type of tissue or orifice without any alteration to current clinical practice. In this exemplary manner, a medical professional can determine the location of the insertion device/apparatus (e.g., the tissue type) prior to injecting an agent into the patient. Once the correct tissue type or location of the tissue for depositing the agent has been determined, the medical professional can introduce (e.g., inject) the agent into the patient. No stylet or other component is needed in order to determine the tissue type or location of the tissue. Additionally, the exemplary apparatus can provide an audible, tactile and/or visual alert based on the tissue type.

The exemplary apparatus can include, or can be connected to, for example, a display screen which can intermittently or continuously provide the medical professional or any person inserting the exemplary insertion device/apparatus the information regarding the determined tissue (or fluid) type or location of the tissue based on the information provided by the return optical radiation provided from the tissue. For example, when the medical professional first introduces the insertion device/apparatus into the patient, the display can indicate the first tissue type or location of the tissue that the insertion device/apparatus is inserted into. As the medical professional provides the insertion device/apparatus further into the patient, the display device can change as the tissue or fluid type or location of the tissue changes, e.g., providing information regarding the tissue characteristics at the tip of the insertion device/apparatus, illustrating the 360 degree view of the tissue at various locations in real time, etc. Such change can also include providing different colors, shapes, visual indicators, fly-through, etc. In one example, once the specific tissue-type or fluid-type or location of the tissue has been determined as being reached (e.g., based on a visual indication to the medical professional), the medical professional can cease pushing the insertion device/apparatus, and inject any material or substance into the patient at the location of the tip of the insertion device/apparatus, and/or extract any material or substance therefrom. Alternatively, or in addition, the exemplary apparatus can be programmed based on a particular issue or fluid-type type or location of the tissue (e.g., a tissue or fluid-type and/or tissue location selected by the medical professional to inject the agent into), and an audible alert can sound once the exemplary apparatus has determined the selected tissue and/or fluid-type. The audible or light indicator alert can also be programmed to provide a variable tone and/or light to represent passage through various tissues or fluids, for example, with a frequency that varies with impedance. Through the present disclosure, the terms materials and/or substance are understood to include a pharmacological agent (e.g., a drug), fillers, therapeutics, cellular materials, stem cells, genetic materials, immunotherapy agents, etc., but certainly not limited thereby.

According to yet another exemplary embodiment of the present disclosure, the exemplary apparatus can use the optical radiation returning from the tissue being impacted by the forwarded optical radiation to determine and/or infer a three-dimensional position of the tip of the exemplary apparatus. Such information can also be used for delivering an agent for treatment which is activated or otherwise effected by subsequent application of further optical radiation.

The exemplary apparatus, devices and systems can include a fully open center lumen, which can facilitate the insertion device/apparatus to be used to deliver any material, substance and/or agent, as well as for, collection, or introduction of other devices (e.g., medical devices) through the lumen. Thus, the exemplary apparatus, devices and systems can be comparable to standard hypodermic needles, endoscopes, laparoscopes, cannulas, etc. which are generally characterized by their internal diameter. Further, the exemplary insertion device/apparatus can be fully integrated and tuned to sense specific tissues and/or determine locations of the tissue. The exemplary angle of the tip and/or the width of the insertion apparatus/device described for the exemplary embodiments can be provided and/or fabricated based on various different characteristics of the tissue into which the exemplary insertion device/apparatus is inserted.

The exemplary optically-transmissive coating can be applied using a spray, sputtering, dipping, painting and/or deposition processes, as discussed below. Exemplary materials used for such application can include polymers such as, e.g., urethane, acrylic, polycarbonate, polystyrene, cyclic olefin polymers or copolymers, as well as copolymers combining materials. It is also possible to utilize silicones. Glass and/or ceramic coatings can be formed using a sol gel process with post-processing such as, e.g., sintering and/or by applying a material in powder form and then using a melt quenching process. Other exemplary materials can include, e.g., silica glass, aluminum oxide, etc. The selection of the exemplary materials that can be used for the application can be selected and/or defined by the process temperature and compatibility with the target structure. For example, a glass or a ceramic that prefers the use of the sintering procedure for the application of the coating may be difficult to apply to a polymer because the temperatures may be above the polymer glass transition temperatures. Thus, another exemplary material can be selected, according to the exemplary embodiment of the present disclosure.

According to further exemplary embodiments of the present disclosure, the resulting structure can then be used to produce the exemplary insertion device using conventional grinding and insertion device/apparatus fabrication processes. Additionally, the inner structure (e.g., a base structure) can include the base body of the insertion device/apparatus itself. The base structure can be made using similar coating application as discussed herein.

Such exemplary base structure can be separated from the optically-transmissive coating (e.g., which can be referred to as an optically-transmissive core) via an optical cladding. Cladding materials can include any material with a lower refractive index than the transmissive coating of the base structure and/or that of the core. Such exemplary materials include any of those described herein which have a slightly lower index than the coating of the base structure and/or the core. The cladding may also include reflective materials such as, e.g., a metallic coating.

According to still another exemplary embodiment of the present disclosure, selected areas on or in the insertion device/apparatus may be masked or otherwise separated during the application of the cladding to leave selected areas uncoated. The mask may be applied in a predetermined pattern or shape. The mask may be applied manually, e.g., by painting or printing on a substance that may be physically (peeling, scraping) or chemically removed after coating. The mask can also be applied and patterned using a photolithographic process.

According to a further exemplary embodiment of the present disclosure, two, three, or more combinations of optically-transmissive core/cladding can then be provided by applying additional layers to the insertion device/apparatus. Such exemplary multi-layer structure can be produced as discussed above, as well as using, e.g., a co-extrusion process. For example, one or more of the core/cladding combination(s) can be used to deliver optical radiation (e.g., light, etc.), and other one or more the core/cladding combination(s) can be used to collect optical radiation (e.g., light, etc.).

FIG. 1A shows an exemplary diagram of an exploded cross-sectional side view of a distal end of an exemplary insertion device/apparatus (e.g. needle) according to an exemplary embodiment of the present disclosure. As shown in FIG. 1A, the exemplary insertion device/apparatus can include a needle 105 incorporating two or more, non-planar, concentric conductive electrodes (e.g., electrodes 110 and 120). One of the electrodes (e.g., electrode 110), can be formed from a conductive coating on or in a surface of the insertion device/apparatus. The use of two or more, non-planar, concentric conductive electrodes can leave center lumen 125 open for delivery, collection, or introduction of fluids or other substances or devices. The exemplary insertion device/apparatus can be of any size as required to inject a pharmaceutical agent, or to introduce a minimally invasive device such as a guidewire or catheter through opening 130. The exemplary electrodes can have different forms and/or configurations. For example, a portion of the insertion device/apparatus itself (e.g., a portion of the surface of the insertion device/apparatus) can act as one of the electrodes. A second electrode can then be fabricated in-situ and/or pre-fabricated, and then placed on the surface of the insertion device/apparatus. The two electrodes can then be used to measure impedance at the tip of the insertion device/apparatus (e.g., for the determination of the tissue type as discussed herein).

As shown in FIG. 1A, center lumen 125 can be surrounded by electrode 120, which can form an internal portion and/or surface of the insertion device/apparatus itself. An insulative coating 115 (e.g., made of polyimide or any other suitable material, such as polyamide, for example) can surround electrode 120, e.g., outwardly radially. Electrode 110 can then be formed around on insulative coating 115. Thus, insulative coating 115 can be used to electrically isolate electrodes 110, 120 from one another. A second insulative coating, e.g., can surround electrode 110, to isolate electrode 110, except for, e.g., an uninsulated portion 135 of electrode 110.

Figure 1B:
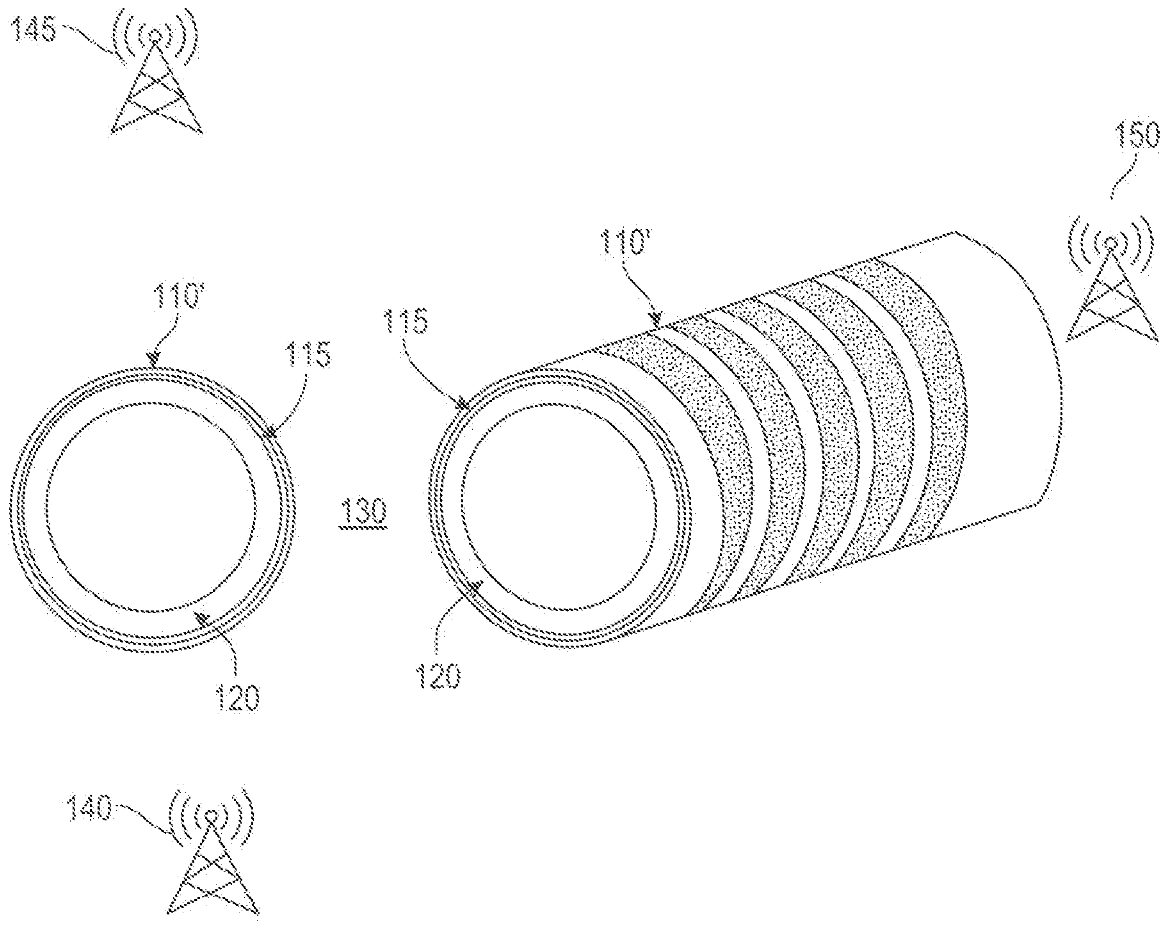
FIG. 1B are a set of exemplary diagrams of cut-away view and a close-up cross-sectional view of a distal end of an exemplary insertion device/apparatus according to another exemplary embodiment of the present disclosure.

According to another exemplary embodiment of the present disclosure, another exemplary insertion device/apparatus can be provided, as shown in FIG. 1B. Indeed, the same exemplary portions/components of the exemplary insertion device/apparatus illustrated in FIG. 1A are labeled with the same numerals in FIG. 1B. Similarly to the exemplary embodiment described herein that provides the three-dimensional location of the tip of the exemplary insertion device shown in FIG. 1A, the exemplary apparatus of FIG. 1B also can use alternating current applied to the exemplary electrodes to determine and/or infer a three-dimensional position of the tip of the exemplary apparatus. Nonetheless, instead of providing electrode 110 which circumferentially surrounds insulating layer 115, masking can be used to produce and/or provide helical-patterned and/or other exemplary patterned structures which define an outer conductive patterned layer 110'. Such exemplary use of the helical-patterned outer conductive layer can improve the transmission of the radiation and/or detection thereof by antennas 140, 145, 150 to facilitate an improved three-dimensional position detection of the tip of the exemplary insertion device. For example, referring again to FIG. 1B, alternating current can be transmitted via the conductive/electrical channels of the device (e.g., internal thereto and/or provided on a surface thereof) to reach helically-patterned outer conductive layer (e.g., electrode) 110' and/or inner conductive base (e.g., inner electrode) 120 so as to generate an electromagnetic field. Such electric field generated by patterned layer (e.g., concentric electrodes) 110' can be detected by antennas 140, 145, 150.

Figure 1C:
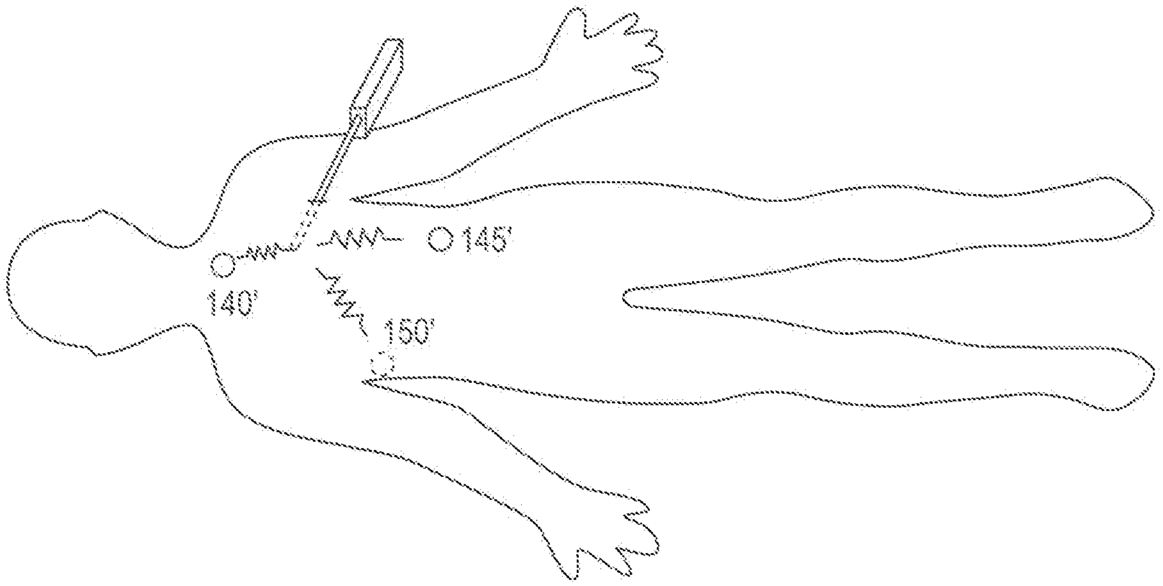
FIG. 1C is a top view of an exemplary application of the exemplary insertion device/apparatus provided on a body according to yet another exemplary embodiment of the present disclosure.

The exemplary insertion device/apparatus shown in FIG. 1B is illustrated in operation in FIG. 1C. In particular, exemplary concentric electrodes 110' illustrated in FIG. 1C facilitate locating the tip of the exemplary insertion device in a three-dimensional space, as discussed herein. This can be done by using, e.g., static current, alternating current and/or another energy or radiation which can include the determination of impedance at the tip. It is also possible to utilize a constant current with the exemplary electrodes 110, 110', and 120. For example, constant or alternating current can be applied and/or utilized. For example, the relative distance of the tip to antenna's 140, 145, and 150 can be measured due to the current emission. In addition or alternatively, it is possible to provide other surface electrodes 140', 145', 150' placed at different locations on the body to measure current and infer the effective resistance and relative position from the tip to each electrode, e.g., in a three-dimensional space. In addition and/or alternatively, these exemplary electrodes 140', 145', 150' placed at different locations on the body can be used to measure the magnitude of the current which can decrease as a function of distance and resistance/impedance. Thus, using such electrodes 140', 145', 150', it is possible to triangulate the position of the tip in the three-dimensional space.

Figure 1D:
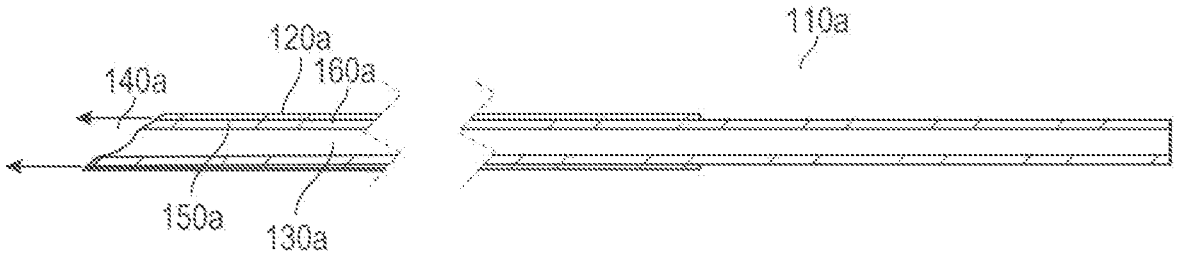
FIG. 1D is an exemplary diagram of a close-up cross-sectional view of a distal end of an exemplary insertion device/apparatus (e.g., needle, endoscope, cannula, etc.) according to an exemplary embodiment of the present disclosure which includes an optically-transmissive coating provided on a surface a base structure of the exemplary insertion device/apparatus.

Turning to another exemplary embodiment of the present disclosure, FIG. 1D shows an exemplary diagram of an exploded cross-sectional side view of a distal end of an exemplary insertion device/apparatus (e.g. needle, endoscope, laparoscope, cannula, etc.) 110*a* according to an exemplary embodiment of the present disclosure. As shown in FIG. 1D, the exemplary insertion device/apparatus 110*a* can include an optically-transmissive coating 120*a* which surrounds at least one portion of the insertion device/apparatus 110*a*, e.g., in a location closer to a tip thereof. For example, such coating 120*a* can be provided/formed/deposited on an external portion of the insertion device/apparatus 110*a*, which forms a waveguide for the optical radiation. Thus, the coating 120*a* can also be referred to as an optical core and/or the waveguide which is configured to transmit and/or receive optical radiation, e.g., light, etc. to and from tissue. A surface 150*a* of a base structure 150*a* of the insertion device/apparatus 110*a* on which the coating 120*a* is provided/formed/deposited has a lower refractive index than the optically-transmissive coating 120*a*, such that the optical radiation is directed along the coating 120*a* toward the tissue of interest.

The insertion device/apparatus 110*a* also includes a center lumen 130*a* open for delivery, collection, or introduction of fluids or other substances or devices. The center lumen is enclosed and/or defined by an inner surface of the base structure of the insertion device/apparatus 110*a*. Thus, as shown in FIG. 1D, center lumen 130*a* can be surrounded by the base structure 160*a*, which can form an internal portion and/or surface of the insertion device/apparatus 110*a* itself.

In one exemplary embodiment, the exemplary insertion device/apparatus 110*a* can be of any size as required to inject a pharmaceutical agent, or to introduce a minimally invasive device such as a guidewire or catheter through the lumen 130*a*.

Figure 1E:
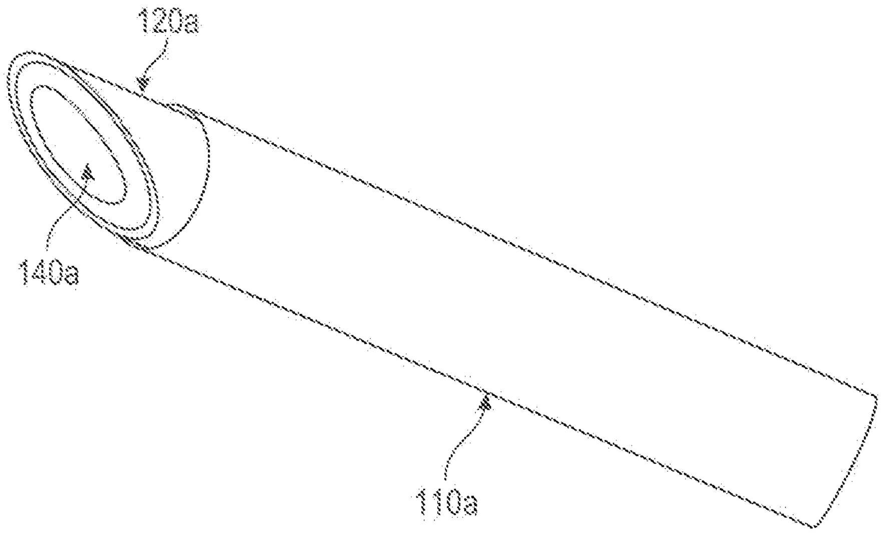
FIG. 1E a close-up perspective view of a distal end of the exemplary insertion device/apparatus according to another exemplary embodiment of the present disclosure shown in FIG. 1D.

FIG. 1E shows a further perspective view of an exemplary diagram of a distal end of the exemplary insertion device/apparatus 110*a* according to an exemplary embodiment of the present disclosure of FIG. 1D. As shown in FIGS. 1D and 1E, the exemplary insertion device/apparatus 110*a* with the base structure 160*a* is provided internally and surrounded by the optically-transmissive coating 120*a*, which can be provided using, e.g., sequential spray processes (e.g., as described herein) to provide—internally to exemplary insertion device/apparatus 110*a*, the cladding enclosed by the core.

In still another exemplary embodiment of the present disclosure, the exemplary apparatus can use the optical radiation (e.g., light) provided and/or returned from the sample to determine and/or infer a three-dimensional position of the tip of the exemplary apparatus with respect to the tissue. For example, referring again to FIGS. 1A-1E, optical radiation can be transmitted via the core of the insertion device (e.g., provided along a surface thereof) to impact the tissue with such optical radiation. The optical radiation can impact the tissue, and a responsive optical radiation can be provided from the tissue which can then be transmitted along the same coating 120*a* (e.g., the core) as the insertion device/apparatus 110/110*a* is being translated, thereby providing signals which then converted to data to provide, e.g., data and/or a visualization of the tissue surrounding the insertion device/apparatus 110/110*a* at a tip of thereof while it is being moved laterally through the body (e.g., through an orifice, via a tubular structure of the body, such as gastrointestinal tract, colon, etc.) For example, the insertion device/apparatus 110/110*a*, e.g., via coating 120*a* (e.g., core) and/or the base structure (e.g., the cladding) can be connected to a computer, which can use such optical return signals to determine information and/or visual data regarding the tissue surrounding the insertion device/apparatus. For example, the computer can be used to receive data from a spectrometer which collects the return optical radiation, and then can decipher the information based on the properties of the optical return radiation, and determine the location of the tissue in question, its characteristics, the effect of the radiation impacting the tissue forwarded to the tissue, the effect of other materials or agents supplied to the tissue and effected by the radiation, etc.

Thus, for example, according to an exemplary embodiment of the present disclosure, the exemplary computer can generate and/or obtain images of and/or regarding the tissue provided at or near the tip of the exemplary insertion device/apparatus 110/110*a* using various imaging procedures, including but not limited to, e.g., magnetic resonance imaging (MRI), CT, OCT, OFDI, etc. In addition, these exemplary procedures can be used to provide detailed spatial information regarding the anatomical structures which are provided at or near the tip, as well as imaging one or more portions of the anatomical structure using the three-dimensional special information obtained using the above-described device.

It is also possible to utilize the insertion device/apparatus 110/110*a* to provide optical radiation to the tissue of interest an effective amount of optical radiation to effect, disrupt, damage and/or treat the tissue. Such procedure can be useful as a photodynamic therapy for treating, e.g., cancer and other deceases. For example, in one exemplary embodiment of the present disclosure, upon providing the inserting device/apparatus 110/110*a* into the body and reaching a particular location therein, a photosensitizing agent can be provided through center lumen 130/130*a* of the insertion device/apparatus 110 to a desired portion of the tissue. The coating 120*a* (e.g., the core) to provide can be used as a waveguide to deliver optical radiation directly to the area of the tissue where the photosensitizing agent was delivered with appropriate wavelength, power, etc. so as to effect, disrupt, damage and/or treat the tissue.

For example, the zone of influence from the coating 120*a* (e.g., the core) can be limited to the local area around the tip of the insertion device/apparatus. Such exemplary configuration can provide a high degree of precision with limited localized damage. An exemplary application can include an application of the optical radiation of or to small, early-stage breast tumors, e.g., sized T1 or smaller. Other soft tissue tumors can be treated as well, including regions in which RF ablation has been previously performed including, e.g., the adrenal gland, bone, kidney, liver, lung, pancreas, thyroid, or prostate. The exemplary insertion device/apparatus can provide significant advantages in ablating various tissues, including tumors and/or other lesions in highly sensitive areas where damage should be limited, including but not limited to the brain. In another example, arrays of exemplary assertion devices/apparatus which the exemplary components and/or configurations described herein can be used to treat (e.g., ablate) larger areas, for example for skin tightening. The exemplary configuration of exemplary insertion device/apparatus can be provided such that the exemplary area of thermal damage around each exemplary insertion device/apparatus can be limited thereby possibly reducing pain to the patient and/or decreasing recovery time.

In addition, it is possible to utilize the information previously obtained regarding the determination of tissue type described herein above using the coating 120*a* (e.g., core, waveguide, etc.) can be based on the tissue determination via prior determination described herein. For example, when the determination that the exemplary insertion device/apparatus has reached a particular tissue type provided via the information provided via the return optical radiation returning from the tissue via the coating 120*a* (e.g., core, waveguide, etc.), the operator and/or the computer can cause an optical source to transmit further optical therapy radiation to be transmitted to the coating 120*a* (e.g., core, waveguide, etc.), and effect, disrupt, damage and/or treat the tissue at the tip of the insertion device/apparatus 110/110*a*. The coating 120*a* (e.g., core, waveguide, etc.) may also be used to further detect changes in the tissue due to treatment, e.g., whether sufficient energy has been applied to effect, etc. the tissue.

For example, using the exemplary embodiments shown in FIGS. 1D and 1E which utilize the coating 120*a* as a single waveguide, can utilize a multiplexer to send and receive optical radiation. In this exemplary manner, it is possible to decipher the information provided via the optical radiation provided from or reflected from the tissue from the optical radiation being forwarded to the tissue.

Figure 2A:
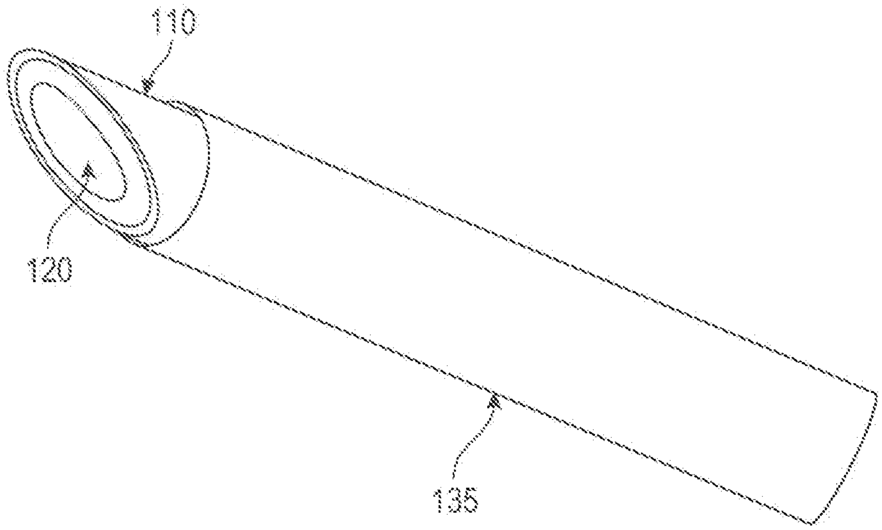
FIG. 2A is a further exemplary diagram of an elevation view of the distal end of the exemplary insertion device/apparatus according to an exemplary embodiment of the present disclosure.

FIG. 2A shows a further perspective view of an exemplary diagram of a distal end of the exemplary insertion device/apparatus according to an exemplary embodiment of the present disclosure. As shown in FIG. 2, the insertion device/apparatus can include a needle of FIGS. 1A-1C that can act as one of the electrodes 120, while multiple internal (to needle) coatings are used to produce a second electrode using sequential spray processes (e.g., as described below) to provide—internally to needle—an insulating layer, a second conductive layer, and a selective insulating layer 135 which exposes a discrete part of the outer conductive layer. The electrical current can follow the shortest possible path from one electrode to the other, (e.g., at the very tip). There can also be some contribution from the capacitive coupling through the insulating coating.

For the function of detecting/determining tissue or fluid types, based on the frequencies of interest (e.g., the frequency used to detect the tissue or fluid type), the outer insulating coating can be optional, although it can be used to provide protection for the outer conductive coating and/or lubrication to ease the insertion of needle (e.g., electrode 120).

Figure 2B:
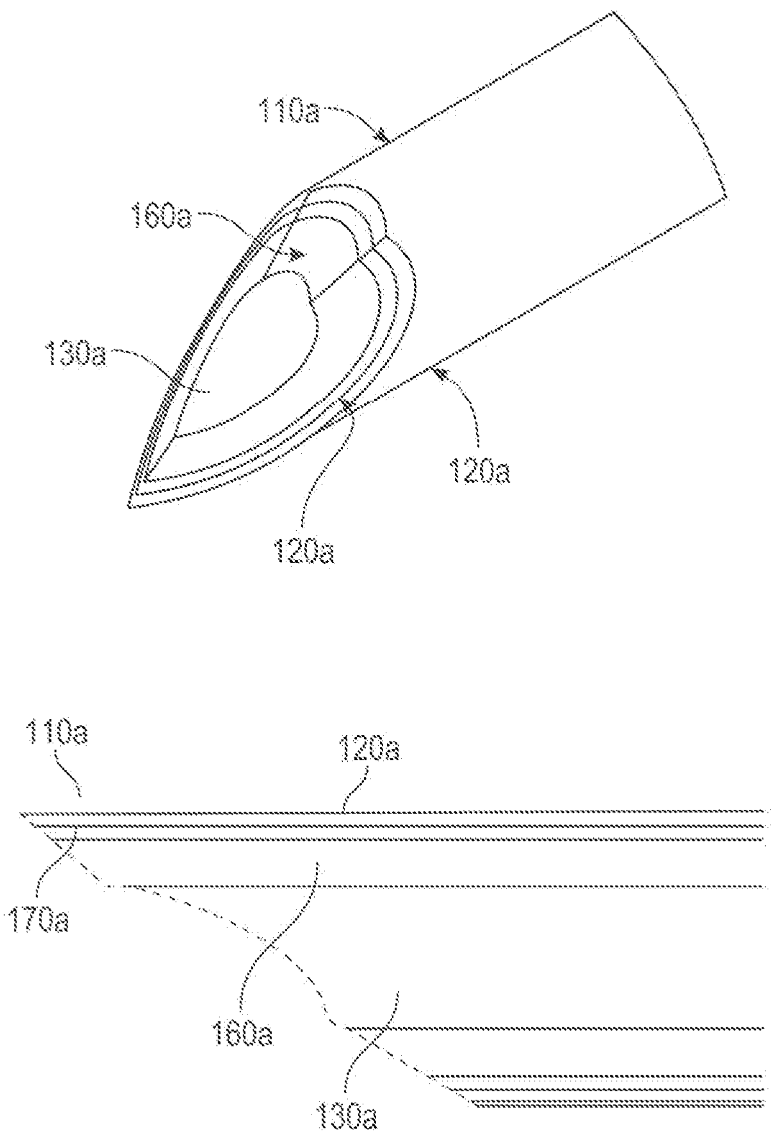
FIG. 2B is a set of exemplary diagrams of a close-up perspective view and a cross-sectional view, of an exemplary insertion device/apparatus that includes a configuration that includes a cladding layer therein, according to another exemplary embodiment of the present disclosure.

FIG. 2B shows another exemplary embodiment of the present disclosure for an exemplary insertion device/apparatus 110', and shall be described herein with reference to the components shared with the exemplary embodiments illustrated in FIGS. 1D and 1E and described herein includes all of similar components as referenced herein therefor. For example, as shown in FIG. 2B, the insertion device/apparatus 110*a* includes the coating 120*a* (e.g., the core, waveguide, etc.), which is applied or provided over a cladding 170*a*, which itself is applied or provided over the base structure 160*a*. For example, optical radiation can be provided over the coating 120*a* (e.g., the core), and directed to the tissue. Due to the cladding 170*a* having a different optical characteristics, the coating 120*a* acts more effectively as a waveguide for the optical radiation, as the cladding 170*a* prevents scattering of the optical radiation provided via the coating 120*a*, thereby directing the optical radiation as would a waveguide. Further, due to the possibility of the cladding 170*a* being also optically-transmissive, although with different characteristics from those of the coating 120*a*, it is possible to utilize the coating 120*a* (e.g., core, waveguide) to transmit the optical radiation in one direction, while transmitting separate optical radiation in another direction. In this exemplary manner, it is possible to transmit the optical radiation to the tissue via the coating 120*a*, and then provide the optical radiation from the tissue via the cladding 170*a* (or the reverse).

Figure 2C:
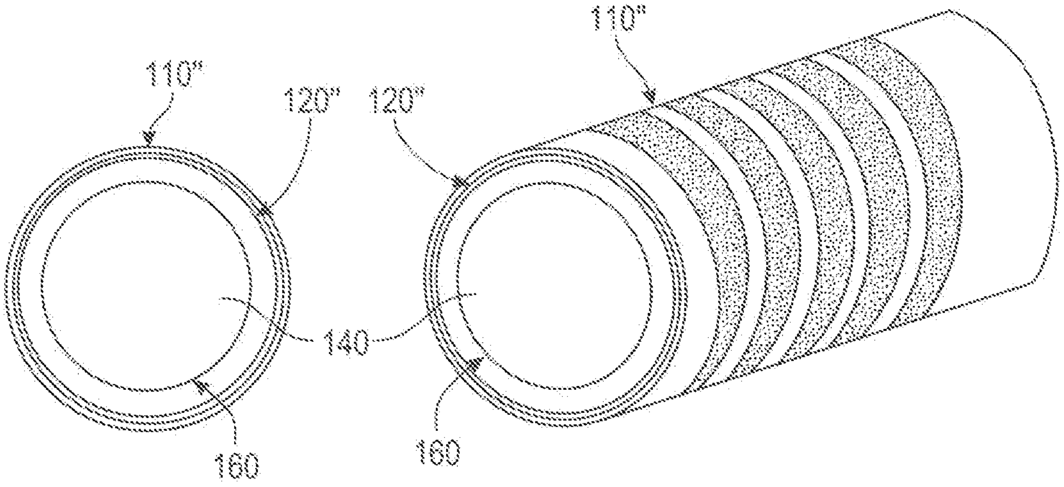
FIG. 2C is another exemplary diagram of front and perspective views of an exemplary insertion device/apparatus according to still another exemplary embodiment of the present disclosure in which the optically-transmissive coating is provided as multiple section separated from one another.

According to further exemplary embodiments of the present disclosure, an exemplary insertion device/apparatus 110' of FIG. 2C can be provided which can include more than two layers (e.g., more than one combination of the outer optically-transmissive coating (e.g., core) 120*a* and the cladding 170*a*. For example, in the same manner as described herein above for the exemplary embodiments of FIGS. 1D, 1E and 2B, additional layers can be applied to produce the above-described core/cladding combination. In such exemplary embodiment, the cores (e.g., coatings, waveguides) 120*a* can be used to transmit optical radiation to the tissue, and the claddings 170*a* can be used to receive the optical radiation from the tissue. Further, it is possible to use one or more of the core/cladding combinations for transmitting the optical radiation to the tissue, while another one or more of the core/cladding combinations for receiving the optical radiation from the tissue. Thus, the transmission of the radiation using multiple cores and claddings (e.g., performed in parallel or in series) and the deciphering thereof by the computer can expedite the transmission of the optical radiation and the processing/deciphering of the received optical radiation.

According to another exemplary embodiment of the present disclosure, another exemplary insertion device/apparatus 110" can be provided, as shown in FIG. 2C. Indeed, the same exemplary portions/components of the exemplary insertion device/apparatus illustrated in FIGS. 1D and 1E are labeled with the same numerals in FIG. 2C. Nonetheless, instead of providing a single coating which is applied on and circumferentially surrounds the base structure 160, masking can be used to produce and/or provide helical-patterned and/or other exemplary patterned structures of a coating which define outer waveguides 120". Such exemplary use of the helical-patterned outer waveguides 120" (e.g., coatings) can improve the transmission of the optical radiation to facilitate an expedited transmission of the radiation, e.g., which can be performed in parallel. For example, referring again to FIG. 2C, optical radiation can be transmitted along the waveguides 120" of the device (e.g., —provided on the surface of the base structure 160, which can be separated by a splitter into individual ones of the waveguides 120". The separated optical radiation portions emitted from such individual waveguides 120" are forwarded to the tissue structure at different locations thereof which correspond to the locations of the individual waveguides 120" situated on the base structure 160. The return optical radiation can be simultaneously or serially received by the same individual waveguides 120" which emitted the radiation being forwarded to the tissue, or by other adjacent or non-adjacent waveguides 120".

Figure 2D:
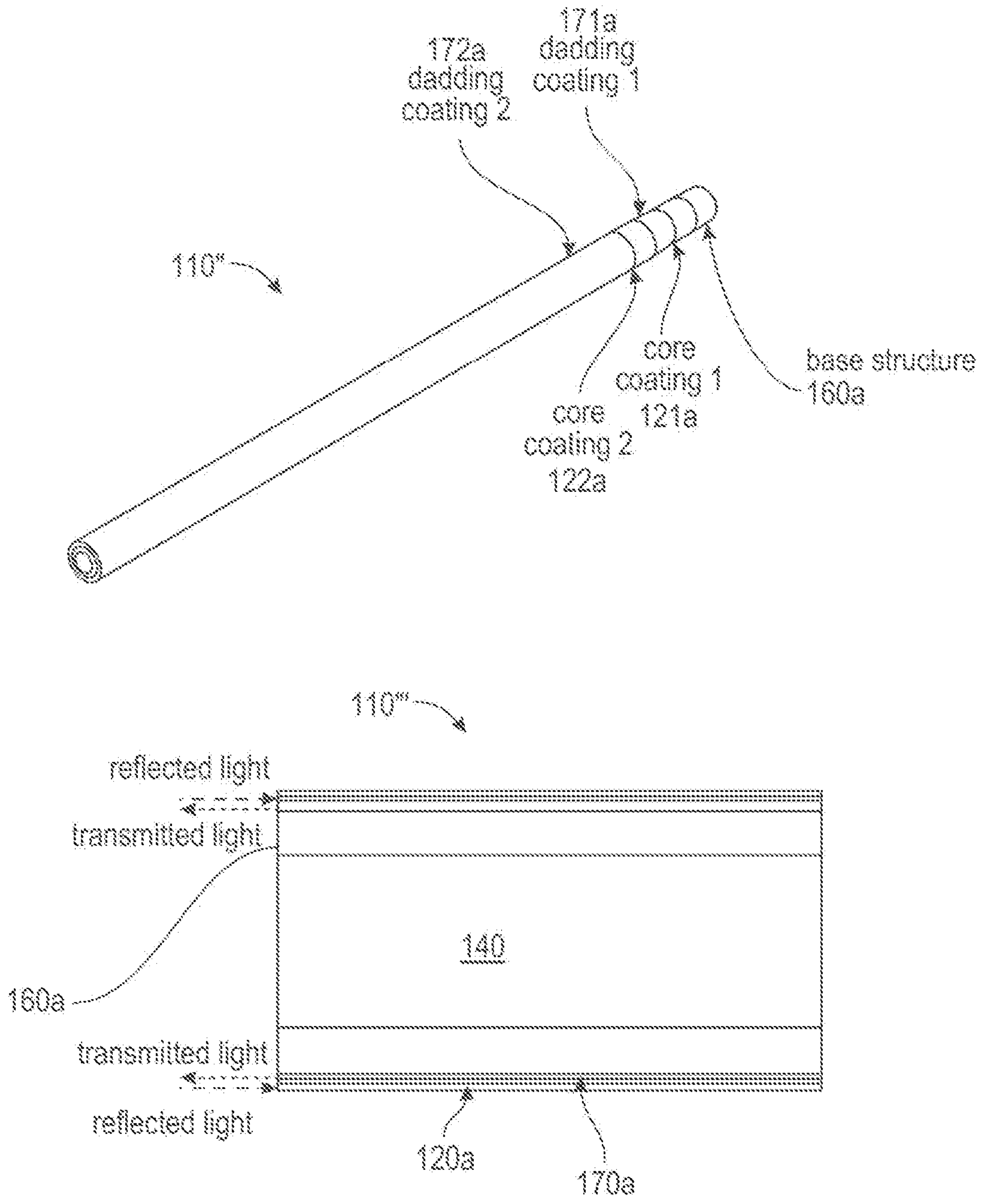
FIG. 2D is an exemplary diagram of front and perspective views of an exemplary insertion device/apparatus according to still another exemplary embodiment of the present disclosure in which multiple section of the optically-transmissive layer are provided on the cladding layer, and are separated from one another via sections of the cladding later.

FIG. 2D illustrates perspective views of the exemplary embodiment of the present disclosure which is very similar to the exemplary embodiment show in FIG. 2C. As described herein, the same components illustrated in FIG. 2C shall be numbered in the same manner in FIG. 2C, except that the cladding 170*a* of FIG. 2D is provided between the base structure 160*a* and the coating/core 120", with reference made to FIG. 2C. In particular, as provided in FIG. 2C, the waveguides 120" are shown, in FIG. 2D, as core coating sections 121*a*, 122*a*, which are separate from one another by a cladding coating section (of the cladding 160*a*), which is the followed (following the coating section 121*a*) by a cladding coating section. In this exemplary configuration shown in FIG. 2D, similar operation can be performed as described herein above, and the insertion device 110'" can be used in the same manner as described herein with respect to the insertion devices according to other exemplary embodiments, e.g., with reference to FIGS. 2B and 2C. For example, as provided in FIG. 2D, cladding coating sections (and thus the cladding 170*a*), and the core coating sections 121*a*, 122*a* (and thus the coating/core 120") can be provided over the cladding 170*a*. The core coating sections 121*a*, 122*a* can be separated from one another by the cladding section 171*a*, and another cladding section can 172*a* follow the core coating section 122*a*. In this exemplary manner, it is possible to provide an emission of the optical radiation via different sections of the core 120" and/or the cladding 170*a* to and from the tissue, e.g., in a similar manner as described herein above with respect to the exemplary embodiment shown in FIG. 2C. For example, according one exemplary embodiment, the optical radiation forwarded to the tissue can be provided via the cladding coating sections 171*a*, 172*a* (and thus via the cladding 170*a*), and the optical radiation returning from the tissue can be provided via the core coating sections 121*a*, 122*a* (and thus via the core 120"). Of course, the reverse optical radiation transmission can be effectuated as well, e.g., the optical radiation forwarded to the tissue can be provided via the core coating sections 121*a*, 122*a* (and thus via the core 120"), and the optical radiation returning from the tissue can be provided via the cladding sections 161*a*, 162*a* (and thus via the cladding 170*a*).

The exemplary insertion device/apparatus can include more than two layers (e.g., more than two insulating and conducting layers). For example, additional layers can be applied to produce additional electrodes. In certain exemplary applications, it can be beneficial to utilize more than two electrodes to sense, detect and/or identify fluids or tissues, for example, when the impedance of the fluid/tissue can be lower than the impedance of the sensing electrodes themselves. (See e.g., Reference 5).

Figure 3:
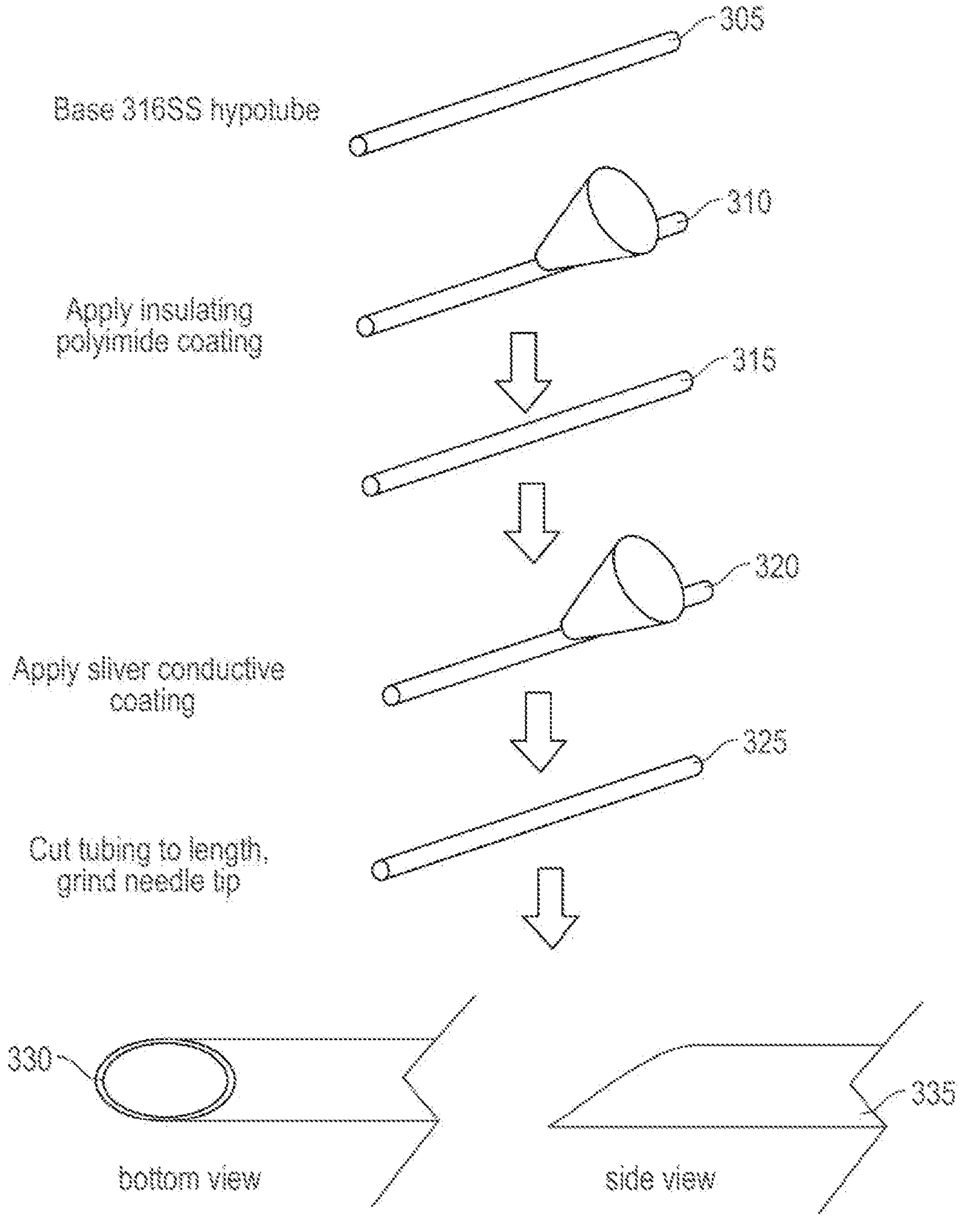
FIG. 3 is an exemplary diagram of various exemplary steps/procedures of a method for applying layers to the exemplary insertion device/apparatus according to an exemplary embodiment of the present disclosure.

FIG. 3 shows an exemplary diagram of a method 300 for applying layers to the exemplary insertion device/apparatus according to an exemplary embodiment of the present disclosure. As shown in FIG. 3, the multi-layer structure of the insertion device/apparatus can be produced by applying the layers with a spray process using, for example, an insulating and a conductive and/or optically transmissive ink. For example, at procedure 305, a base hypotube can have an insulating polyimide coating applied thereto at procedures 310 and 315. At procedure 320, a silver conductive coating can be applied to the tube, and at procedure 325, the tube can be cut to length, and the tip of the insertion device/apparatus can be created by, e.g., grinding or laser cutting. Element 330 illustrates a bottom view of the finished insertion device/apparatus (e.g., needle, cannula, endoscope, laparoscope, etc.), and element 335 shows a side view of the finished insertion device/apparatus.

The exemplary procedure shown in FIG. 3 can limit the coatings to the outside of the tubing/needle leaving the center open. For example, eliminating masking and etching can keep the process for applying the layers relatively simple. After each procedure, the structure can be heated to remove any solvent, and to polymerize the coating.

Figure 4A:
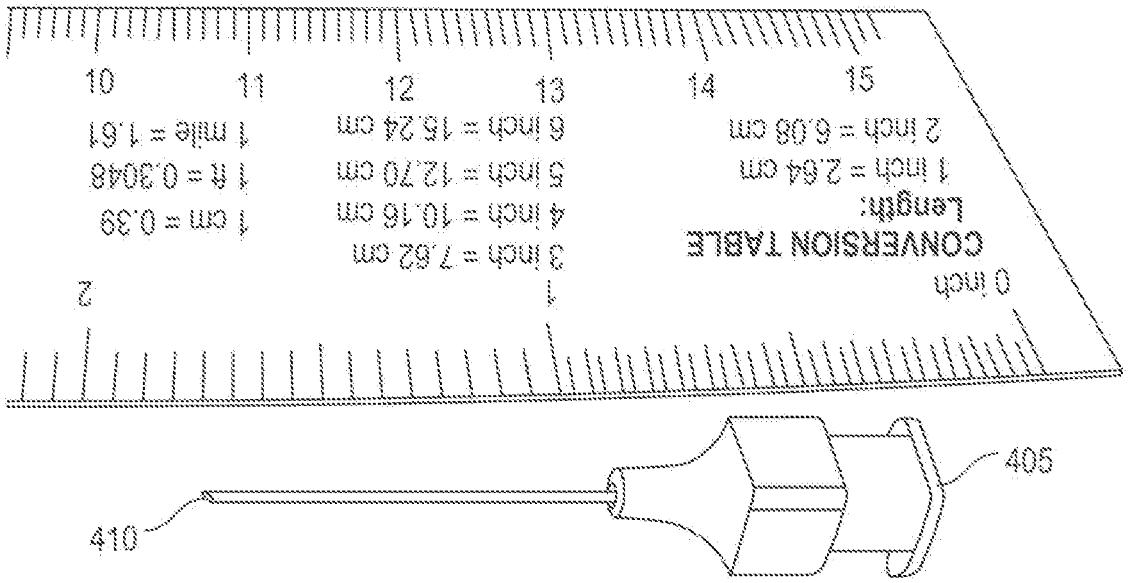
FIG. 4A is an exemplary image of the exemplary insertion device/apparatus according to an exemplary embodiment of the present disclosure.
Figure 4B:
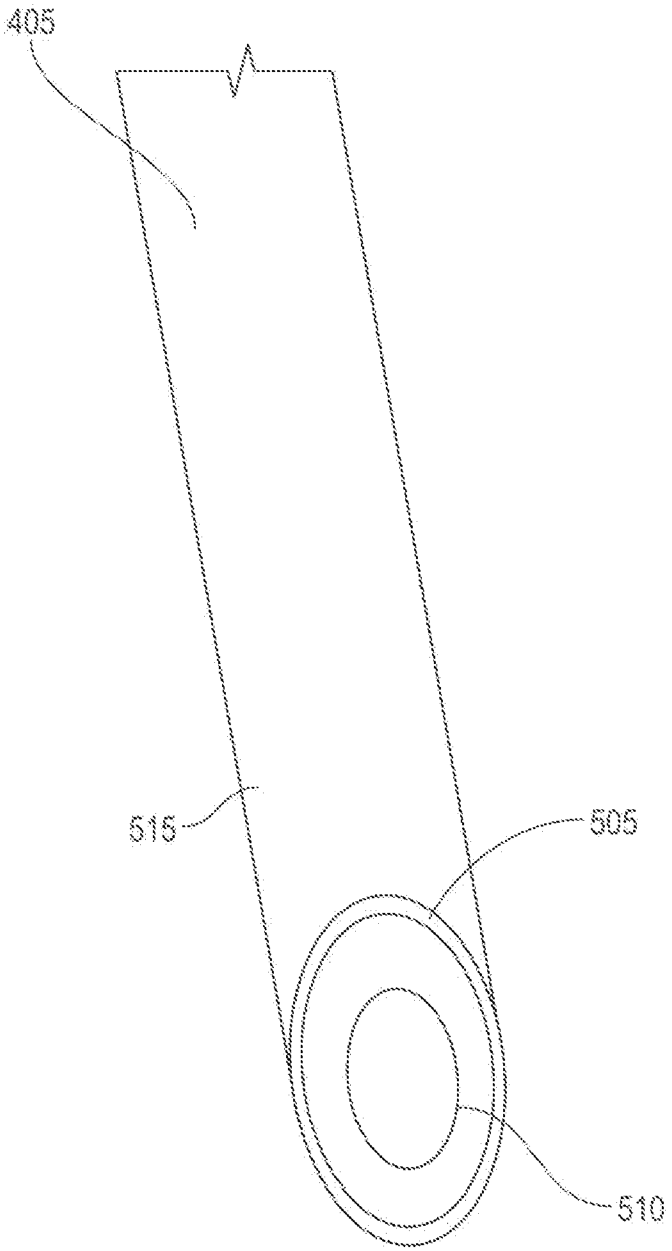
FIG. 4B is an exemplary close-up image illustrating the structure of the exemplary insertion device/apparatus fabricated with a layer of polyimide and an outer layer of silver conductive ink applied using a spray process according to an exemplary embodiment of the present disclosure.

FIG. 4A shows an exemplary image of exemplary needle 405 according to an exemplary embodiment of the present disclosure. For example, exemplary needle 405 was produced from 26 Ga 316SS tubing using the exemplary method shown in FIG. 3. The conductive coating on needle 405 was produced using a conductive silver ink (e.g., Creative Materials 118-43T). The base insulating coating is a polyimide (e.g., Jaro 650). As shown in FIG. 4A, needle tip 410 was laser cut. It should be understood that the tip of needle 450 can also be fabricated using other suitable techniques used to produce exemplary needles according to the exemplary embodiment of the present disclosure, such as, for example, grinding. FIG. 4B shows an exemplary close-up image illustrating the structure of the exemplary needle fabricated with a layer of polyimide (e.g., insulating layer 505 surrounding a stainless steel body 510) and an outer layer 515 composed of a silver conductive ink. Both insulating layer 505 and outer layer 515 were applied using an exemplary spray process (e.g., as described above in FIG. 3).

Figure 5:
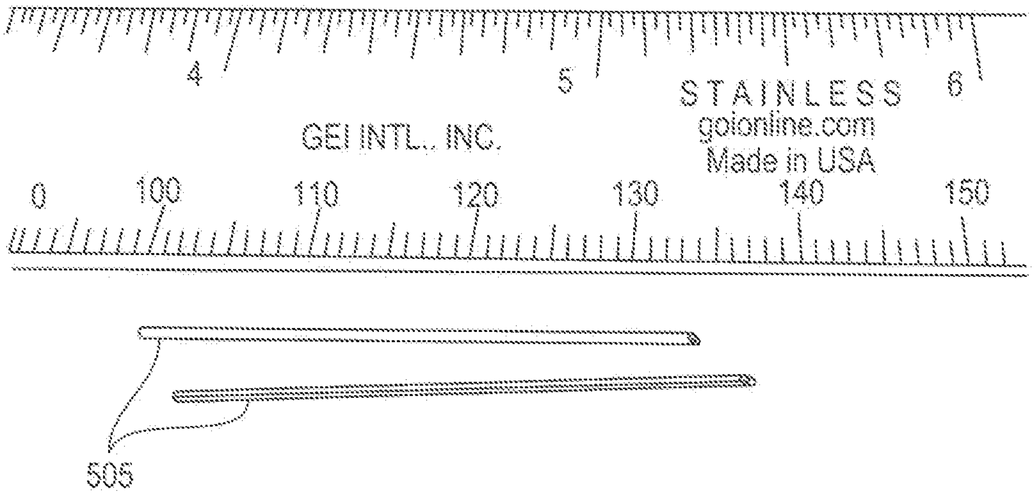
FIG. 5 is an exemplary image of exemplary insertion devices/apparatuses produced using a grinding process according to an exemplary embodiment of the present disclosure.

FIG. 5 shows an exemplary image of exemplary needles 505 produced using a grinding process according to an exemplary embodiment of the present disclosure. The layers of exemplary needles 505 can be produced through procedures other than spray coating such as electrochemical deposition, vapor deposition or sputtering, although not limited thereto. Masking can also be used to produce geometric patterns during the coating process. Alternatively or in addition, a mask can be applied after the coating, similar to the exemplary process used to produce printed circuit boards. In such an example, the mask can be spared during chemical etching.

Figure 6:
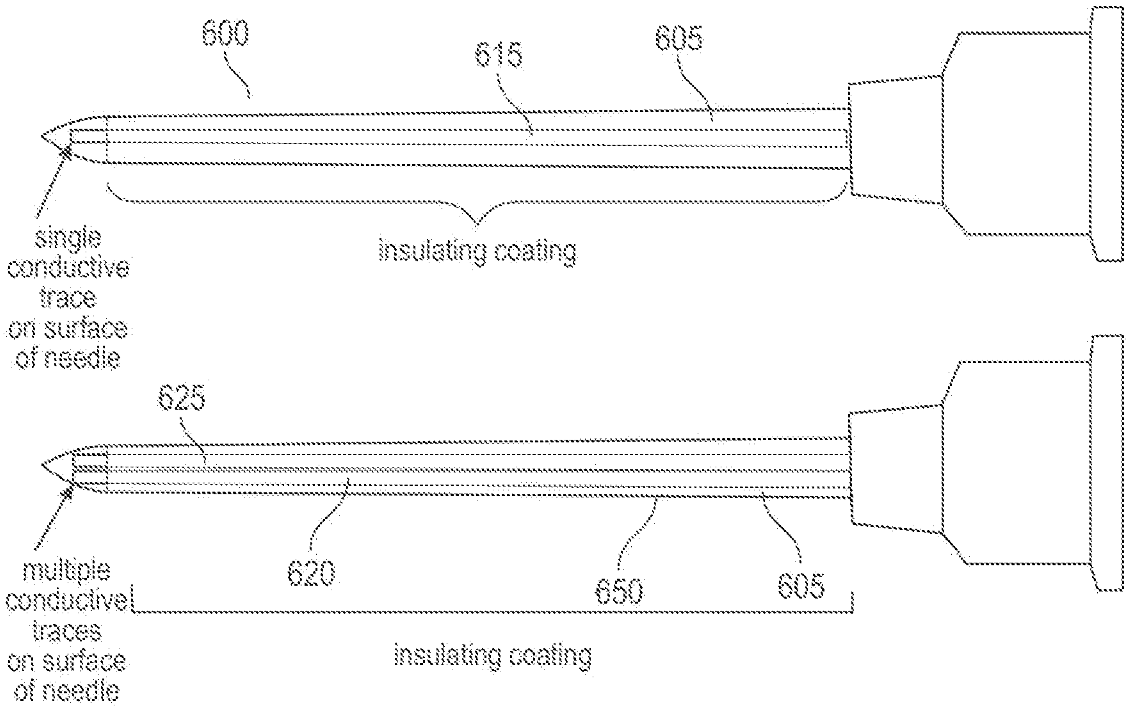
FIG. 6 is a set of side views of exemplary diagrams of different conductive traces used for the exemplary insertion device/apparatus according to an exemplary embodiment of the present disclosure.

FIG. 6 shows a set of side cross-sectional view and exemplary diagrams of needles 600 having different conductive traces according to an exemplary embodiment of the present disclosure. For example, as illustrated in FIG. 6, needle 600 can include an insulating coating 605, which can be used to insulate a single conductive trace 615 located on the surface of needle 600. Another needle 650 can also include an insulating coating 605. Further, needle 650 can include multiple conductive traces (e.g., traces 620, 625) on the surface of needle 650.

In conjunction with the exemplary embodiment shown in FIG. 6, the electrodes can be fabricated on the surface of a needle using procedures such as pad printing or screen printing with an outer insulating layer applied after. The insulating coating can be printed, deposited, or applied in the form of shrink tubing.

Figure 7:
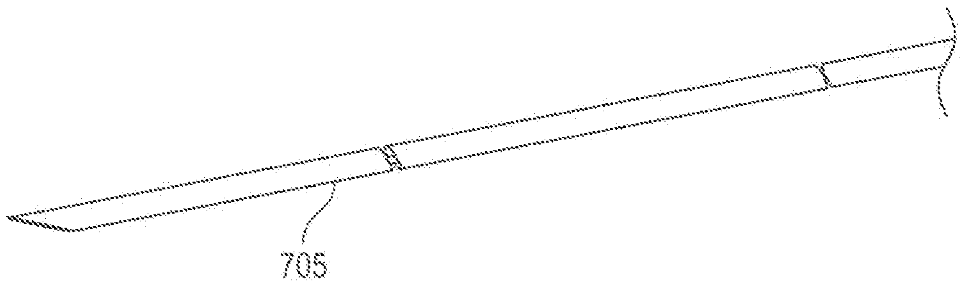
FIG. 7 is an exemplary image of an exemplary insertion device/apparatus having a surface electrode that was pad printed using ink according to an exemplary embodiment of the present disclosure.

FIG. 7 shows an exemplary image of an exemplary needle 705 having a surface electrode that was pad printed using ink according to an exemplary embodiment of the present disclosure. Exemplary needle 705 is a conventional 26 Ga hypodermic needle. The conductive surface electrode was pad printed using an ink specifically formulated for pad printing (e.g., Creative Materials 118-43T).

Figure 8:
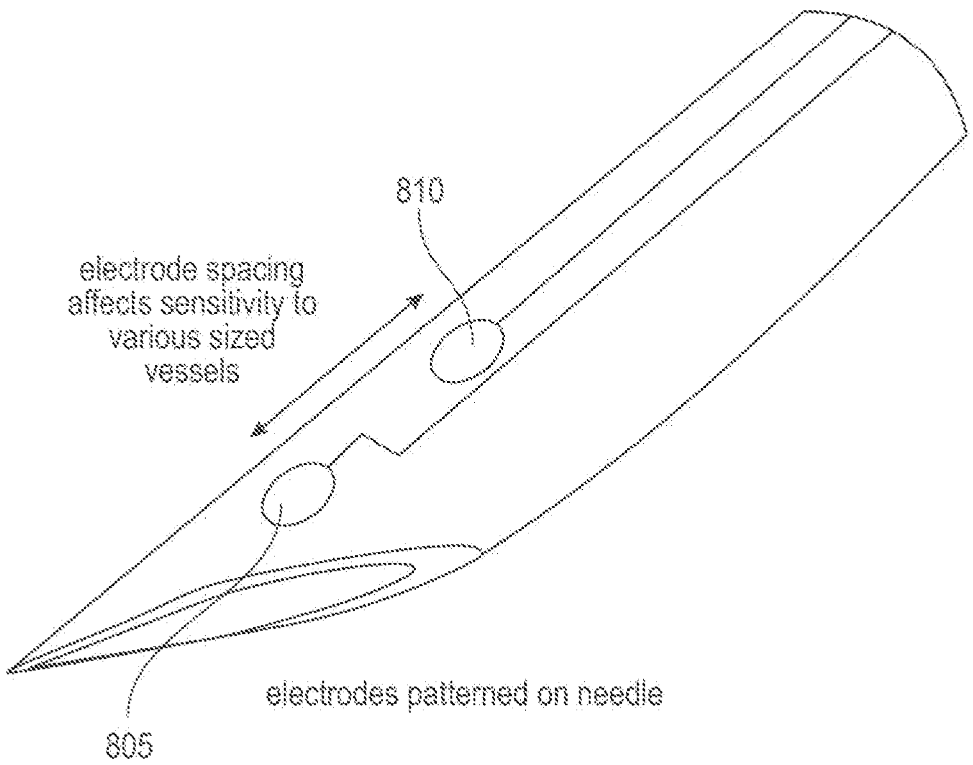
FIG. 8 is an exemplary expanded diagram of the distal end of the exemplary insertion device/apparatus having electrodes patterned on the exemplary insertion device/apparatus according to an exemplary embodiment of the present disclosure.

FIG. 8 shows an exemplary close-up diagram of the distal end of the exemplary insertion device/apparatus (e.g., needle) having electrodes 805, 810 patterned on the insertion device/apparatus according to an exemplary embodiment of the present disclosure. The spacing between electrodes 805, 810 can be varied to produce a physical filter to tailor sensitivity to different size structures. For example, the electrodes can be separated such that the spacing can be greater than the size of a specific artery. In such exemplary case, the electrodes should not be both be inside a blood vessel (e.g., an artery, a vein, etc.) at the same time which can affect electrical impedance.

Figure 9:
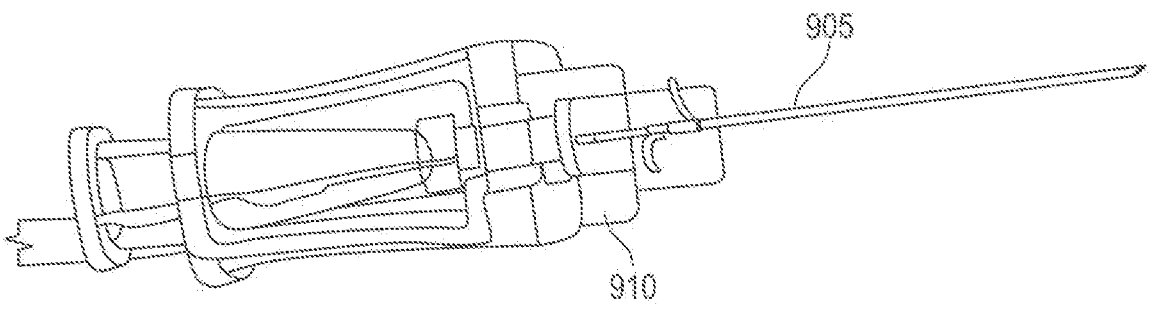
FIG. 9 is an exemplary illustration of the exemplary insertion device/apparatus according to an exemplary embodiment of the present disclosure.
Figure 10A:
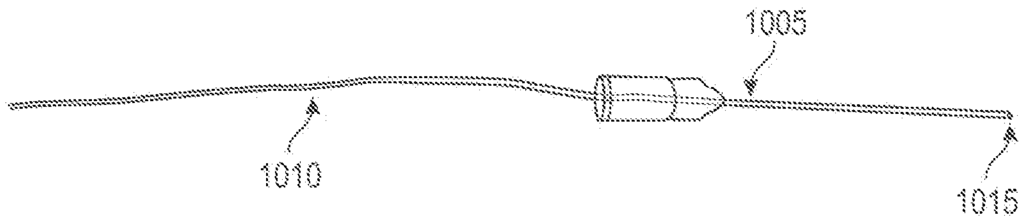
FIG. 10A is an exemplary image of the exemplary insertion device/apparatus having magnetic wires attached thereto according to an exemplary embodiment of the present disclosure.
Figure 10B:
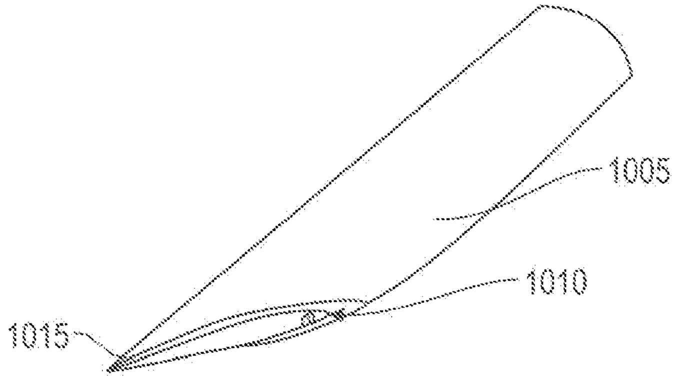
FIG. 10B is an exemplary diagram of the exemplary insertion device/apparatus shown in FIG. 10A illustrating the attachment of the magnetic wire according to an exemplary embodiment of the present disclosure.

FIG. 9 shows an exemplary image of the exemplary needle 905 according to another exemplary embodiment of the present disclosure. Electrodes connected to needle 905 can also be electrically connected to an external instrument using wires or a flex circuit. The flex circuit can form a flex cable for connection to the instrument. A clip (e.g., clip 910) can be used to provide an electrical connection to the needle 905, as well as contacting the needle body as well as the outer conductive coating.

Figure 11:
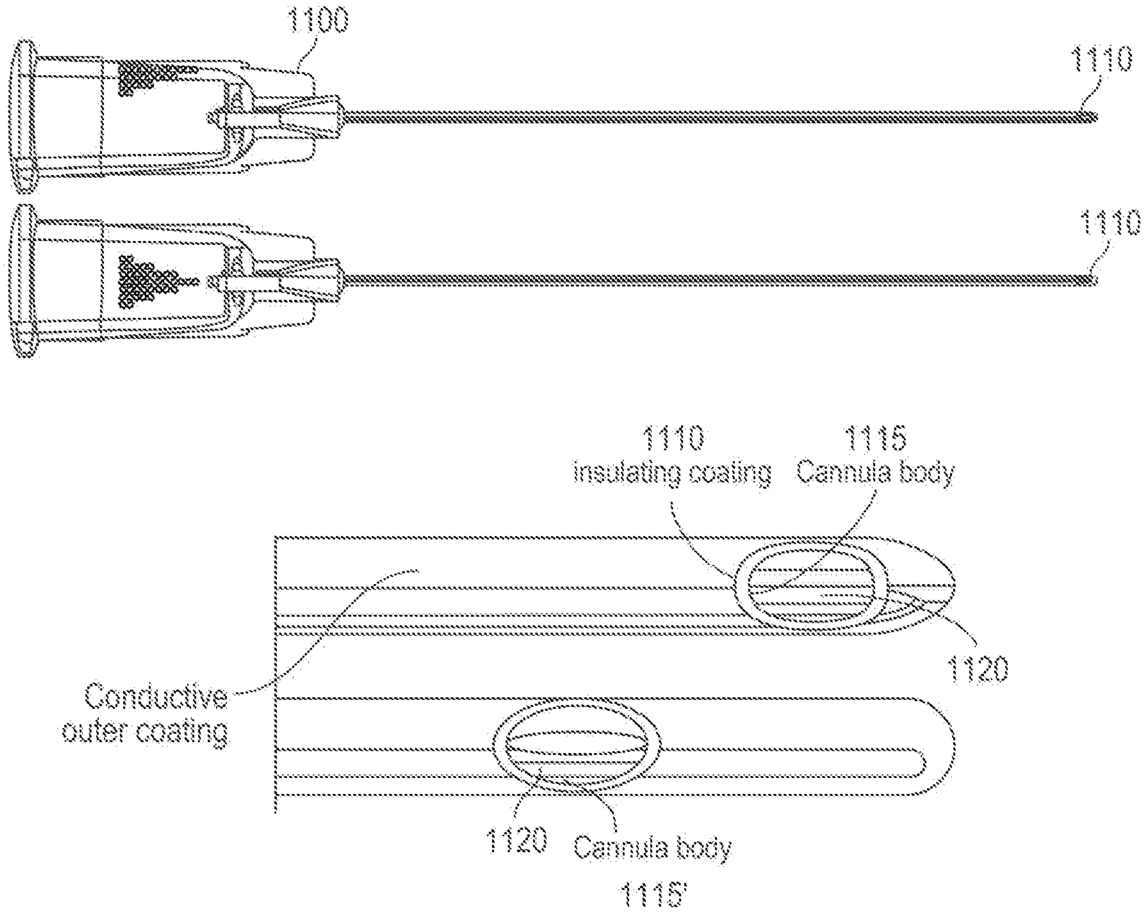
FIG. 11 is a set of side cross-sectional views of another exemplary embodiment of the exemplary insertion apparatus which provides an exemplary sensing technology implemented in the form of a cannula, according to yet another exemplary embodiment of the present disclosure.

FIG. 11 shows a set of side views of another exemplary embodiment of the exemplary insertion apparatus 1100 which provides an exemplary sensing technology implemented in the form of a cannula, according to yet another exemplary embodiment of the present disclosure. As illustrated in FIG. 11, at or near a tip 1105 of the exemplary insertion apparatus, a cannula body 1115, 1115' can be coated (e.g., with an insulating coating 1110) to produce a sensing structure around the cannula openings 1120.

Figure 13:
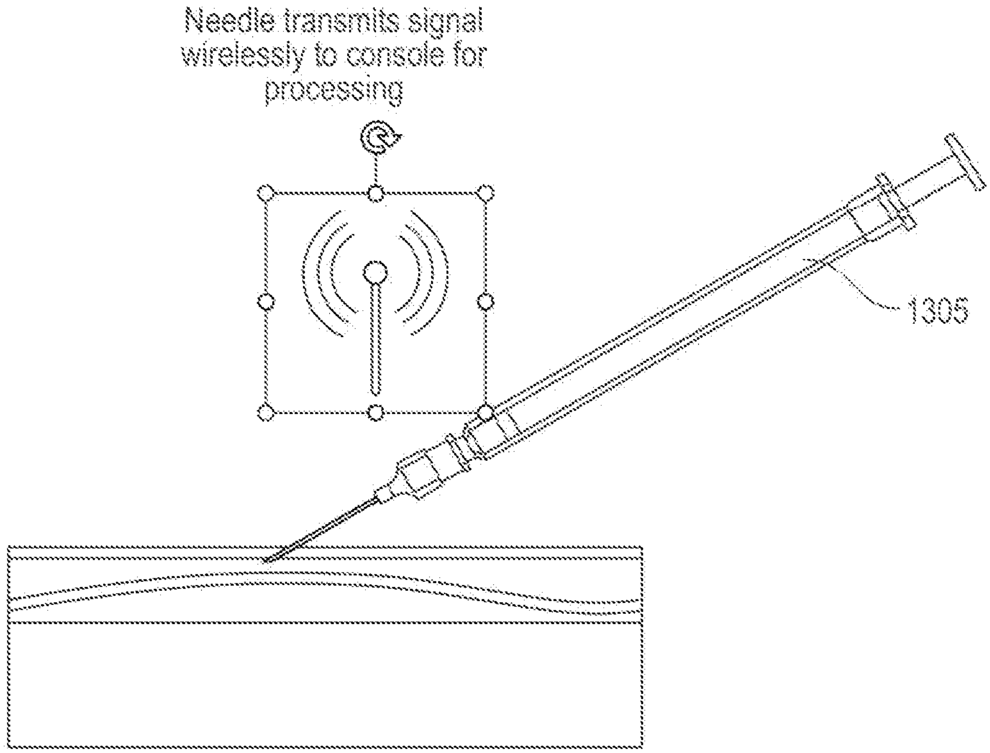
FIG. 13 is an exemplary diagram illustrating wireless transmission of information from the exemplary insertion device/apparatus for use in determining the tissue type according to an exemplary embodiment of the present disclosure.

FIG. 13 shows an exemplary diagram illustrating that information can be wirelessly transmitted from a transmitted of the exemplary insertion (e.g., needle) apparatus 1305 for use in determining the tissue type according to an exemplary embodiment of the present disclosure. For example, an exemplary processor, microprocessor, etc. can be embedded in either at any portion of the needle apparatus 1305, including but not limited in the needle itself, which can be used to collect the electrical information obtained using the electrodes. This information can be sent to another device (e.g., using a wired or wireless transmission medium, as discussed below), which can be used to analyze the information, determine the impedance, and ascertain the tissue type.

Figure 14:
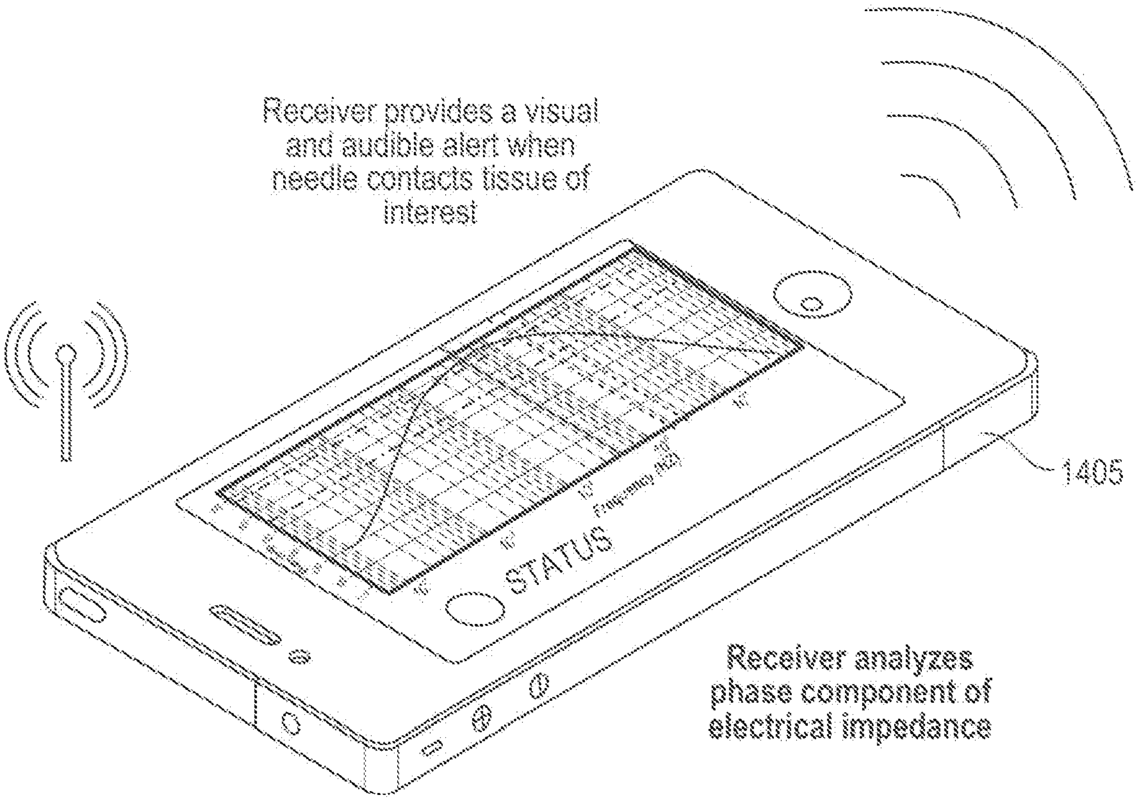
FIG. 14 is an exemplary diagram of an exemplary mobile device used to receive the wireless transmission of information from the exemplary insertion device/apparatus shown in FIG. 13, which can be used to determine the tissue type according to an exemplary embodiment of the present disclosure.

FIG. 14 shows an exemplary diagram of an exemplary mobile device 1405 used to receive the wireless transmission of information from the exemplary insertion (e.g., needle) apparatus illustrated in FIG. 13 to determine the tissue type according to an exemplary embodiment of the present disclosure. For example, exemplary needle apparatus 1305 can have a wireless communication chip embedded therein (including in any part thereof, such as the needle, etc.), which can be powered using an internal battery, through an external electrical connection, or through any suitable wireless power medium. The power supplied to needle apparatus 1305 can be used to power the wireless communication chip, as well as any microprocessor embedded in needle apparatus 1305. Alternatively, power can be obtained from electrical signals present in the body of the subject, which can provide sufficient power to send a burst signal of information from needle apparatus 1305 to device 1405.

The exemplary tissue detection system/apparatus can include a single insertion device/apparatus (e.g., a needle, a cannula, etc.). However, the exemplary tissue detection system/apparatus can include a plurality of insertion devices (e.g., an array of needles, an array of cannulas, an array of mixture of needle(s)/cannula(s), etc.). Each insertion device in the array thereof can be of the same electrode design/structure (e.g., one design of the various exemplary electrode designs/structures described above). However, each insertion device in the array can have a different design/structure, or a subset of the insertion devices can have one design/structure while another subset can have a different design/structure. Each insertion device in the exemplary array thereof can perform tissue detection as described above, and each insertion device can also perform a medical function (e.g., the administering of a material or a substance or the removal of a biopsy sample and/or other fluid, tissue, cells or material). Thus, one or more insertion devices in the exemplary array thereof can perform the tissue detection, while one or more other needles can perform the medically-related functions. The exemplary array of the insertion devices can also be used to increase the accuracy of the tissue detection by increasing the number of the electrodes that are used to determine the impedance. Additionally, a comparison of the impedance between the insertion devices in the array can also be used to determine the tissue type.

Exemplary Operation and Determination of Tissue Type

The exemplary insertion device/apparatus can be used to measure impedance around the tip of the needle. Impedance, Z can be a measure of the opposition of a medium to alternating current flow at a given frequency. Z can be defined by, for example:

$$Z=R+jXc$$

where R can be resistance and Xc can be reactance. Resistance can vary with geometry and resistivity of the medium. Reactance can vary with frequency and capacitance.

As the exemplary insertion device/apparatus passes through the different tissues, the instrument can read the impedance and phase angle at the needle tip at a fixed frequency, for example, 10,000 Hz. As the exemplary insertion device/apparatus passes through different types of tissue, the measured/inferred impedance can show a distinct change. Electronics integrated into the hub of the exemplary insertion device/apparatus can provide a measurement of the current. The exemplary apparatus can be used to provide either a warning (e.g., to avoid a procedure) or a helpful alert (e.g., to proceed with a procedure).

The exemplary insertion devices/apparatuses can be used as a replacement for current disposable hypodermic needles. Potential uses can include injection and minimally invasive instrument introduction. During an injection procedure, for example a filler injection, the clinician can insert the exemplary insertion devices and manipulate the needle as per normal operation. For example, as the exemplary insertion device/apparatus penetrates a blood vessel (e.g., an artery, a vein, etc.), the exemplary apparatus can provide an audible and/or a visual alert to warn the clinician that it may be hazardous to inject a particular material (e.g., the filler). For other types of injections, for example, an intradermal vaccine injection, a clinician can be provided with an indication that the needle is in the intradermal space in which case, the clinician can wait for an alert before injecting.

Electrical connections can be made to connect the electrodes to the electronics that can sense and interpret the electrical impedance. The electronics can be integrated into the needle, as close as possible to the electrodes. Exemplary electronics can include a source to generate an oscillating voltage and a measurement device to determine the magnitude and phase between the applied voltage and the current. The electronics can be packaged to be integrated into the hub of the exemplary insertion device/apparatus which can typically be used to connect the exemplary insertion device/apparatus to a syringe. For example, Analog Devices manufactures a single chip in an 8 mm×8 mm package, the ADuCM350, which can be used to analyze impedance over a wide range of frequencies. Such exemplary chip can easily fit within the envelope of a standard Luer hub. The connection between the electrodes and the integrated electronics can be made using traces produced at the same time as the electrodes. The ADuCM350 chip can contain an audio driver which can be used to produce an audible sound to alert a user when the exemplary insertion device/apparatus has been inserted into and/or penetrated a specific tissue structure.

The exemplary electronics can communicate wirelessly with an external receiver for further processing. Wireless communication can be performed using any low power hardware, for example Bluetooth LE, ANT, RF, or Zigbee. The exemplary apparatus can be tailored to focus on the response at a very narrow band of frequencies rather than across a broad spectrum. Therefore, custom electronics tailored for a specific tissue type can be much simpler than a general analyzer. The exemplary insertion device/apparatus can be further simplified by offloading processing to an external console. The electronics on the exemplary insertion device/apparatus can be limited to simply measuring the current in response to the input, transmitting the response to the console via a low power RF or other transmission scheme.

Exemplary Biopsy Operation

Figure 22A:
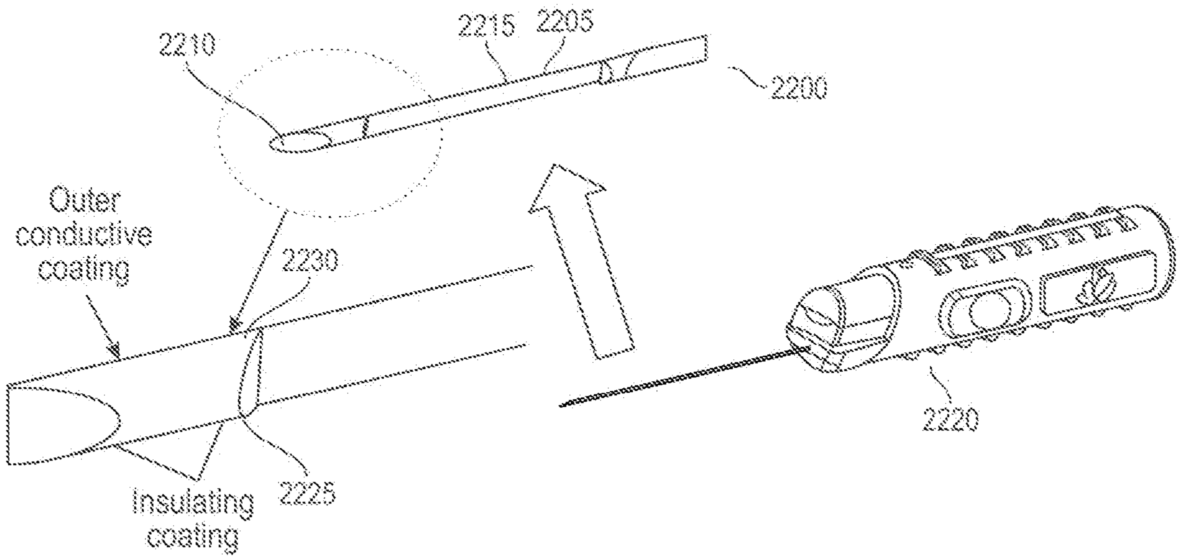
FIG. 22A is an exemplary diagram of an exemplary device for use in core biopsies, according to an exemplary embodiment of the present disclosure.
Figure 22B:
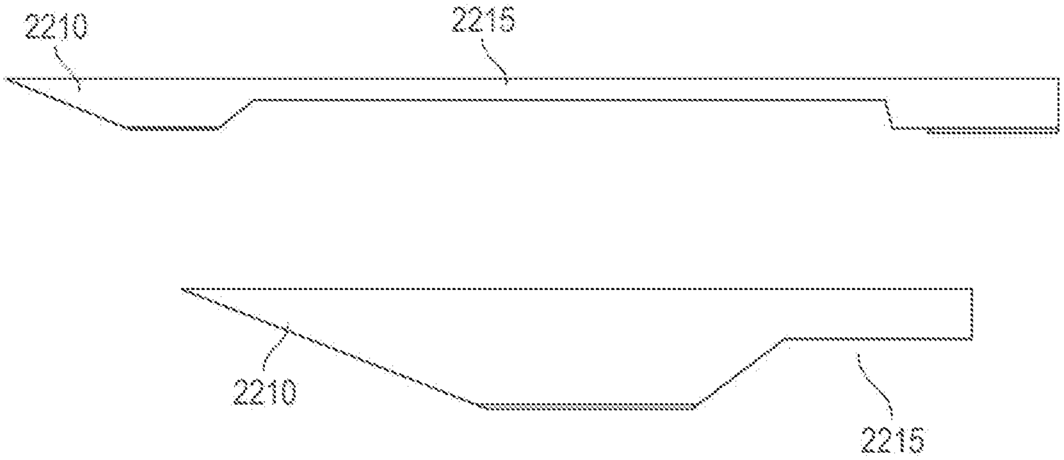
FIG. 22B is an exemplary diagram of the cross-section of the exemplary device shown in FIG. 22A, according to an exemplary embodiment of the present disclosure.

FIG. 22A shows an exemplary diagram of an exemplary device for use in core biopsies, according to an exemplary embodiment of the present disclosure. FIG. 22B shows an exemplary diagram of the cross-section of the exemplary device shown in FIG. 22A, according to an exemplary embodiment of the present disclosure. As shown in FIGS. 22A and 22B, the exemplary core biopsy needle 2200 can incorporate a central needle 2205 with a sharpened point 2210 and a concave section 2215 proximal from the point. Concave section 2215, which can be referred to as a bowl, can be the region in which a tissue sample is collected and retained. Once the needle point 2210 is positioned in the desired location in the tissue, an outer sleeve 2220 with a sharpened edge advances to cut/shear tissue, capturing the desired sample between sleeve 2220 and needle 2200. Core biopsy needles can be placed using ultrasound imaging, magnetic resonance (MR) imaging, or stereotaxis imaging. Approximately 2.8% of core biopsies result in false negative diagnoses.

Figure 22C:
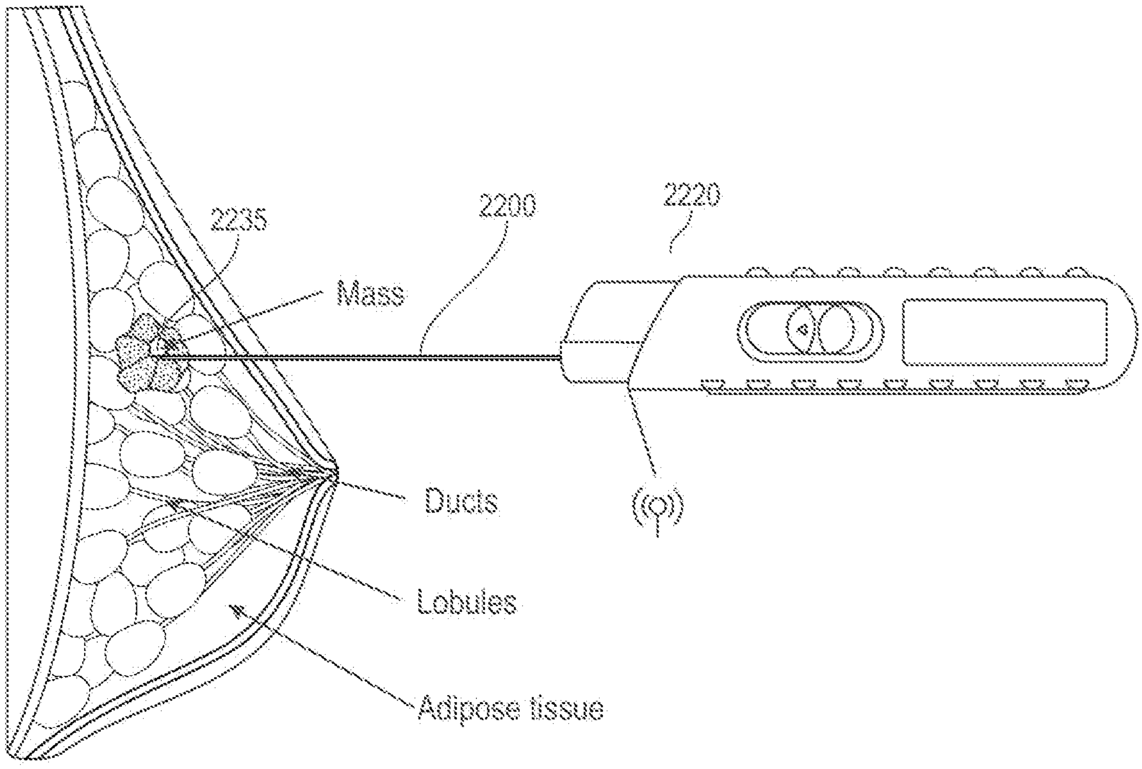
FIG. 22C is an exemplary diagram of the exemplary device shown in FIG. 22A inserted into a breast, according to an exemplary embodiment of the present disclosure.

As shown in FIG. 22A, concentric coatings 2225 and 2230 can be applied to the needle material prior to be ground and formed into the final shape. The grinding of the point and the bowl section can expose the edges of the coatings. This can produce a dual electrode structure at the point, and also in the region of the bowl as illustrated in FIGS. 22B and 22C. FIG. 22C shows an exemplary diagram of needle 2200 being inserted into a mass 2235 in a breast, according to an exemplary embodiment of the present disclosure.

This structure of the core biopsy needle can facilitate sensing during initial needle guidance and also during collection. The sensing structure of the needle point can facilitate impedance measurement as the needle is advanced through tissue to the target location, which can typically be abnormal tissue identified through imaging. The structure can also facilitate sensing of tissue impedance within the bowl. Sensing the impedance of tissue located in the region of the bowl can facilitate the confirmation that the tissue is abnormal prior to collection. A combination of sensing during advancement, and just prior to collection, can aid in the reduction of false negatives due to incorrect placement of a core biopsy needle.

Figure 22D:
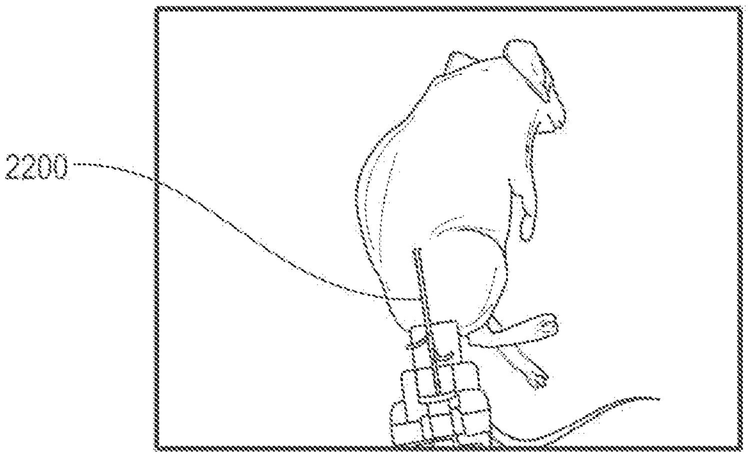
FIG. 22D is an exemplary image of the exemplary device shown in FIG. 22A inserted into a mouse and a set of exemplary graphs illustrating the resulting measurements, according to an exemplary embodiment of the present disclosure.
Figure 22D:
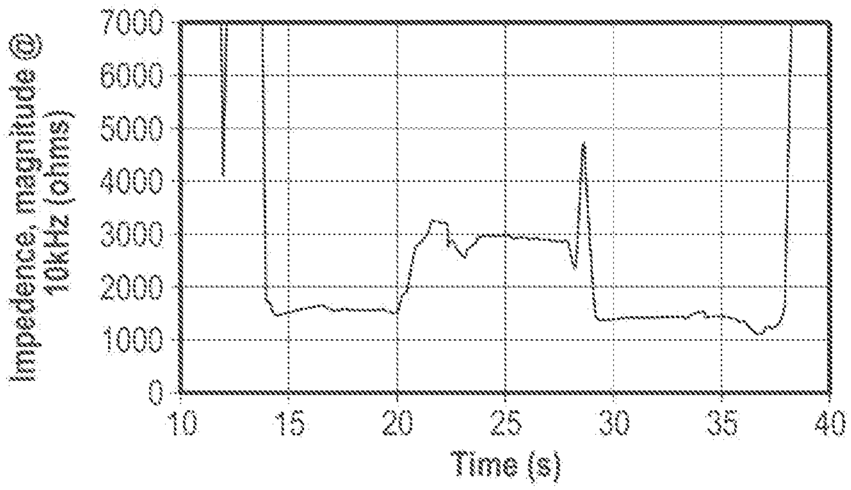
Figure 22D:
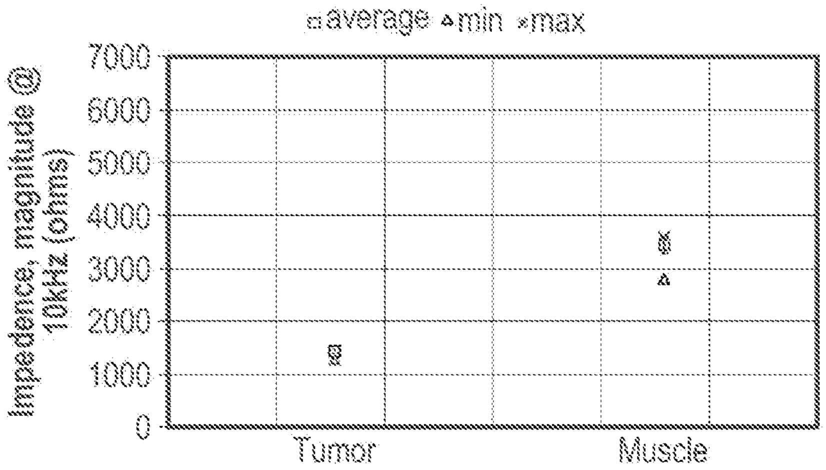

FIG. 22D shows an exemplary image of the exemplary device shown in FIG. 22A inserted into a mouse and a set of exemplary graphs illustrating the resulting measurements, according to an exemplary embodiment of the present disclosure. Some abnormal, cancerous tissue can be highly vascularized. This can produce a structure with distinct differences in electrical impedance that can be determined from surrounding, non-cancerous tissue. Vascularized tumors can occur anywhere in the body. Exemplary measured impedance data that can be representative of target abnormal tissue is shown in FIG. 22D, which illustrates data collected in mice afflicted with melanoma. The data illustrates 1) measured impedance magnitude as the coated, 26Ga sensing needle, advances through the cancerous tissue and into normal tissue, and 2) a comparison of static measured impedance magnitude from cancerous tissue and normal muscle. The cancerous tissue shows measured impedance magnitude in the range of 1,000 Ohms to 2,000 Ohms while normal muscle shows measured impedance between 2,000 Ohms and 5,000 Ohms.

Exemplary Additional Discussion

As discussed herein, the exemplary insertion device/apparatus can be used in various injection procedures which require injection into specific tissues such as fat, septae, or the intradermal space. The exemplary insertion device/apparatus can also be used in cardiac catheterization (e.g., trocars), which can be used to introduce catheters into a blood vessel (e.g., an artery, a vein, etc.). The exemplary insertion device/apparatus can be used in various other applications including, but not limited to, anesthesia procedures, as well as during ablation procedures to determine when the ablation electrodes are within a specific tissue type. The exemplary insertion device/apparatus can be integrated into a catheter to be used inside the body. For example, the insertion device/apparatus can be used as part of a transceptal needle, which can be used during minimally invasive cardiac procedures. Any suitable fabrication procedure/technique can be used to produce printed circuit boards can be used to produce the exemplary insertion device/apparatus structure. Exemplary electrodes can be rigid or flexible.

Figure 19A:
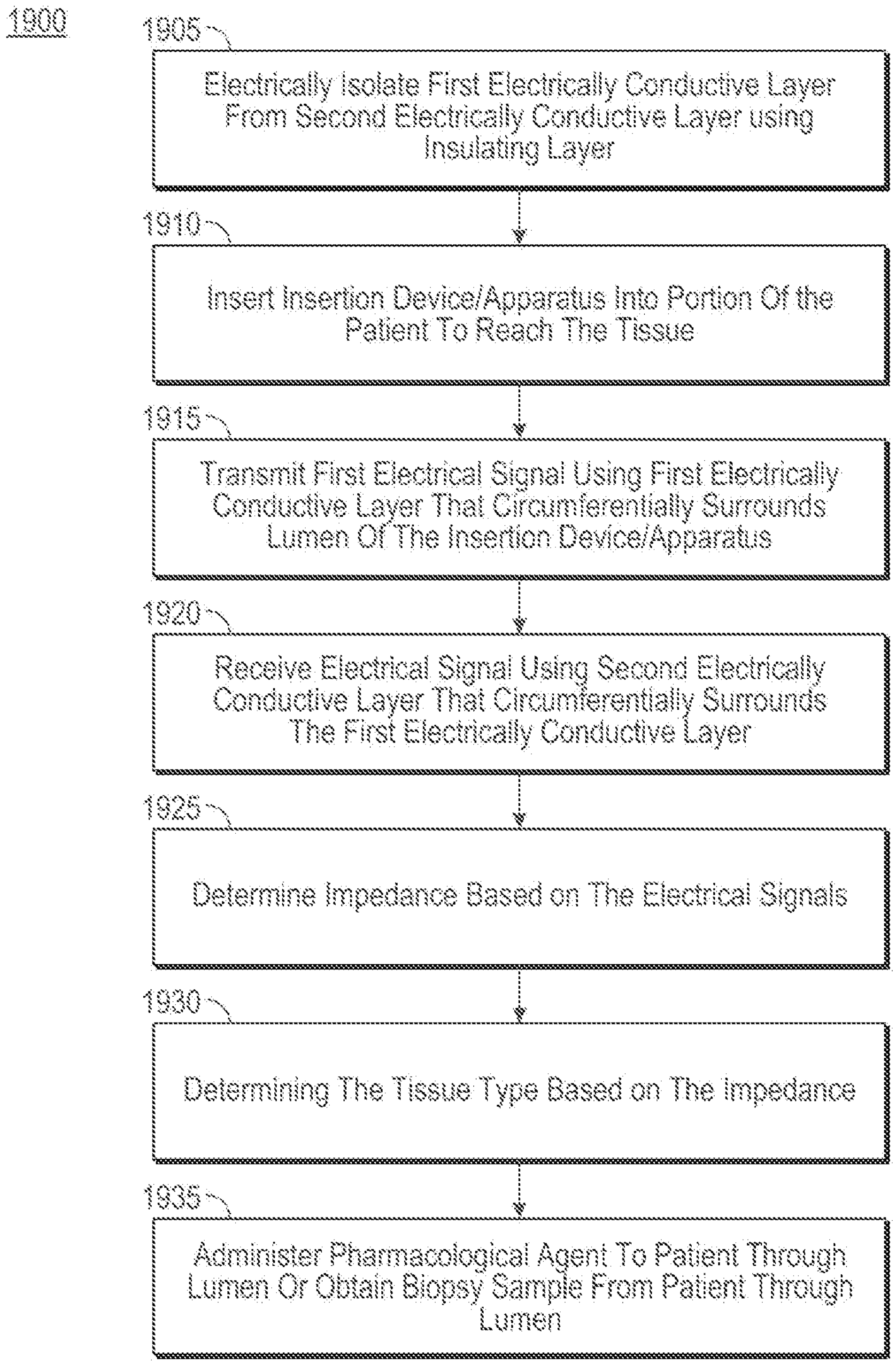
FIGS. 19A-19D are exemplary flow diagrams of exemplary methods of determining a type of a tissue of a subject using the exemplary insertion device/apparatus.
Figure 19B:
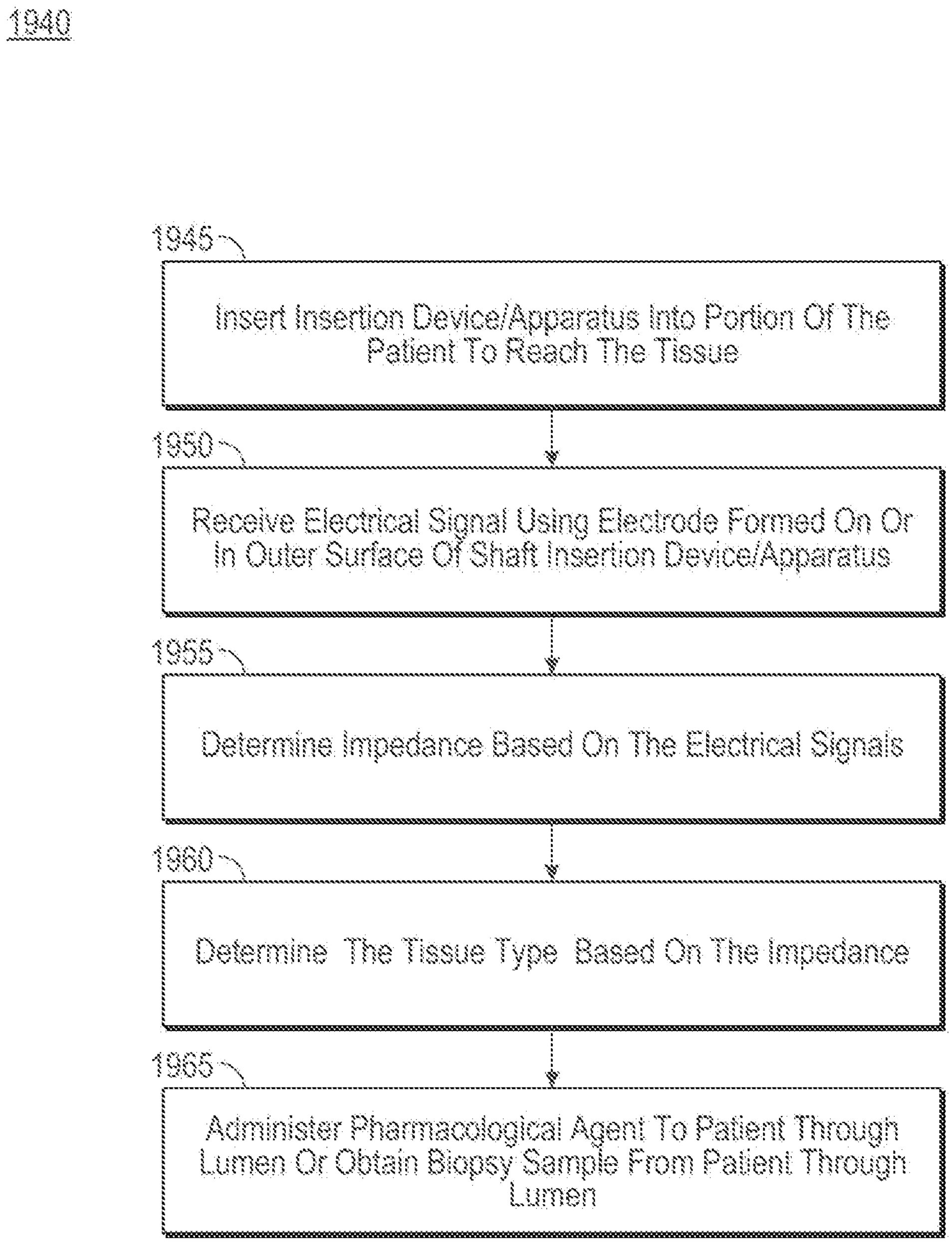
Figure 19C:
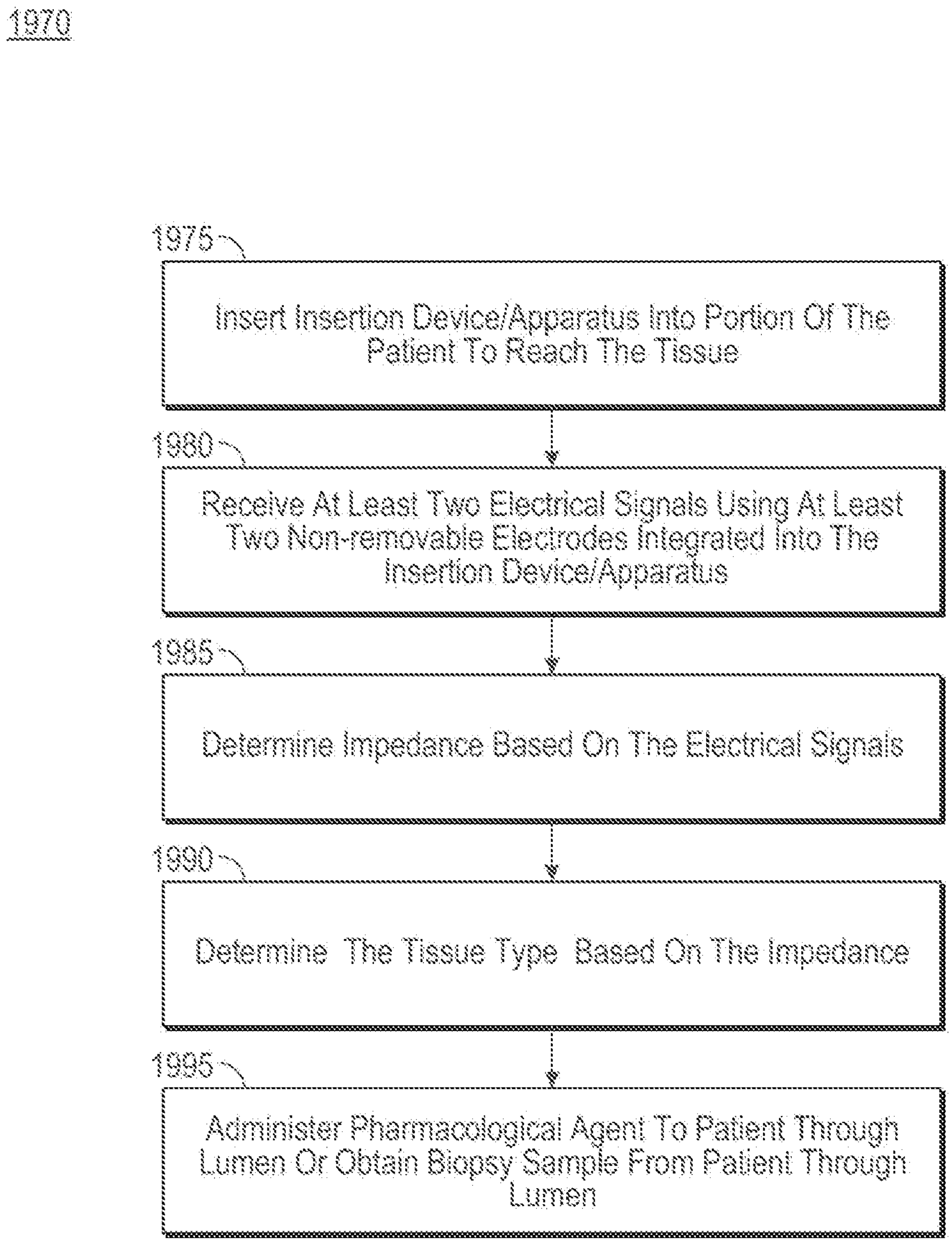

FIGS. 19A-19C are exemplary flow diagrams of exemplary methods 1900, 1940, and 1970 for determining a type of a tissue of a subject using the exemplary insertion device/apparatus. For example, as shown in FIG. 19A, at procedure 1905, a first electrically conductive layer in the insertion device/apparatus can be electrically isolated from a second electrically conductive layer in the insertion device/apparatus using an insulating layer. At procedure 1910, the insertion device/apparatus can be inserted into the portion of the subject to reach the tissue. At procedure 1915, a first electrical signal can be transmitted and/or received using the first electrical conductive layer, which circumferentially surrounds a lumen of the insertion device/apparatus. In one exemplary embodiment of the present disclosure, the AC wave form that was generated can pass through analog conditioner circuitry to the electrode(s). Impedance measurement of tissue between electrodes can impact the wave form which can then be measured using exemplary digital processing techniques (e.g., synchronous detection, 4fs, etc.) At procedure 1920, the electrical signal (or another electrical signal) can be received from the second electrically conductive layer, which circumferentially surrounds the first electrically conductive layer. At procedure 1925, an impedance can be determined based on the ratio of the transmitted and received electrical signals. At procedure 1930, the tissue type can be determined based on the impedance. In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1935, any material and/or substance (e.g., a pharmacological agent, drug, filler, therapeutics, biologics, cellular materials, stem cells, genetic materials, immunotherapy agents, etc.) can be administered to the subject through the lumen or a biopsy sample and/or other fluid, tissue, cells or material can be obtained from the subject through the lumen.

As shown in the flow diagram of FIG. 19B, at procedure 1945, the insertion device/apparatus can be inserted into the portion of the subject to reach the tissue. At procedure 1950, an electrical signal can be transmitted and/or received using an electrode formed on or in an outer surface of the shaft of the insertion device/apparatus. At procedure 1955, an impedance can be determined based on the electrical signal. At procedure 1960, the tissue type can be determined based on the impedance. Either the magnitude and/or phase components of the impedance can be used to distinguish the tissue type by comparing the measured values with known values (e.g., at one frequency or a narrow band of frequencies). In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1965, any material and/or substance (e.g., a pharmacological agent, drug, filler, therapeutics, biologics, cellular materials, stem cells, genetic materials, immunotherapy agents, etc.) can be administered to the subject through the lumen or a biopsy sample and/or other fluid, tissue, cells or material can be obtained from the subject through the lumen.

As shown in the flow diagram of FIG. 19C, at procedure 1975, the insertion device/apparatus can be inserted into the portion of the subject to reach the tissue. At procedure 1980, at least two electrical signals can be received using at least two non-removable electrodes integrated into the insertion device/apparatus. In one exemplary embodiment of the present disclosure, the AC wave form that was generated can pass through analog conditioner circuitry to the electrodes. Impedance measurement of tissue between electrodes can impact the wave form which can then be measured using exemplary digital processing techniques (e.g., synchronous detection, 4fs, etc.) At procedure 1985, an impedance can be determined based on the at least two electrical signals. At procedure 1990, the tissue type can be determined based on the impedance. In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1995, any material and/or substance (e.g., a pharmacological agent, drug, fluid (e.g. blood, plasma, and other fluids typically administered through a needle), filler, therapeutic agents, cellular materials, stem cells, cells (e.g. adipocytes, lymphocytes, etc.), tissues (e.g. adipose tissue, bone marrow, etc.), genetic materials, immunotherapy agents, etc.) can be administered to the subject through the lumen or a material, tissue, cells, fluid and/or a biopsy sample can be obtained from the subject through the lumen.

Figure 19D:
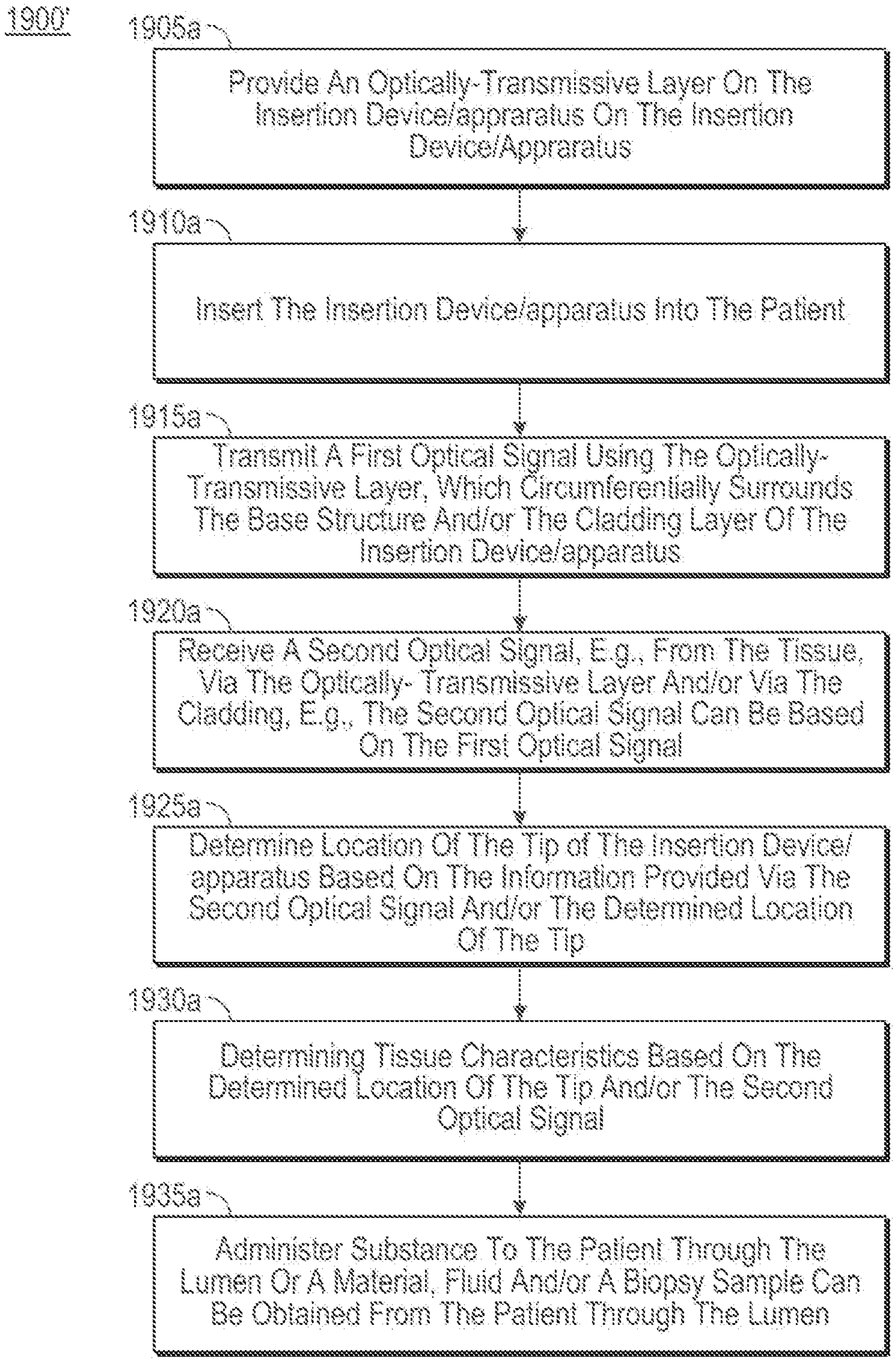

FIG. 19D shows an exemplary flow diagram of an exemplary method 1900' for determining a characteristic of a tissue of a patient, as well as a position of a tip of the device with respect to the tissue, using the exemplary insertion device/apparatus. For example, as shown in FIG. 19D, at procedure 1905*a*, an optically-transmissive layer is provided on the insertion device/apparatus, e.g., on the base structure and/or on the cladding layer. At procedure 1910*a*, the insertion device/apparatus can be inserted into the portion of the patient to reach the tissue. At procedure 1915*a*, a first optical signal can be transmitted-using the optically-transmissive layer, which circumferentially surrounds the base structure and/or the cladding layer of the insertion device/apparatus. At procedure 1920*a*, a second optical signal can be received, e.g., from the tissue, via the optically-transmissive layer and/or via the cladding, whereas the second optical signal is based on the first optical signal. At procedure 1925*a*, a location of the tip of the insertion device/apparatus can be determined based on the information provided via the second optical signal and/or the determined location of the tip. At procedure 1930*a*, the tissue characteristics can be determined based on the determined location of the tip and/or the second optical signal. In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1935*a*, any material and/or substance (e.g., a pharmacological agent, drug, filler, therapeutics, cellular materials, stem cells, genetic materials, immunotherapy agents, etc.) can be administered to the patient through the lumen or a material, fluid and/or a biopsy sample can be obtained from the patient through the lumen.

Figure 20A:
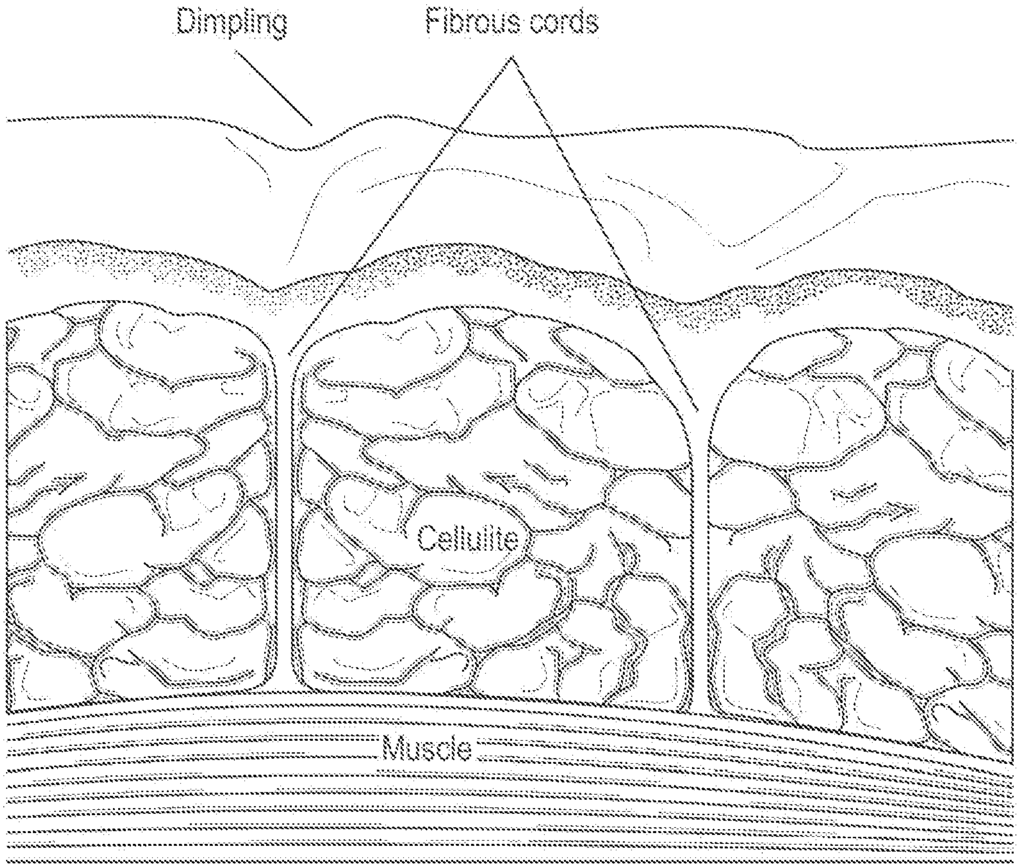
FIGS. 20A and 20B are illustration of an exemplary treatment of edematous fibrosclerotic panniculopathy (EFP), commonly known as cellulite, through the injection of a particular substance in accordance with the exemplary embodiment of the present disclosure.
Figure 20B:
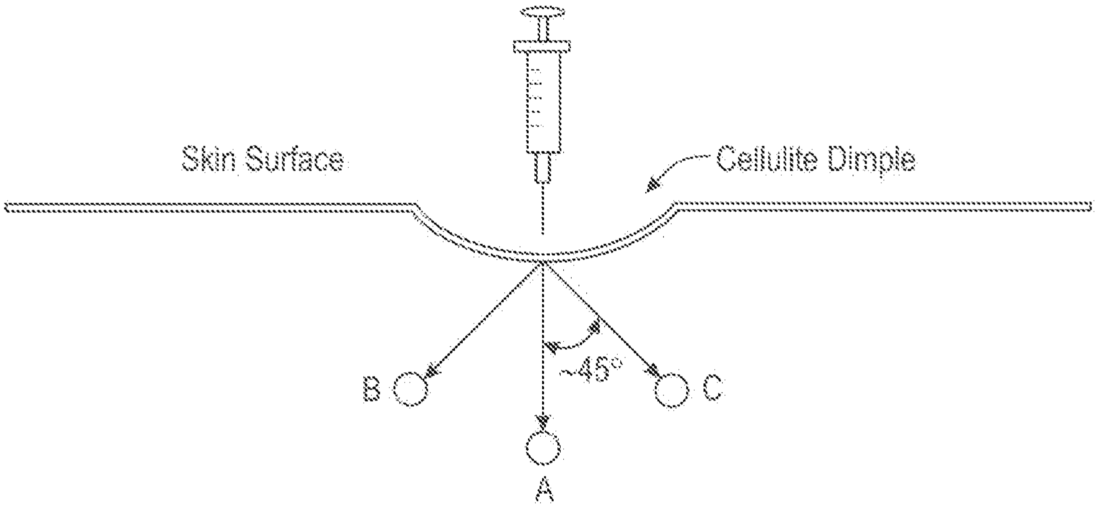

In accordance with various exemplary embodiments of the present disclosure, it is beneficial to utilize the exemplary insertion device/apparatus to perform other exemplary procedures which are significantly benefitted with the identification of the tissue into which certain materials and/or substances are being inserted and/or injected. FIG. 20A shows an exemplary illustration of the differ layers and sections within a tissue sample, and FIG. 20B provide and exemplary illustration of an application of the exemplary embodiments of the insertion devices/apparatuses according to the present disclosure which can be used the treatment of edematous fibrosclerotic panniculopathy (EFP), commonly known as cellulite, by an injection of an enzyme into the tissue, such as, e.g., collagenase. For example, the enzyme can be injected locally into the fat in order to break down the fibrous cords, also called septae which are responsible for causing the dimpled appearance of cellulite. The exemplary insertion device/apparatus according to the exemplary embodiments of the present disclosure incorporating and/or utilizing the exemplary impedance sensing as described herein can be used to provide an indication and/or direction of when the tip of the insertion device/apparatus is within the fat before the injection. This beneficially facilitates the enzyme to be injected close to the septae. The exemplary injection procedure is shown in FIG. 20B.

Figure 20C:
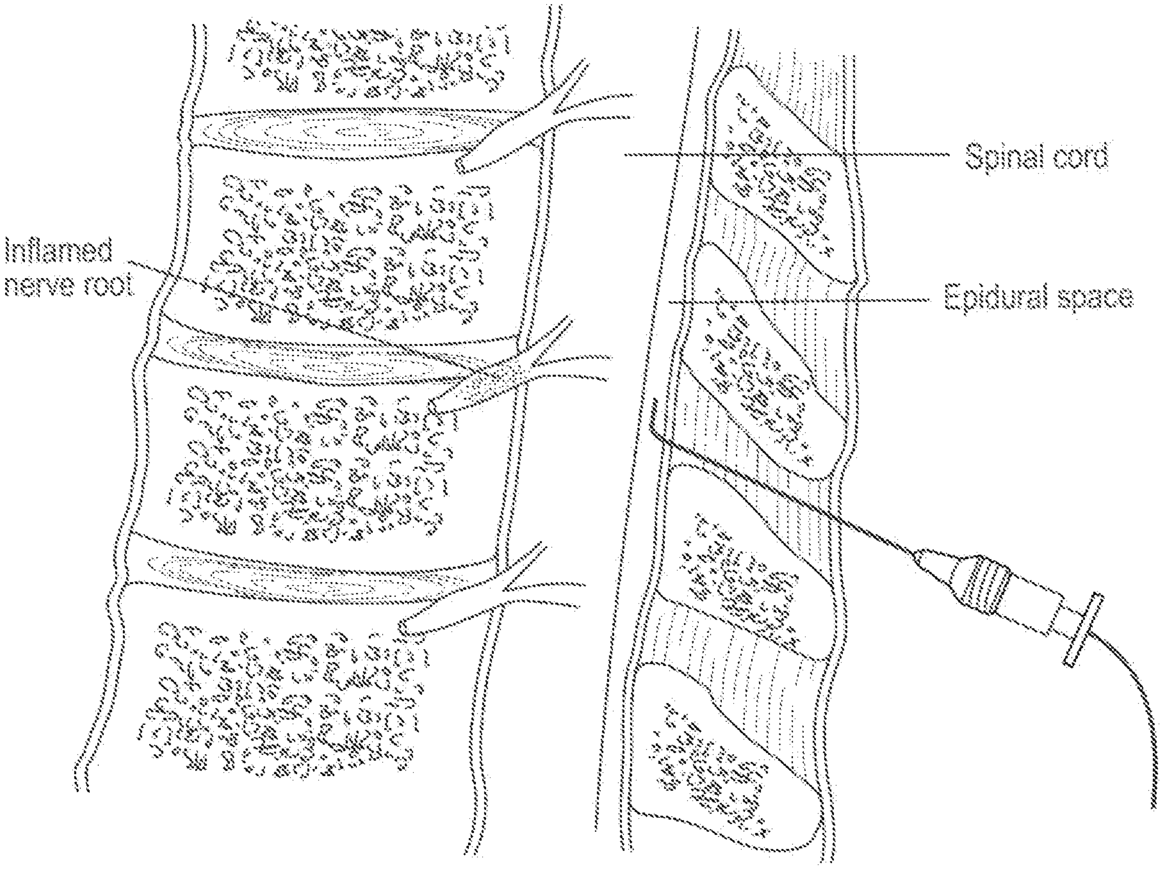
FIG. 20C is an illustration of an exemplary procedure involving a spinal injection performed to alleviate the source of pain or discomfort, in accordance with the exemplary embodiment of the present disclosure.

FIG. 20C illustrates an exemplary procedure involving a spinal puncture, which can be performed to diagnose the source of back, leg, neck, or arm pain (diagnostic) and also to relieve pain (therapeutic). The exemplary insertion devices/apparatus incorporating impedance sensing functionality and/or configurations can be used to provide a user with an indication of when the tip of such exemplary insertion devices/apparatus is within the epidural space. The exemplary insertion devices/apparatuses (and/or a system connected thereto) can be programmed or otherwise configured to detect the unique impedance signature and/or information indicative or representative of the epidural fluid. The exemplary insertion devices/apparatus also be used for an injection of various substances into the tissue, such as steroids into joints in the spine such as the sacroiliac joint, when the exemplary insertion devices/apparatus determines that a certain tissue type or an opening is reached.

Figure 20D:
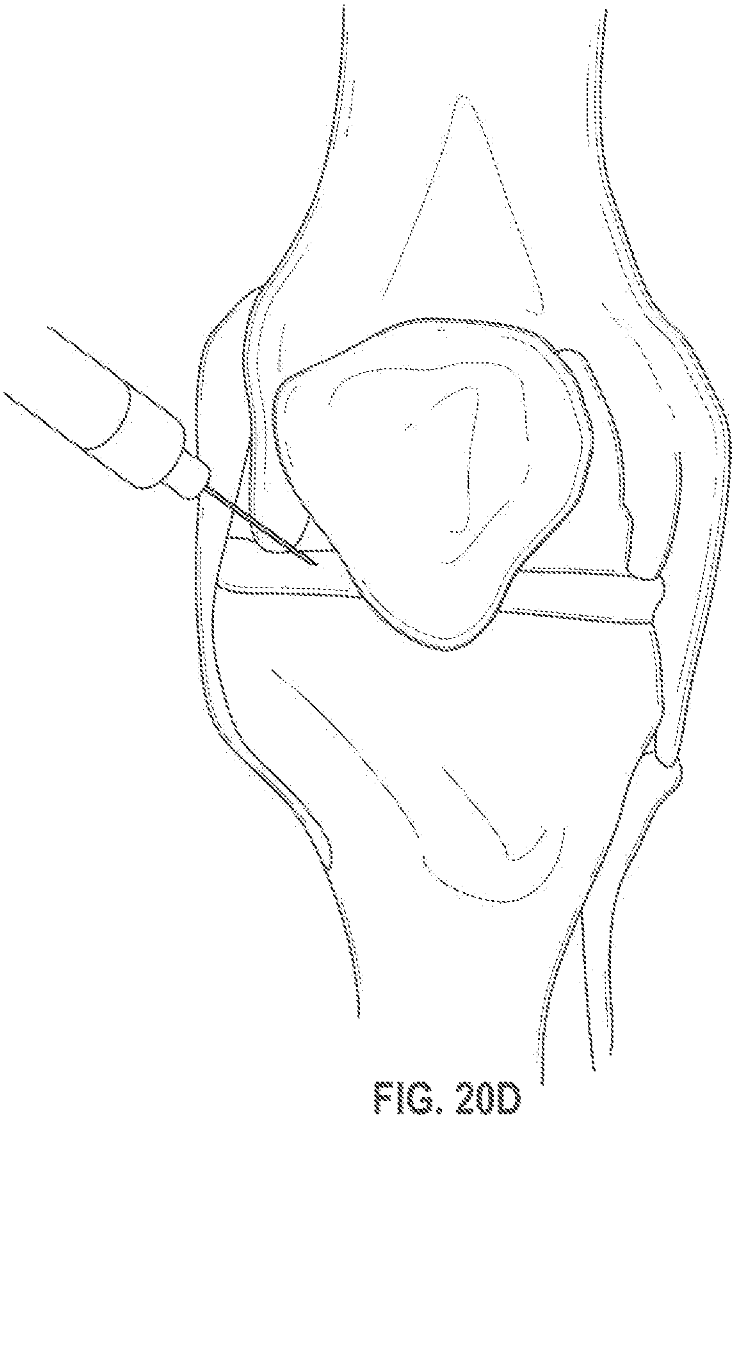
FIG. 20D is an illustration of an exemplary procedure involving an injection of substances (e.g., such as platelet rich plasma (PRP) or hyaluronic acid (HA)) into the synovial space in accordance with the exemplary embodiment of the present disclosure.

FIG. 20D shows an illustration of an exemplary procedure involving an injection of substances (such as, e.g., platelet rich plasma (PRP)) into synovial space of joints (e.g., knees, elbows, etc.), in accordance with the exemplary embodiment of the present disclosure. As illustrated in FIG. 20D, the exemplary insertion device/apparatus incorporating and/or utilizing the exemplary impedance sensing as described herein can provide an indication of when the tip of the exemplary insertion apparatus is within the space. The exemplary insertion devices/apparatuses (and/or a system connected thereto) can be programmed or otherwise configured to detect the unique impedance signature and/or information indicative or representative of synovial fluid or cartilage.

Figure 23A:
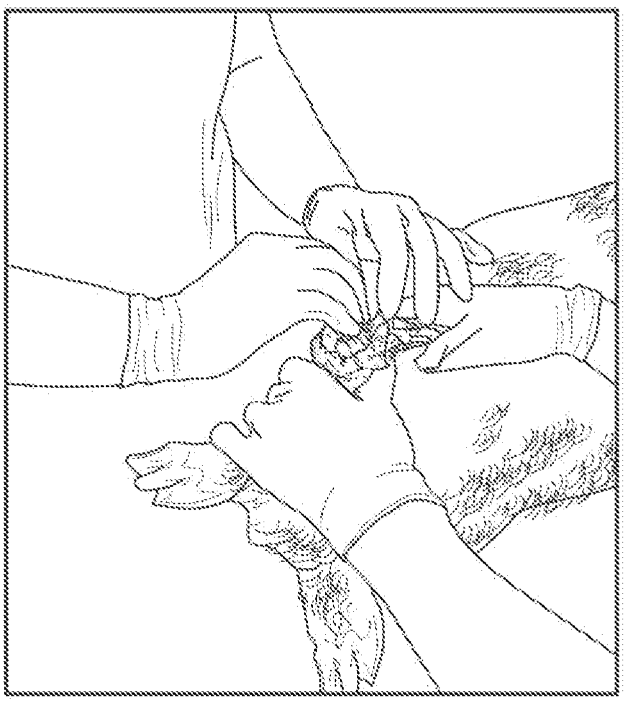
FIG. 23A is an exemplary image showing the exemplary device being inserted into a joint, according to an exemplary embodiment of the present disclosure.
Figure 23B:
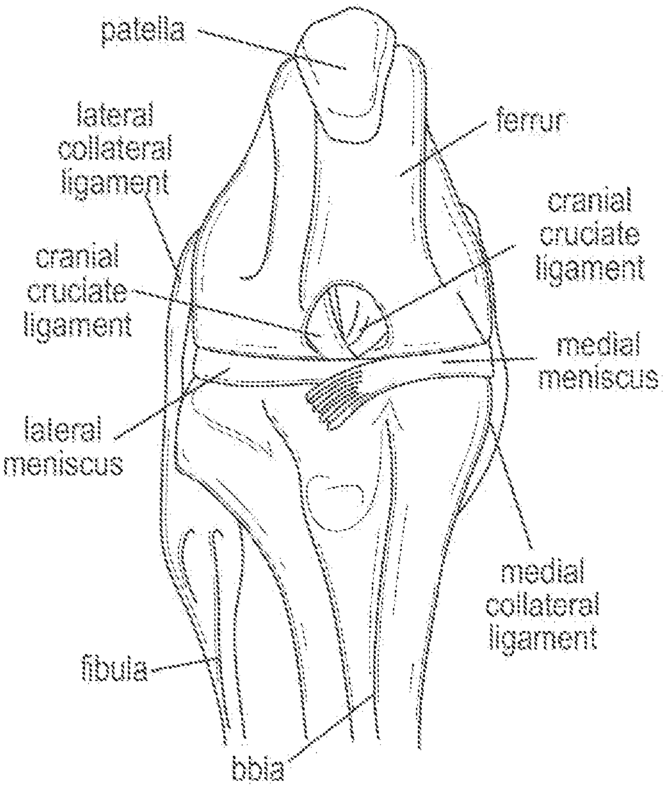
FIG. 23B is an exemplary diagram of a joint, according to an exemplary embodiment of the present disclosure.
Figure 23C:
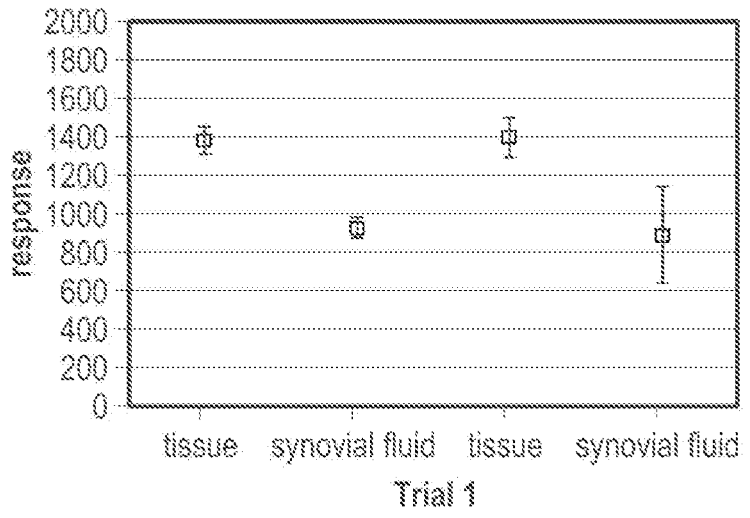
FIG. 23C is a set of exemplary graphs illustrating real-time feedback for two trials, according to an exemplary embodiment of the present disclosure.
Figure 23C:
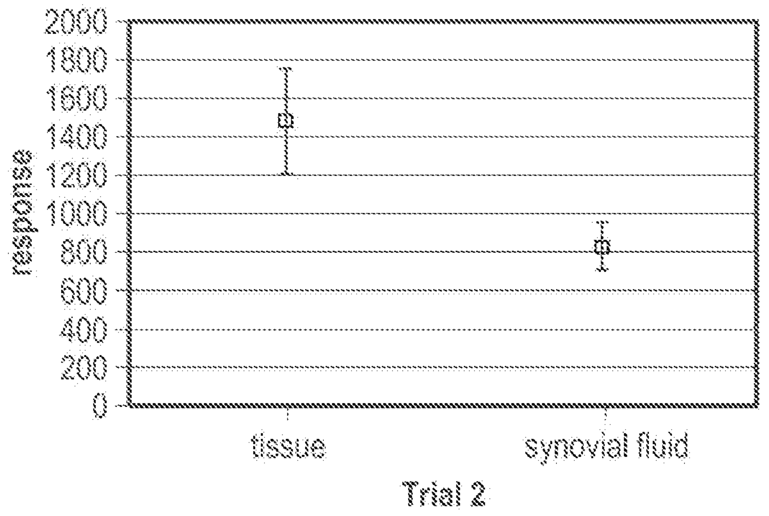

FIG. 23A shows an exemplary image showing the exemplary device being inserted into a joint, according to an exemplary embodiment of the present disclosure. FIG. 23B shows an exemplary diagram of a joint, according to an exemplary embodiment of the present disclosure. An incision in the skin can be made using surgical scissors to the expose stifle joint, the animal equivalent of a knee. The needle can be inserted through soft tissue at an angle into the stifle joint, primarily by feel. After holding the needle stationary, it can be advanced to touch cartilage/bone. The needle can then be slowly withdrawn. FIG. 23C shows a set of exemplary graphs illustrating real-time feedback for two trials, according to an exemplary embodiment of the present disclosure. As the needle tip passes through different biological tissues and fluids, signals from the needle can be used to sense changes in very specific electrical properties. An exemplary procedure can be used to provide immediate response with real-time user feedback. For example, feedback can be provided via any suitable wired or wireless communication medium (e.g., Wi-Fi, Bluetooth, etc.) to an electronic device (e.g., a smart phone, tablet, computer, etc.) or to a LED light embedded in the needle hub.

Further, for example, the exemplary insertion devices/apparatuses described herein can be utilized in various cellulite treatment applications based on the detection of the unique impedance signature and/or information of the tissue. Some of such exemplary applications are described in, e.g., U.S. Patent Publication No. 2018/0250217 and Michael P. Goldman et al., "Phase 2a, randomized, double-blind, placebo-controlled dose-ranging study of repeat doses of collagenase *Clostridium histolyticum* for the treatment of edematous fibrosclerotic panniculopathy (cellulite)", Poster Presented at the 73rd Annual Meeting of the American Academy of Dermatology, Mar. 20-24, 2015; San Francisco, California, the entire disclosures are incorporated herein by reference.

In a further exemplary embodiment of the present disclosure, the exemplary insertion device/apparatus can be configured to be used to extract or aspirate bodily fluids, cells or tissues from a body, including, e.g., a subject. In one example, a syringe and needle can be used as the insertion device/apparatus to extract or aspirate materials, fluids, solutions, compounds, etc. which are well-known in the medical, dental and veterinary fields in general. Indeed, such exemplary utilization of the insertion device/apparatus according to the exemplary embodiments of the present disclosure can facilitate a greater precision and safety for the subject. Non-limiting examples of use of the exemplary insertion device/apparatus can include phlebotomy procedures used to draw blood samples, spinal taps used to extract cerebrospinal fluid from the spinal column, joint taps used to extract synovial fluid, needle biopsies to aspirate a sample of cells or tissue and the aspiration of bone marrow samples for typing and transplantation.

One having ordinary skill in the art may readily understand, based on the review of the present disclosure, that such exemplary embodiment of the insertion device/apparatus may be used in the same or similar manner as other methods described in the present application in which materials, cells, compounds, agents, enzymes, fillers, fluids, etc. are inserted into a body at certain determined tissues types, and instead by extracting or aspirating the targeted fluid, materials, compounds, agents, enzymes, fillers, fluids, etc. This can be done, in one non-limiting example, by—instead of pushing the syringe plunger to expunge a fluid or other materials—pulling back on the syringe plunger to create suction or a vacuum that draws the targeted fluid, materials, cells, compounds, agents, enzymes, fillers, fluids, etc. into the syringe (e.g., in a reverse direction).

According to various exemplary embodiments of the present disclosure, the insertion device/apparatus and variants thereof described herein can include openings provided, e.g., in the cladding to act as side-looking "windows" to facilitate optical radiation to be transceived there through. Additionally, optical fibers can be provided along the base structure, and the optical radiation can be provided through such optical fibers, together with or separately from the core 120*z*, 120', 120" and/or the cladding 170.

According to the exemplary embodiments of the present disclosure, exemplary materials that can be used for providing and/or forming the coating/core and/or the cladding can include optically conductive/transmissive materials that can be applied to the target structures. The optical transmission coating can be applied by spraying, dipping, painting, sputtering, vapor deposition, etc. The exemplary multi-layer structure (e.g., multiple core/cladding combinations) can also be produced using, e.g., a co-extrusion process. Exemplary materials described herein can include polymers such as, e.g., urethane, acrylic, polycarbonate, polystyrene, cyclic olefin polymers or copolymers, as well as copolymers combining materials. Silicones can also be utilized. Glasses or ceramic coatings can be formed using a sol gel process with post-processing such as sintering or by applying a material in powder form and then using a melt quenching process. Further exemplary materials can include silica glass, aluminum oxide among others. The exemplary materials can be selected based on the process temperature and compatibility with the target structure. For example, a glass and/or ceramic that utilizes sintering for application may be difficult to apply to a polymer as the temperatures may be above the polymer glass transition temperatures. However, other exemplary materials can be easily utilized which are not effected by such temperature, and are within the scope of the present disclosure.

The material used for the cladding can include any material with a lower refractive index than the base transmissive coating. Such exemplary materials can include any of those listed above which have a slightly lower index than the material used for the core/coating. The cladding may also include or be a reflective material such as, e.g., a metallic coating.

The exemplary embodiments of the present disclosure can be used in, and not certainly limited to, the following exemplary applications:

Tissue Sensing—Guidance, Diagnosis, Imaging

Using the exemplary embodiments of the insertion device/apparatus described herein, it is possible to utilize light reflected and/or provided from the tissue to characterize the type of tissue by comparison with a database of known spectra. Exemplary applications can include, e.g., a) guidance of the insertion device/apparatus by determining the type of tissue provided at or near the tip of the insertion device/apparatus, 2) diagnosis of the tissue by determining whether the information regarding the tissue identifies the tissue to be normal or abnormal (e.g., oncology or any clinical area looking at live/dead tissue). It is also possible to select various optical radiations based on consideration of the environment (e.g., tissue type, presence of blood, etc.) and/or consideration of depth of penetration.

Embolization—Fibroids, Tumors, Cerebral Aneurism, Hemostasis, Family Planning, Etc.

The exemplary base structure with the central lumen (e.g., open, tubular structure such as a needle or catheter) can be used to deliver a gel or cross-linkable monomer. The exemplary optical coatings (e.g., waveguides) described herein can be used to deliver the optical radiation with known characteristics based on the agent to polymerize the delivered material. Thus, it is possible to achieve controlled polymerization, which overcomes the deficiencies of the existing devices, e.g., beads or other devices which are used to embolize structures which are difficult to move after placement. Further, the exemplary integrated delivery insertion device/apparatus according to the various exemplary embodiments of the present disclosure can reduce procedure time and accuracy as there is no need to exchange or re-position multiple devices.

Photodynamic Therapy—Cancer, Etc.

The exemplary base structure with the central lumen (e.g., open, tubular structure such as a needle or catheter) can be used to deliver a photosensitizing agent. For example, exemplary optical coatings (e.g., waveguides, cores, etc.) can be used to deliver the optical radiation directly to the area of the tissue where the photosensitizing agent was delivered with appropriate wavelength, power, etc. PDT typically relies on illumination using external light sources or lasers which limits treatment to tissue depths of only ⅓$^{rd}$ of an inch or less. The exemplary embodiments of the present disclosure facilitate delivery and treatment of deeper structures, anywhere the delivery/insertion device can penetrate, thus providing precise intra-tumor drug and light delivery.

Fillers—In-Situ Polymerization

The exemplary base structure with the central lumen (e.g., open, tubular structure such as a needle, cannula or catheter) can be used to deliver a filler pre-cursor—gel or cross-linkable monomer. For example, exemplary optical coatings (e.g., waveguides, cores, etc.) can be used to deliver the optical radiation with known characteristics based on the agent to polymerize the material. Fillers are typically delivered in final form which are viscous and difficult to deliver. Delivering a monomer or non-cross-linked gel, as described according to the exemplary embodiments of the present disclosure facilitates delivery of a less viscous material and also provide a clinician with the ability to shape the structure and then polymerize to stabilize (shape).

Yet Further Exemplary Embodiments

Figure 21A:
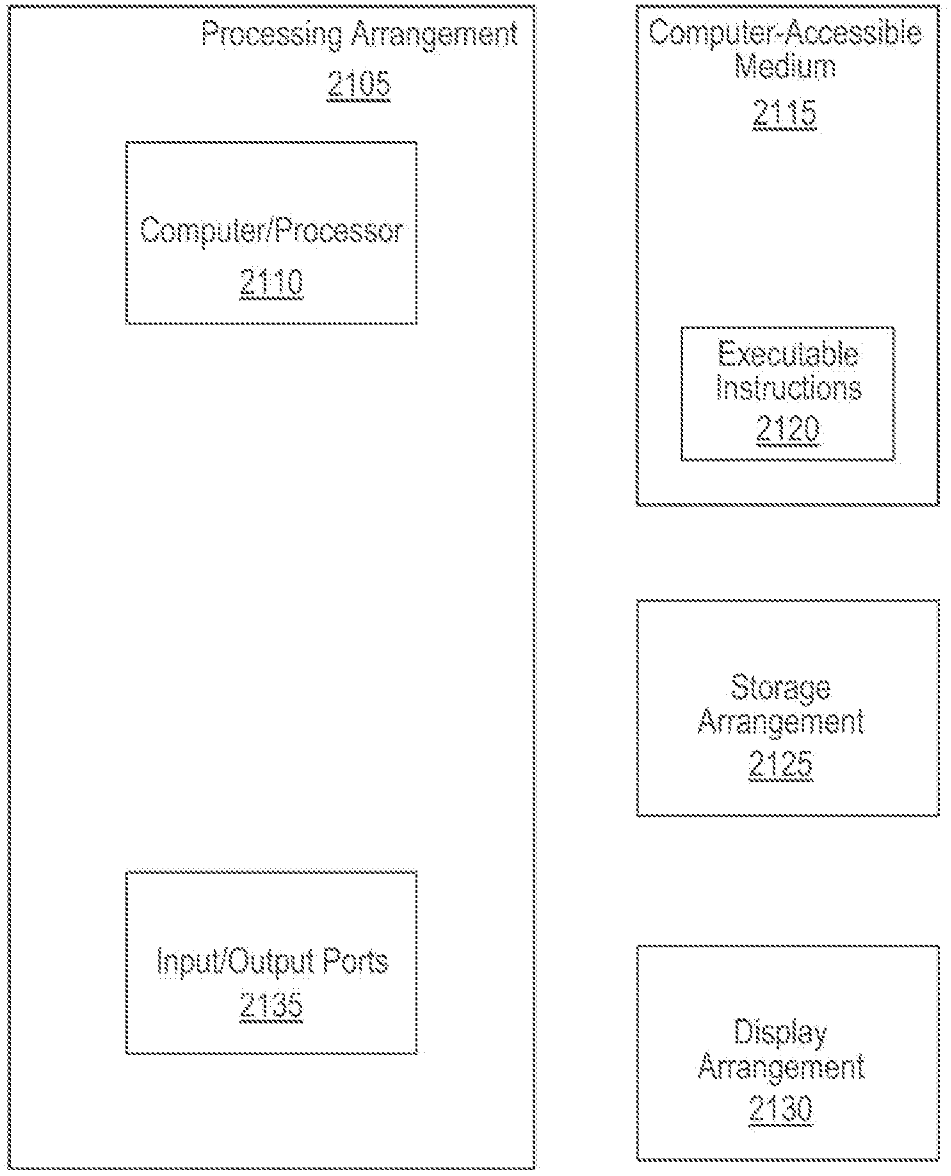
FIG. 21A is an illustration of an exemplary block diagram of an exemplary system in accordance with certain exemplary embodiments of the present disclosure.

FIG. 21A shows a block diagram of yet another exemplary embodiment of a system according to the present disclosure. For example, exemplary procedures in accordance with the present disclosure described herein can be performed by a processing arrangement and/or a computing arrangement 2102. Such processing/computing arrangement 2102 can be, for example entirely or a part of, or include, but not limited to, a computer/processor 2104 that can include, for example one or more microprocessors, and use instructions stored on a computer-accessible medium (e.g., RAM, ROM, hard drive, or other storage device).

As shown in FIG. 21A, for example a computer-accessible medium 2106 (e.g., as described herein above, a storage device such as a hard disk, floppy disk, memory stick, CD-ROM, RAM, ROM, etc., or a collection thereof) can be provided (e.g., in communication with the processing arrangement 2102). The computer-accessible medium 2106 can contain executable instructions 2108 thereon. In addition, or alternatively, a storage arrangement 2010 can be provided separately from the computer-accessible medium 2006, which can provide the instructions to the processing arrangement 2102 so as to configure the processing arrangement to execute certain exemplary procedures, processes and methods, as described herein above, for example.

Further, the exemplary processing arrangement 2102 can be provided with or include an input/output arrangement 2114, which can include, for example a wired network, a wireless network, the internet, an intranet, a data collection probe, a sensor, etc. As shown in FIG. 21, the exemplary processing arrangement 2102 can be in communication with an exemplary display arrangement 2112, which, according to certain exemplary embodiments of the present disclosure, can be a touch-screen configured for inputting information to the processing arrangement in addition to outputting information from the processing arrangement, for example. Further, the exemplary display 2112 and/or a storage arrangement 2110 can be used to display and/or store data in a user-accessible format and/or user-readable format.

Figure 21B:
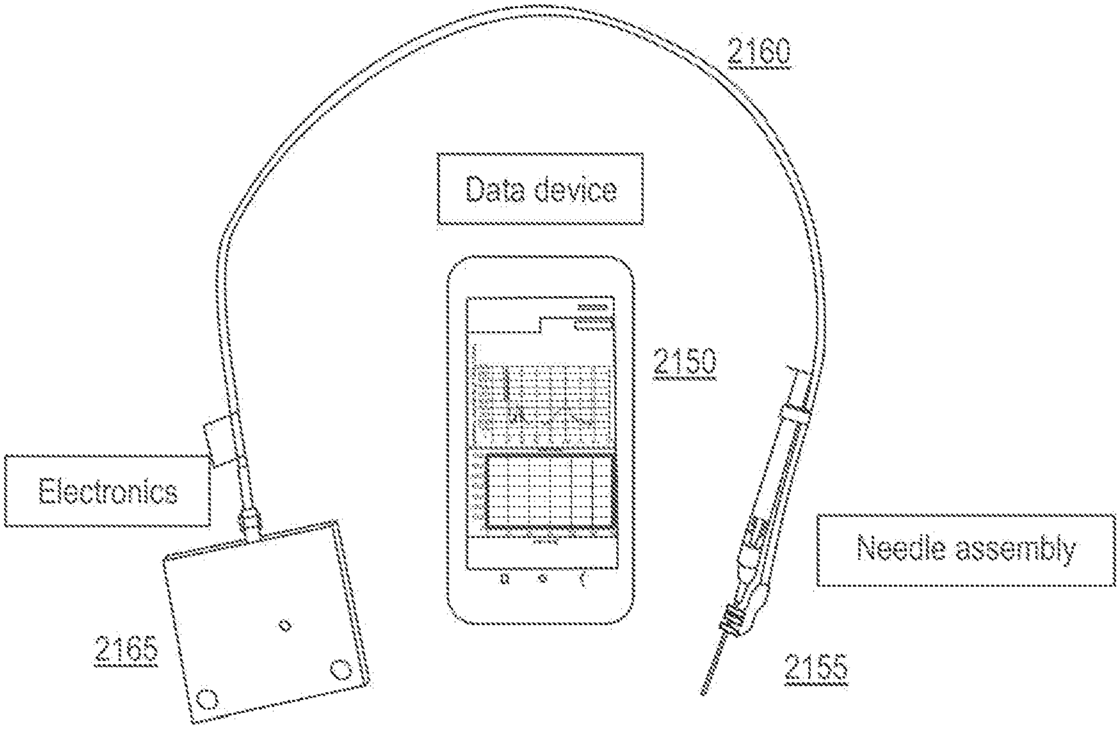
FIG. 21B is an illustration of an exemplary device incorporating the exemplary insertion apparatus tethered to an external electronics package to infer impedance along with a data device connected wirelessly via Bluetooth to a data device which displays and records data, according to an exemplary embodiment of the present disclosure.

FIG. 21B is a photograph of an exemplary embodiment of the exemplary system described herein above with reference to FIG. 21A. For example, the exemplary system incorporates electronics housed in a box which can be a computing device 2150 or a data device, including but not limited a mobile phone, tablet, etc. separate from the exemplary insertion device/apparatus 2160 (various exemplary embodiments described herein) and connected using a coaxial cable 2170 which can be terminated with a connector that can provide an electrical contact with both the outer electrical coating and the hypodermic needle tubing of the exemplary insertion device/apparatus 2160. The electronics incorporate an nRF52840 System-on-Chip (SoC) is used to perform the analog to digital conversion, digital signal processing and wireless communication. The electronics can communicate wirelessly with the computing device 2150 or data device using wireless communication protocol(s), e.g., Bluetooth. The computing device 2150 can receive data, provide a real time display of the measured impedance (both magnitude and angle), and/or record the data.

Figure 21C:
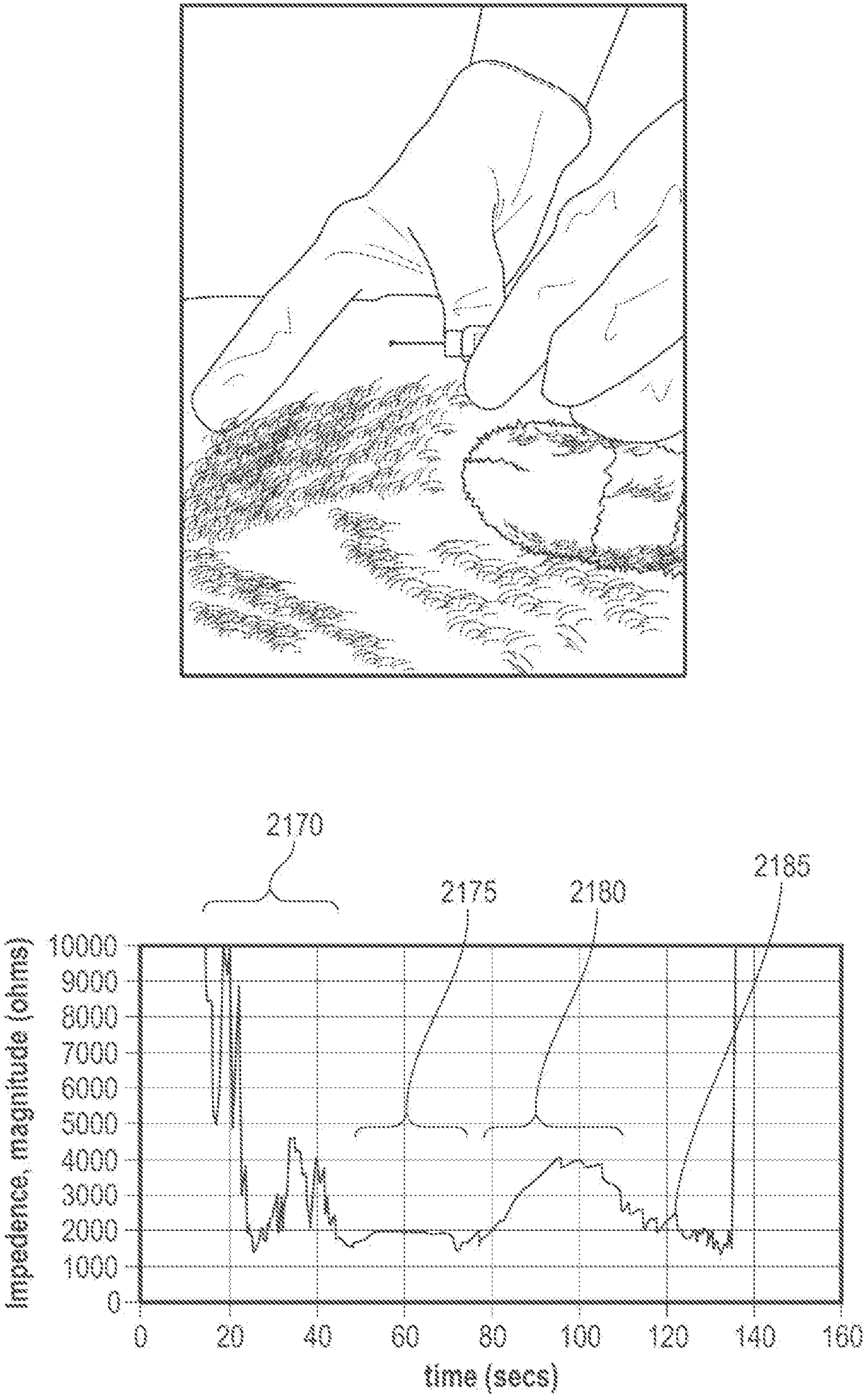
FIG. 21C is an illustration of exemplary data collected during needle insertion into a rabbit femoral vein using a device with external electronics, according to an exemplary embodiment of the present disclosure.

FIG. 21C illustrates a measured response from the system during insertion into the inner thigh of a New Zealand White rabbit. The exemplary insertion apparatus (e.g., a needle—exemplary structures of which is described herein) was inserted through the skin and then guided into the femoral vein which was visible just below the skin. Blood could be seen inside the needle hub, verifying that the needle was inside the vein. The exemplary insertion apparatus was then held in place for several seconds and then advanced through the opposing vein wall into the underlying muscle. Finally, the exemplary insertion apparatus was withdrawn.

As shown in FIG. 21C which illustrates exemplary data, the measured impedance magnitude showed continuous changes as the needle was advanced through tissue and then into the femoral vein. The recorded values remained high, generally above 2,000 Ohms except for a brief time during which the needle may have momentarily contacted a blood vessel. The data for the initial insertion through skin into muscle, possible brief passage through vessel is provided in FIG. 21B for period 2170. As the needle entered the femoral vein (e.g., the needle held stationary), the measured impedance magnitude dropped to a relatively steady value between 1,500 Ohms and 2,000 Ohms for period 2175. As the needle was advanced through the vein and into muscle, the measured impedance magnitude increased above 2,000 Ohms, as provided in period 2180. As the needle was withdrawn, the measured impedance magnitude decreased briefly as the needle tip passed back through the femoral vein and then increased as the needle was pulled out of the leg, as provided in period 2185.

These exemplary results shown in FIG. 21C illustrate how an exemplary system may behave during a clinical application such as injection of a filler. In one example, the user can insert the exemplary insertion apparatus (e.g., needle) into a patient's/subject's face. A small AC current passes from the hypodermic needle body through tissue or fluid in contact with the tip and then to the outer coating. The electronics infer impedance from the changes in the current caused during passage through the tissue or fluid. During initial insertion, the measured impedance magnitude will remain high. If the needle tip enters a blood vessel in the face, the measured impedance magnitude will show a distinct drop. The electronics may be designed to detect when the measured impedance magnitude is within a defined range, for example, between 1,000 Ohms and 2,000 Ohms. If the measured impedance magnitude is within this exemplary range, the exemplary electronics and/or the exemplary electronic computing device as described herein below can provide, e.g., an alert through the data device, for example an audible tone or a visual cue such as a light. Changes in, e.g., impedance angle or phase may also be used. The user may use the alert as an indication that the needle is in a blood vessel and/or that it may be unsafe to inject a filler.

This exemplary information can be used in other procedures, for example, during phlebotomy procedures, IV line placement, or catheter introduction. The alert or another audio and/or visual indication can be used to let a user know that the needle is inside a vessel and that it is safe to proceed.

Figure 21D:
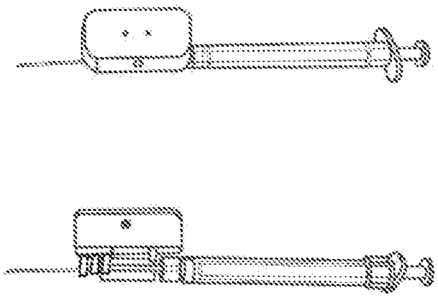
FIG. 21D is an illustration of the operation of an exemplary integrated system using lights to provide information to a user, according to an exemplary embodiment of the present disclosure.
Figure 21D:
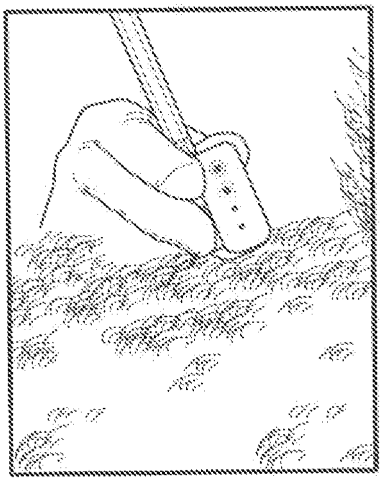
Figure 21D:
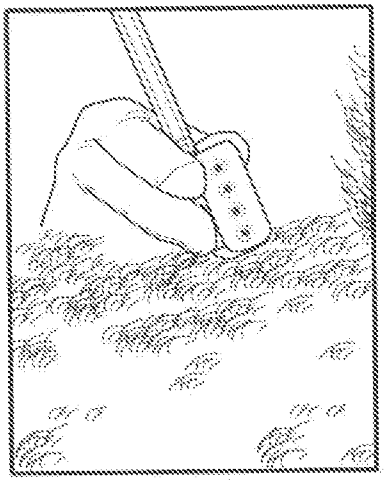
Figure 21D:
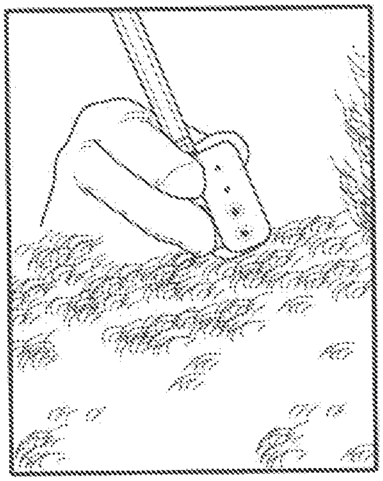

FIG. 21D illustrates a set of photographs of an exemplary embodiment of the exemplary system which integrates the electronics into the exemplary needle using light to provide a user with an alert. The exemplary electronics package clipped onto the exemplary needle making electrical contact with the central needle body as well as the outer conductive coating (image 2191), as described in various exemplary embodiments provided herein. The exemplary electronics shown in FIG. 21D incorporate, e.g., a MSP430FR2355TRHA microcontroller by Texas Instruments. The exemplary microcontroller monitored the measured impedance and detected such measured impedance when the magnitude is below 1,500 Ohms (image 2192), between 1,500 Ohms and 5,000 Ohms (image 2193), and above 5000 Ohms (image 2194). When the impedance is below 1,500 Ohms, one set of LED lights are on as shown in the figure. When the impedance is between 1,500 Ohms, and 5,000 Ohms, both sets of LED lights are on with the intensity of the LED's varying with the magnitude. When the impedance is above 5,000 Ohms, the opposite set of LED lights are on.

For example, FIG. 21D illustrates the exemplary operation during the exemplary needle insertion into a rabbit leg in what is believed to be the femoral vein. For example, when the exemplary needle is inserted into the vessel, one set of lights can be turned on and/or a particular audible signal issued. When the needle is inserted into muscle, both sets of lights are on and/or another audible signal issued. When the needle is in tissue with higher impedance, the opposite set of lights are on and/or still another audible signal issued.

It should be understood that the same or similar function can be achieved with a different number of lights or even with a single light with varying intensity, as well as various sounds, as well as or instead of a combination of light(s) and sounds. It should also be understood that the exemplary instructions used to adjust the light can be adjusted to monitor for values below or above a particular threshold and/or within a particular range or following a particular sequence.

EXAMPLES

Example 1. Impedance Phase Angle Defines Tissue Type

Figure 12A:
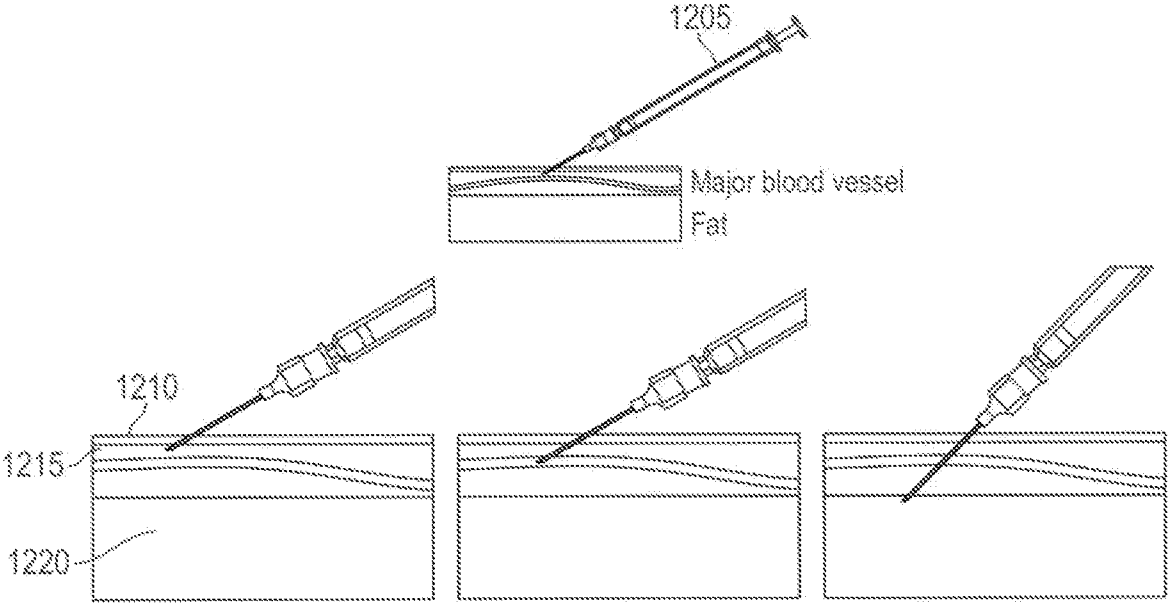
FIG. 12A is a set of exemplary illustrations showing the exemplary insertion device/apparatus inserted into different tissue types according to an exemplary embodiment of the present disclosure.

In-vivo testing was performed using fully integrated electrodes produced according to the pad printing procedure described above (see FIGS. 6 and 7). Testing was performed in a live New Zealand White rabbit to measure impedance in several different types of tissue. A cutdown was performed to expose major blood vessels in the rabbit's neck and thigh. Needles were inserted into different tissues to different depths. Magnet wire was used to connect the electrodes to an impedance analyzer (e.g., Keysight 4294A/1D5). Measured impedance (e.g., magnitude and angle) was exported to text files. FIG. 12A shows a set of exemplary diagrams and side views illustrating exemplary needle 1205 inserted into different tissue types according to an exemplary embodiment of the present disclosure. The tissue types included dermis 1210, major blood vessels 1215, and fat 1220.

Figure 12B:
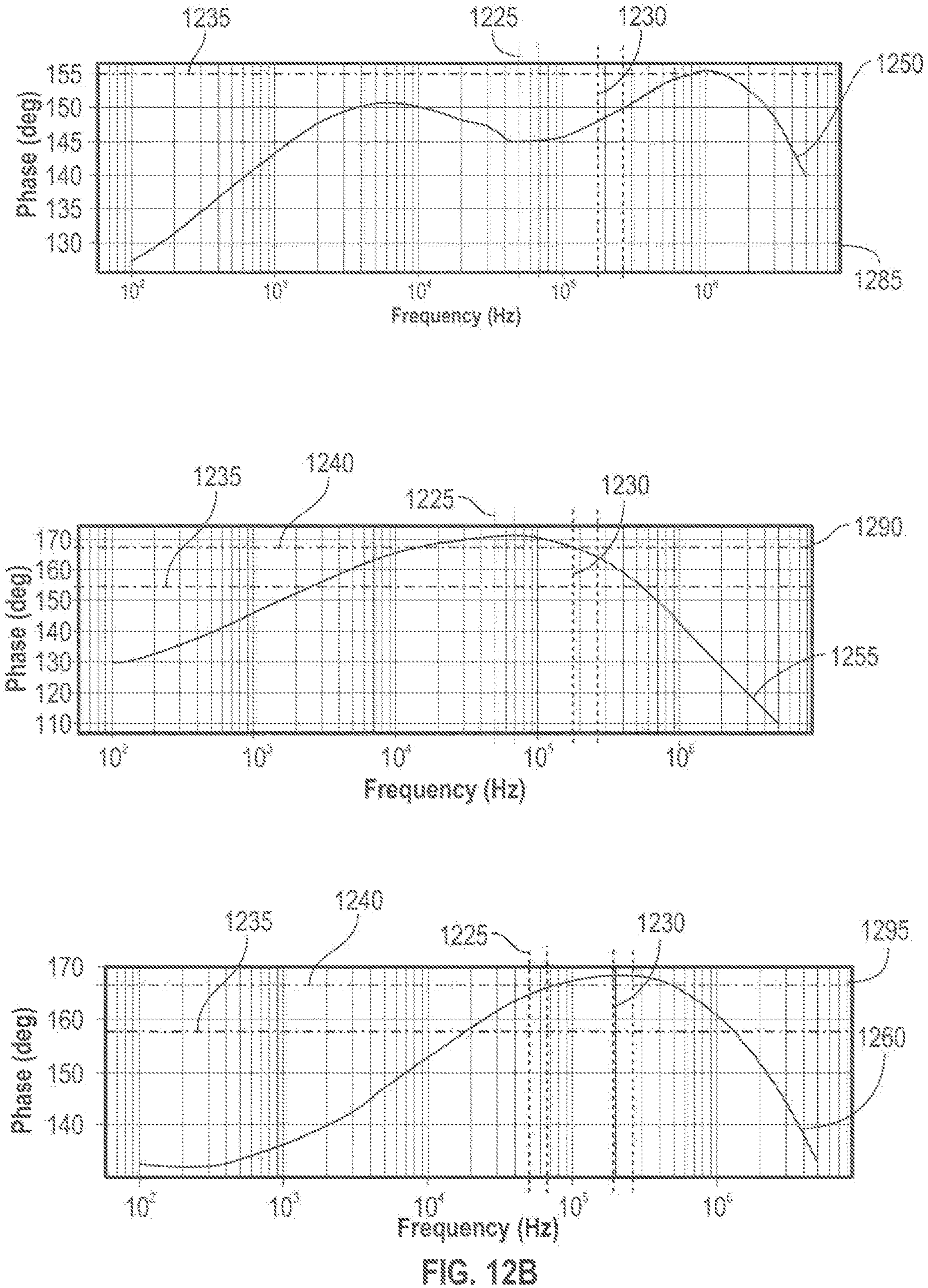
FIG. 12B is a set of exemplary graphs illustrating the impedance phase angle obtained as a function of frequency with the tip of the insertion device/apparatus inserted into different types of tissues according to an exemplary embodiment of the present disclosure.
Figure 15:
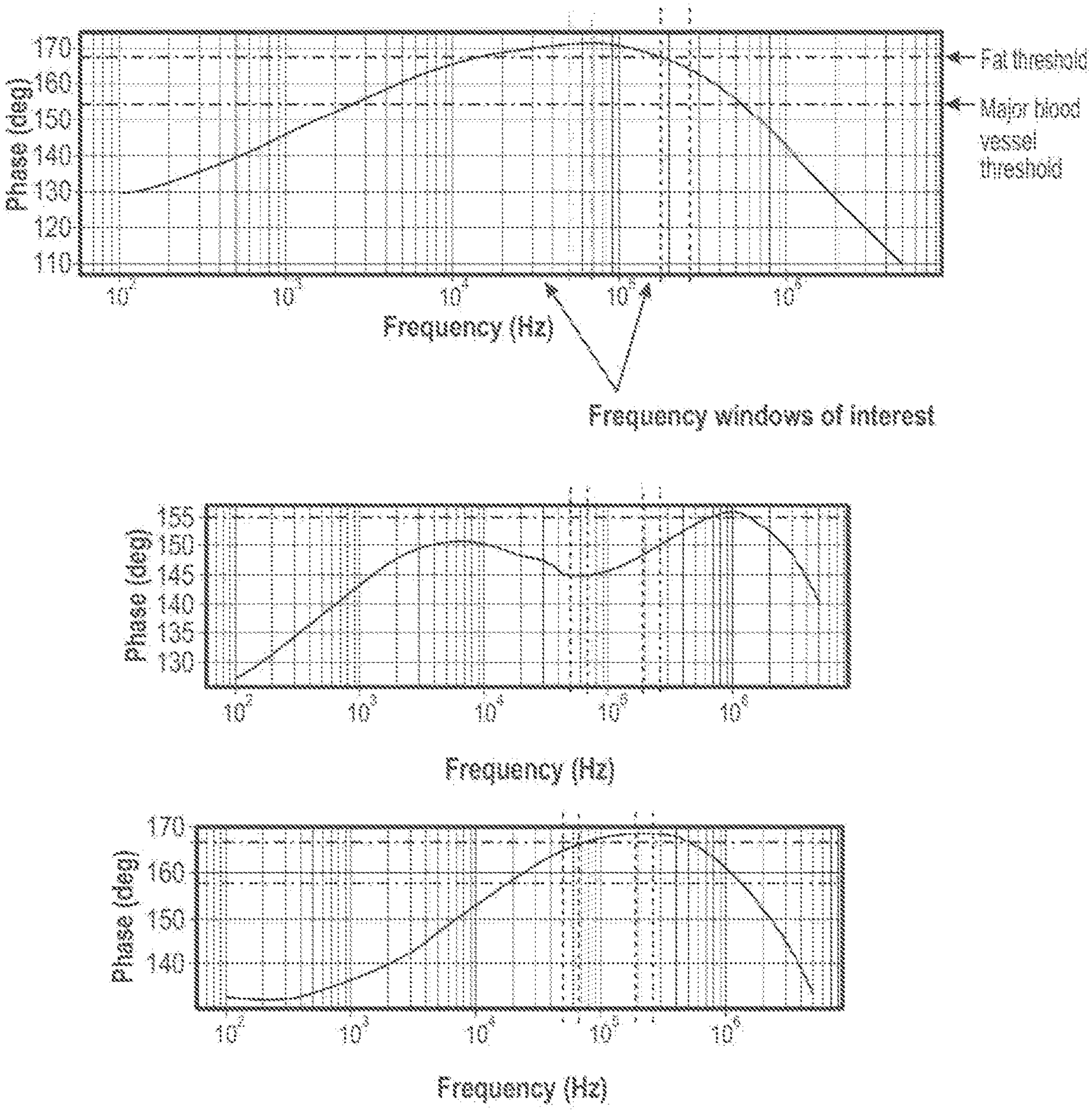
FIGS. 15-18B are exemplary graphs showing exemplary results obtained using the exemplary insertion device/apparatus according to an exemplary embodiment of the present disclosure.

FIG. 12B shows a set of exemplary graphs illustrating the impedance phase angle obtained as a function of frequency with the tip of the needle inserted into different types of tissues according to an exemplary embodiment of the present disclosure. The impedance phase angle was obtained as a function of frequency with the tip of the needle inserted into different types of tissues including dermis 1285, jugular vein 1255, and fat 1925. As shown in the graphs of FIG. 12B, the measured phase angle varies with frequency. Dashed vertical lines and dashed horizontal lines superimposed onto the graphs are provided for reference and represent discrete frequency bands and phase angle thresholds that can be used for an exemplary sensing procedure. Dark vertical lines 1225 represent a band of frequencies from 50 kHz and 65 kHz. Lighter vertical lines 1230 represent a band of frequencies from 190 kHz to 250 kHz. Dark horizontal lines 1235 are placed at 158°. Light horizontal lines 1240 are placed at 167 degrees. As shown in graph 1285, when the exemplary needle is inserted into skin, the measured phase angle 1250 remains below both dark vertical lines 1225 and light vertical lines 1230 at all frequencies. As shown in graph 1290, when the exemplary needle is inserted into the jugular vein, the measured phase angle 1255 exceeds the threshold defined by light horizontal line 1240 in the lower band of frequencies. As shown in graph 1295, when the exemplary needle is inserted into fat, the measured phase angle 1260 exceeds the threshold defined by the light horizontal line in the higher band of frequencies. The exemplary graphs shown in FIG. 15 indicate that it is possible to set thresholds for phase angle in a specific, narrow band of frequencies to detect the difference between different types of tissue.

Example 2. Impedance Magnitude Defines Tissue Type

Figure 16:
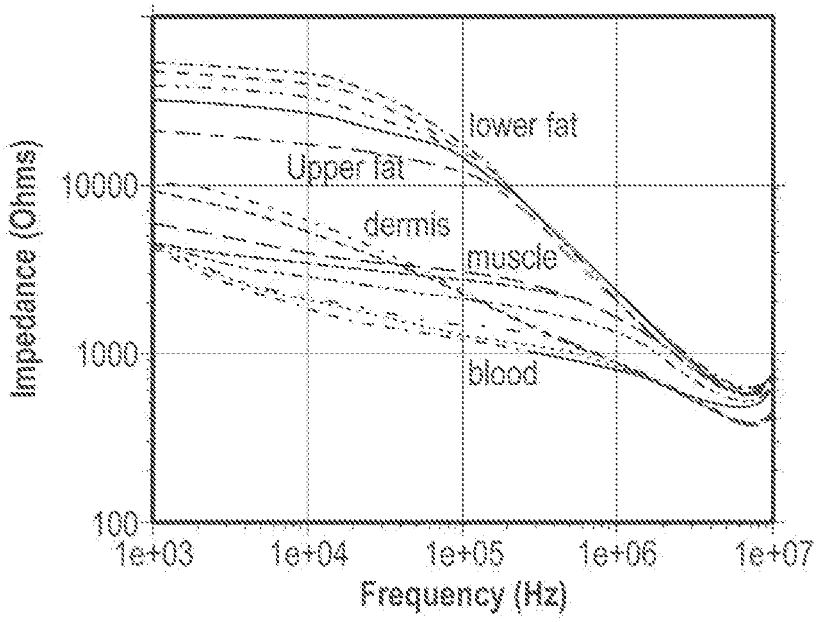
Figure 16:
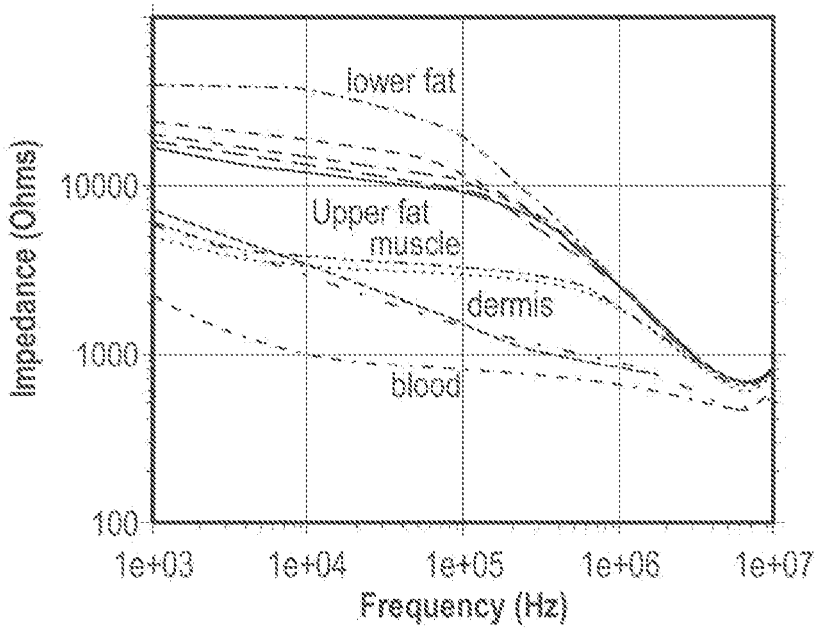
Figure 17:
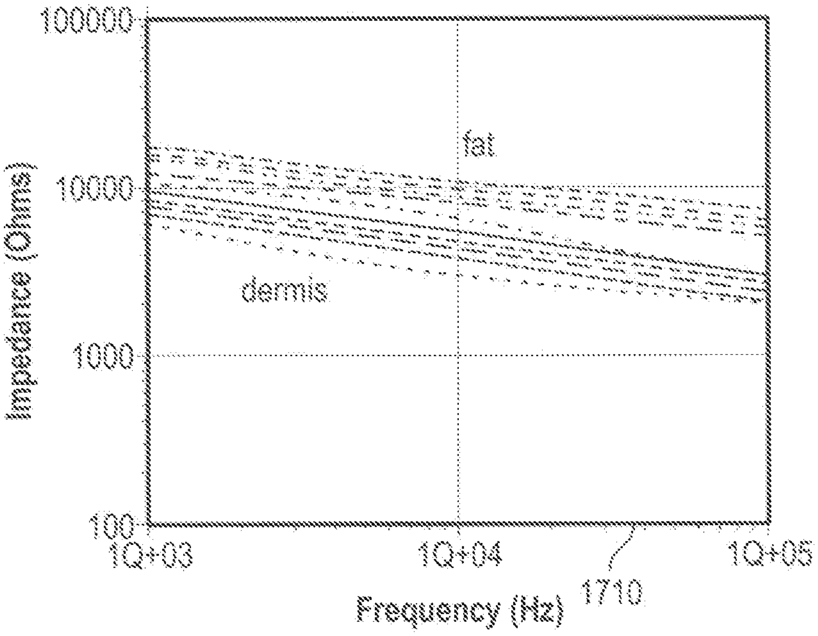
Figure 17:
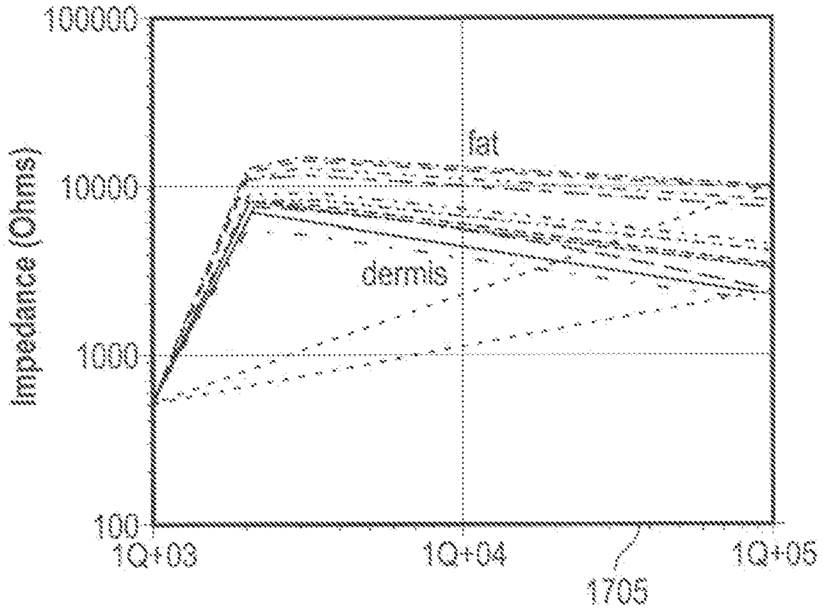
Figure 18A:
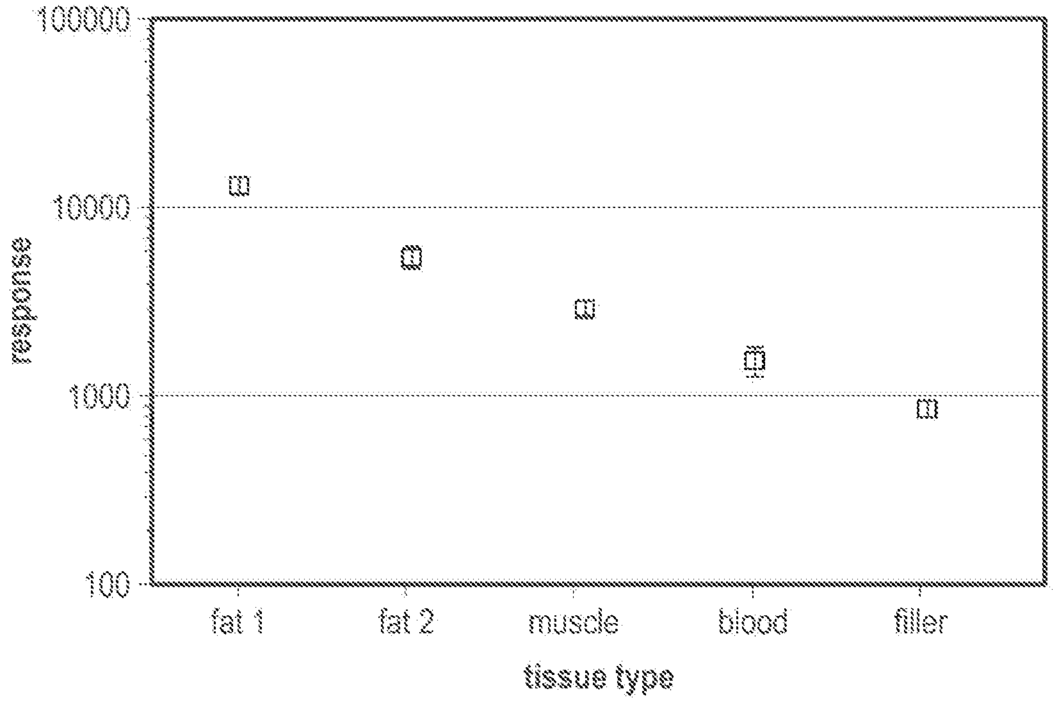
Figure 18B:
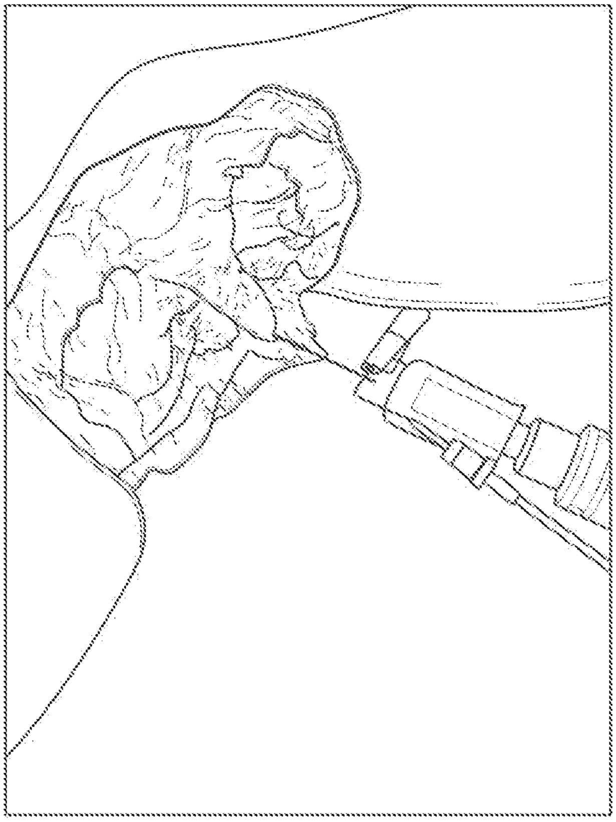
Figure 18B:
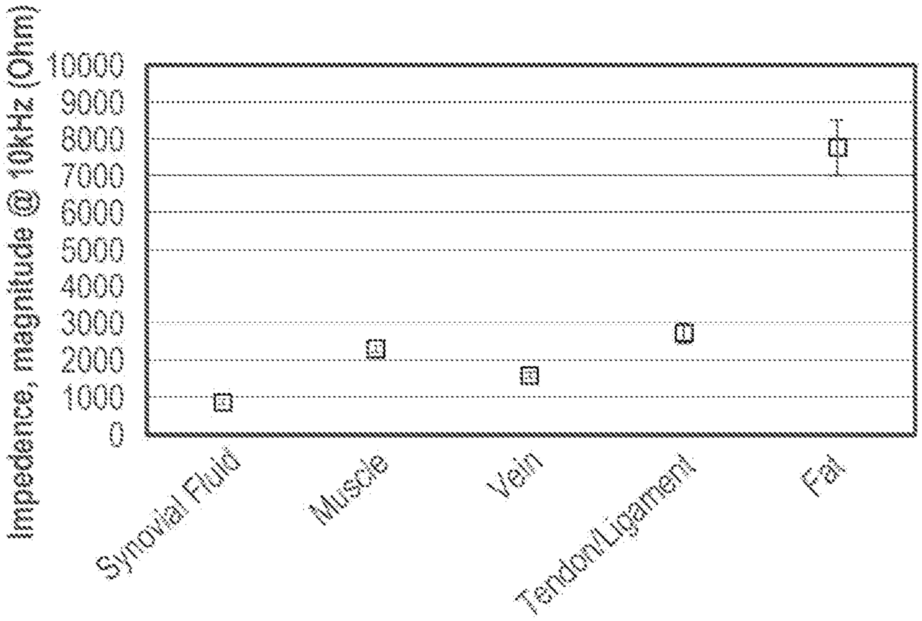

FIGS. 16-18 shows graphs illustrating exemplary results obtained using the exemplary insertion device/apparatus according to an exemplary embodiment of the present disclosure. The exemplary insertion device/apparatus was inserted into different types of fresh tissue harvested from a pig and spectra of the measured magnitude and phase angle were collected using an impedance analyzer. The exemplary graphs shown in FIG. 16 illustrate clear differentiation between the measured impedance magnitude response in various tissue as a function of frequency. Exemplary results showed a variation in response in different tissues at different frequencies. The presence of an outer layer of PET heat shrink on the outside of the needles had little effect on the relative response. Frequencies that illustrate clear differences between the measurements obtained for different tissues can be beneficial. These frequencies can vary depending on the target tissue. Results indicate that 1,000 Hz and 10,000 Hz provide sufficient response to differentiate fat from skin/muscle as there is a difference between the impedance measured in fat vs the measurements from other tissue types. The graphs illustrated in FIG. 17 illustrate that the exemplary impedance measured over a very limited range, 1,000 Hz and 10,000 Hz can provide sufficient response to differentiate skin, fat, muscle, and that a single chip solution can provide comparable relative responses to an analyzer. Exemplary results shown in graph 1705 were obtained using an exemplary impedance measurement chip while the results shown in graph 1710 were obtained using a laboratory analyzer.

FIG. 18A shows an exemplary graph comparing the variation in impedance magnitude obtained in a live Yucatan pig with exemplary electronics at a single frequency, 10,000 Hz. Each symbol represents the pooled mean result obtained from multiple continuous measurements. This same data is tabulated in Table 1. The needle was removed and then reinserted after each measurement. Error bars represent the range above and below the mean from two times the standard deviation, σ based on the pooled measurements. As there was no overlap of the results measured from fat as compared to dermis and muscle, this indicates that the exemplary needle system can sense the difference between fat and dermis/muscle using measured impedance magnitude obtained from both instruments. Further, results indicate that measurements obtained at a single frequency, e.g., 10,000 Hz can be sufficient to resolve fat vs. dermis or muscle. Measured impedance magnitude can be pooled to obtain mean and standard deviations for tissue and fluid types believed to correspond to measurements. Mean values are shown using square markers. Standard deviations are illustrated with error bars.

TABLE 1

Combination of all results correlating to different tissues and fluids measured during in-vivo testing in a Yucatan pig provided pooled estimates for impedance magnitude

| Tissue Type | Mean (ohms) | Std Dev (ohms) |
|---|---|---|
| Fat 1 | 13441.19 | 1332.923 |
| Fat 2 | 5692.242 | 810.7929 |
| Muscle | 2983.11 | 204.831 |
| Blood | 1576.659 | 268.8275 |
| Filler | 866.0706 | 81.88926 |

FIG. 18B shows an exemplary graph of the measured impedance magnitude obtained from testing performed in a freshly excised Yorkshire pig leg, specifically tissue and fluid in and around the stifle joint which is roughly equivalent to a human knee. Data was collected using an exemplary system at a single frequency, 10,000 Hz. Each symbol represents the mean result obtained from multiple measurements. This same data is tabulated in Table 2. The needle was removed and then reinserted after each measurement. Error bars represent the range above and below the mean from three times the standard deviation, σ based on the pooled measurements. For a normal data set, the 36 range contains approximately 99.7% of the values. (See, e.g., Reference 7).

TABLE 2

Mean measured impedance magnitude collected from different tissues and fluids measured during in-vitro testing in a freshly harvested Yorkshire pig. 3x standard deviation also provided as an indication of scatter

| Tissue Type | Mean (ohms) | Std Dev (ohms) |
|---|---|---|
| Synovial Fluid | 921 | 72 |
| Muscle | 2346 | 104 |
| Vein | 165 | 55 |
| Tendon/Ligament | 2759 | 252 |
| Fat | 7767 | 763 |

Based on the exemplary data including, but not limited to, the data described and/or incorporated herein, an exemplary device and/or system can monitor the measured impedance magnitude for values within specific ranges to infer different tissue types or fluids. For the 26Ga RW needle coated with a 0.001 in thick layer of polyimide and with an outer coating of 0.001 in thick silver filled ink used to measure the data, the ranges of impedance magnitude are included in Table 3.

TABLE 3

Range of Exemplary Impedance Magnitudes in Tissue/Fluid

| Tissue/Fluid Type | Impedance Magnitude (Ohms) |
|---|---|
| Whole Blood | 1,000 Ohms to 2,000 Ohms |
| Muscle | 2,000 Ohms to 5,000 Ohms |
| Fat | 5,000 Ohms to 40,000 Ohms |
| Synovial Fluid | 200 Ohms to 1,000 Ohms |

In addition to the specific needle size and materials, these are results specific to one frequency, 10,000 Hz and one specific needle point.

A person of skill in the art would recognize that changes to an exemplary needle geometry lead to a reduction in the measured impedance magnitude. An increase in the needle gage or size increases the sensing area and the amount of tissue in contact with the needle. For a fixed voltage, more electrical current will appear to pass through the tissue, following Ohm's law. This will decrease the measured impedance magnitude with a linear change tied to the change in the circumference of the needle. Increasing the thickness of the insulating area will increase the distance that the electrical current must pass through hence, increasing the amount of tissue in the electrical path. This will lead to a decrease in the measured impedance magnitude which will be linearly proportional to the change in thickness. Similarly, a change in the needle point will lead to a change in geometry, which will affect the measured impedance magnitude. For example, decreasing the primary grind produces a point with a shallower angle. Based on geometry, this increases the effective distance that electrical current must travel and increases the amount of tissue that that the current must pass through. This can increase or decrease the measured impedance magnitude. A skilled practitioner would also recognize that a change in the frequency may also alter the measured impedance magnitude or phase as a change in frequency will change the relative contributions of the resistance and reactance. Accordingly, depending on the features of the exemplary device, the range of impedance magnitude per tissue or fluid type can be readily determined by a skilled practitioner according to the methods of the invention described herein.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

[1] Kai Kronström, Petri Ahonen, Sanna MÄKI, Timo Elomaa, Juho Kari, US 2018/0296197 A1, Biopsy Needle For Biopsy Sampling, Biopsy Device, And Methods Of Manufacturing A Biopsy Needle Or A Biopsy Device.

[2] Kai Kronstrom, Petri Ahonen, Juho Kari, Riitta Seppanen, US 2016/0029920 A1, Bioimpedance Sensor, Stylet, Cannula And Method For Measuring Biompedance.

[3] Joho Yun, Jinhwan Kim, Jong-Hyun Lee, "Fabrication of Fine Electrodes on the Tip of Hypodermic Needle Using Photoresist Spray Coating and Flexible Photomask for Biomedical," Journal of Visualized Experiments, November 2017|129|e56622|.

[4] Joho Yun, Hyeon Woo Kim, Yangkyu Park, Jung-Joon Cha, Jeong Zoo Lee, Dong Gil Shin, and Jong-Hyun Lee, Micro electrical impedance spectroscopy on a needle for ex vivo discrimination between human normal and cancer renal tissues, Biomicrofluidics 10, 034109 (2016).

[5] Ivorra Cano, Antoni, Contributions to the measurement of electrical impedance for living tissue ischemia injury monitoring, Doctoral Thesis, Universitat Politècnica de Catalunya, 2005.

[6] Mohammed H. Abduljabbar, Mohammad A. Basendwh. "Complications of hyaluronic acid fillers and their managements," Journal of Dermatology & Dermatologic Surgery 20 (2016) 100-106

[7] Wheeler, D. J.; Chambers, D. S. (1992). Understanding Statistical Process Control. SPC Press.

[8] Covidien, "Principles of Electrosurgery," Boulder CO, 2008.

[9] Rocha, Rafael Dahmer, Pinto, Renata Reis, Tavares, Diogo Paes Barreto Aquino, Gonεalves, Claudia Sofia Aires, "Step-by-step of ultrasound-guided core-needle biopsy of the breast: review and technique," Radiol Bras. 2013 July/Ago; 46(4):234-241.

[10] Selfridge, Alan, and Lewin, Peter A., "Wideband Spherically Focused PVDF Acoustic Sources for Calibration of Ultrasound Hydrophone Probes," IEEE Transactions on Ultrasonics, Ferroelectrics, and Frequency Control, Vol. 47, No. 6, November 2000

[11] Burgher, Julie M; Barton, Jennifer M; Farooq, Michael M; Vasek, Jeff; Scott, Robert W; Freischlag, Julie A, "Grove, Robert I, PhotoPoint photodynamic therapy with local drug delivery eliminates vessel wall cells in arteriovenous graft models," Cardiovascular radiation medicine, ISSN: 1522-1865, Vol: 3, Issue: 3-4, Pages 163-168 (2002).

[12] Dorothee Schär Christoph A. Ramseier Sigrun Eick Nicole B. Arweiler Anton Sculean Giovanni E. Salvi, "Anti-infective therapy of peri-implantitis with adjunctive local drug delivery or photodynamic therapy: six-month outcomes of a prospective randomized clinical trial, Clinical Oral Implants Research," Vol. 24(1), pages 104-110.

[13] Théophile Pelras Sarah Glass, Tom Scherzer, Christian Elsner, Agnes Schulze, and Bernd Abel, "Transparent Low Molecular Weight Poly(Ethylene Glycol) Diacrylate-Based Hydrogels as Film Media for Photoswitchable Drugs," Polymers 2017, Vol 0.9, page 639 (2017).

[14] Liberman, Laura, "Percutaneous Imaging-Guided Core Breast Biopsy: State of the Art at the Millennium," AJR: 174, May 2000.

[15] Ribatti, Domenico, Annese, Tiziana and Longo, Vito, "Angiogenesis and Melanoma," Cancers 2010, 2, 114-132.

[16] Sepulveda, Abel, Buchanan, Edward P., "Vascular Tumors," Semin Plast Surg. 2014 May; 28(2): 49-57

What is claimed is:

1. A method comprising:

providing a needle having a lumen extending along a length thereof, a cladding layer formed on an exterior of the needle, and an optically-transmissive coating formed on an exterior of the cladding layer, wherein a tip of the needle is adapted to puncture an outer tissue structure of a subject overlaying a target location within the subject and be directed toward the target location;

transmitting, by the optically-transmissive coating or the cladding layer, a first optical radiation to tissue adjacent the needle after the outer tissue structure is punctured;

receiving, by at least one processor, data characterizing a second optical radiation from the other of the optically-transmissive coating or the cladding layer based on the first optical radiation;

determining, by the at least one processor, based on the second optical radiation, that the tip of the needle is at the target location; and delivering a substance to the target location via the lumen of the needle.

2. The method according to claim 1, wherein the transmission of the first optical radiation is performed by a controller.

3. The method according to claim 2, wherein the determining is performed by the at least one processor in real time and continuously.

4. The method according to claim 1, wherein the needle is adapted to provide an audible, tactile or visual alert to indicate that the tip of the needle is at the target location.

5. The method according to claim 1, wherein the needle further comprises a syringe containing the substance, wherein the syringe is configured to facilitate the releasing of the substance into or near at least one area of the target location via the lumen.

6. The method according to claim 1, wherein the substance is a pharmacological agent.

7. The method according to claim 6, wherein the pharmacological agent is at least one of a drug, a therapeutic, a cellular material, one or more cells, a genetic material, one or more stem cells or an immunotherapy agent.

8. The method according to claim 1, wherein the substance is a filler.

9. The method according to claim 1, wherein the target location is a subcutis, a tumor, or a joint.

10. The method according to claim 1, wherein the target location is a tumor.

11. The method according to claim 1, wherein the target location is a joint.

12. The method according to claim 1, further comprising obtaining a biopsy sample from the subject through the lumen.

13. The method according to claim 1, further comprising determining, by the at least one processor, a three-dimensional location of the tip of the needle.

14. The method according to claim 13, wherein the needle is communicatively coupled to a wireless communication device, the method further comprising:

transmitting, via the wireless communication device using one or more wireless communication protocols, the data characterizing the second optical radiation to a remote computing device.

15. The method according to claim 14, further comprising generating, by the at least one processor, an image to be provided to a display of the remote computing device, wherein the generated image includes at least a portion of the subject and at least a portion of the needle in a three-dimensional space within the subject based on the three-dimensional location of the tip of the needle.

16. The method of claim 14 wherein the remote computing device is any one of a computer, a mobile phone and a tablet.

* * * * *